(12) United States Patent
Li et al.

(10) Patent No.: US 11,530,181 B2
(45) Date of Patent: Dec. 20, 2022

(54) IL-6 INHIBITORS AND METHODS OF TREATMENT

(71) Applicant: University of Florida Research Foundation, Incorporated, Gainesville, FL (US)

(72) Inventors: Chenglong Li, Gainesville, FL (US); Liguang Mao, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 192 days.

(21) Appl. No.: 16/971,528

(22) PCT Filed: Feb. 22, 2019

(86) PCT No.: PCT/US2019/019069
§ 371 (c)(1),
(2) Date: Aug. 20, 2020

(87) PCT Pub. No.: WO2019/165158
PCT Pub. Date: Aug. 29, 2019

(65) Prior Publication Data
US 2021/0206718 A1    Jul. 8, 2021

Related U.S. Application Data

(60) Provisional application No. 62/633,771, filed on Feb. 22, 2018.

(51) Int. Cl.
| | |
|---|---|
| *C07D 209/00* | (2006.01) |
| *C07D 237/02* | (2006.01) |
| *C07D 401/02* | (2006.01) |
| *C07D 401/04* | (2006.01) |
| *C07D 409/04* | (2006.01) |
| *A61K 31/165* | (2006.01) |
| *A61K 31/216* | (2006.01) |
| *A61P 35/00* | (2006.01) |
| *C07D 207/335* | (2006.01) |

(52) U.S. Cl.
CPC ......... *C07D 207/335* (2013.01); *A61P 35/00* (2018.01)

(58) Field of Classification Search
CPC .. C07D 209/00; C07D 237/02; C07D 401/02; C07D 401/04; C07D 409/04; A61K 31/165; A61K 31/216; A61K 31/415; A61P 35/00
See application file for complete search history.

(56) References Cited

FOREIGN PATENT DOCUMENTS

| WO | WO 2007/002559 A1 | 1/2007 |
| WO | WO 2017/198700 A1 | 11/2017 |

OTHER PUBLICATIONS

King (Journal of the Chemical Society (1927) 1049-60). Abstarct.*
John (Journal fuer Praktische Chemie (Leipzig) (1934), 139, 97-104). Abstarct.*
Coates et al. (Journal of the Chemical Society (1943) 406-13). Abstarct.*
International Search Report and Written Opinion dated Jun. 5, 2019 in connection with PCT/US2019/019069.
[No Author Listed], Pubchem Substance Record for SID 259632448. Available Date: Dec. 10, 2017. [retrieved on May 14, 2019]. Retrieved from the Internet: <http://pubchem.ncbi.nlm.nih.gov/substance/259632448>. 4 pages.

* cited by examiner

*Primary Examiner* — Bruck Kifle
(74) *Attorney, Agent, or Firm* — Wolf, Greenfield & Sacks, P.C.

(57) ABSTRACT

The instant invention describes compounds having IL-6 modulating activity, and methods of treating diseases, disorders or symptoms thereof mediated by IL-6.

20 Claims, 9 Drawing Sheets

Pronase: protein = 1:1000
Proteolysis time: 30 min

Pronase: protein = 1:2000
Proteolysis time: 30 min

Pronase: protein = 1:2000
Proteolysis time: 20 min

Pronase: protein = 1:2000
Proteolysis time: 15 min

IL-6 INHIBITORS AND METHODS OF TREATMENT

CROSS-REFERENCE TO RELATED APPLICATIONS

This application is a National Phase Application under 35 U.S.C. 371 of PCT International Application No. PCT/US2019/019069, filed Feb. 22, 2019, which claims priority to U.S. Provisional Application No. 62/633,771, filed Feb. 22, 2018, which is incorporated herein by reference in its entirety.

STATEMENT OF RIGHTS TO INVENTIONS MADE UNDER FEDERALLY SPONSORED RESEARCH

This invention was made with government support under NS088437 awarded by the National Institutes of Health. The government has certain rights in the invention.

BACKGROUND

Interleukin-6 (IL-6) is a cytokine produced by a large variety of cell types and can exert its effects on virtually all cells. IL-6 is involved in a broad array of biological activities such as immune responses, apoptosis, and proliferation [Kishimoto T, Akira S, Taga T. Interleukin-6 and its receptor: a paradigm for cytokines. Science 1992, 258, 593-597]. However, when IL-6 is dysregulated or constantly expressed at a high level, it will cause numerous pathological conditions (FIG. 1) [Bernd S, May S. IL-6 as a drug discovery target. DDT 1998, 5, 202-213]. For example, uncontrolled and prolonged activation of inflammation, referred to as chronic inflammation, is a hallmark of many diseases including cancer, and one of the most abundant cytokines associated with this condition is IL-6 [Mantovani A, Paola A, Antonio S, et al. Cancer-related inflammation. Nature 2008, 454, 436-444]. Because of these two opposite effects, IL-6 is also recognized as a "wolf in sheep's clothing". One possible reason for this difference may result from the concentration of IL-6 present in plasma. In healthy persons, the IL-6 level is as low as the detection limit of 1 pg/ml [Stefan R J. IL-6 trans-signaling via the soluble IL-6 receptor: importance for the pro-inflammatory activities of IL-6. Int J Biol Sci 2012, 8, 1237-1247], while in pathological conditions, the level of plasma IL-6 can surge by one hundred thousand fold to as high as the low microgram range (Table 1) [Nowell M A, Richards P J, Horiuchi S, et al. Soluble IL-6 receptor governs IL-6 activity in experimental arthritis: blockade of arthritis severity by soluble glycoprotein 130. J Immunol 2003, 171, 3202-3209; Waage A, Brandtzaeg P, Halstensen A, et al. The complex pattern of cytokines in serum from patients with meningococcal septic shock. J Exp Med 1989, 169, 333-338].

IL-6 was first identified by its ability to activate the maturation of B cells to antibody-secreting plasma cells [Okada M. B cell growth factors and B cell differentiation factor from human T hybridomas. Two distinct kinds of B cell growth factor and their synergism in B cell proliferation. J Exp Med 1983, 157, 583-590]. It has been referred to by several names such as B-cell stimulatory factor-2 (BCSF-2), interferon-2 (IFN-2), hepatocyte stimulating factor (HSF), macrophage granulocyte inducer type 2 (MGI-2A) or thrombopoietin [Kishimoto T. The biology of interleukin-6. Blood 1989, 74, 1-10], which also illustrates its versatile functions. A 1.9 Å crystal structure of IL-6 was reported by Somers and his coworkers in 1997 [Somers W, Stahl M, Seehra, J. 1.9 Å crystal structure of interleukin 6: implications for a novel mode of receptor dimerization and signaling. The EMBO Journal 1997, 16, 989-997; Xu G-Y, Yu H-A, Hong J, et al. Solution structure of recombinant human interleukin-6. J Mol Biol 1997, 268, 468-481]. It is a 26-kDa glycoprotein that contains 212 amino acids arranged in a five helix bundle, with four of them forming a classical four-helix bundle with a conformation termed "up-up-down-down" [Zaccaro L, Bucci E, Vitale M, et al. Synthetic peptides mimicking the interleukin-6/gp 130 interaction: a two-helix bundle system. Design and conformational studies. J Pept Sci. 2003, 9, 90-105; Boulanger M J, Chow D C, Brevnova E E, et al. Hexameric structure and assembly of the interleukin-6/IL-6 alpha-receptor/gp130 complex. Science 2003, 300, 2101-2104].

TABLE 1

IL-6 levels in healthy individuals and in selected disease states.

| Condition | Plasma IL-6 conc. |
| --- | --- |
| Healthy individual | 1 pg/ml |
| Rheumatoid arthritis | 150 ng/ml |
| Septic condition | low μg/ml |

11-6 activates a cell surface signaling assembly composed of IL-6, the IL-6 α-receptor (IL-6Rα), and the shared signaling receptor gp130. IL-6 first binds to IL-6Rα to form a binary complex, then recruits gp130 to form the IL-6/IL-6Rα/gp130 heterotrimer. Furthermore, homodimerization of the IL-6/IL-6Rα/gp130 heterotrimer occurs by interactions between IL-6 of one trimer and the D1 domain of gp130 of the other trimer, forming a hexamer [Boulanger M J, Chow D C, Brevnova E E, et al. Hexameric structure and assembly of the interleukin-6/IL-6 alpha-receptor/gp130 complex. Science 2003, 300, 2101-2104; Eric A, Marie-Christophe B, Jean-Michel D. Interleukin-6: From identification of the cytokine to development of targeted treatments. Joint Bone Spine 2010, 77, 532-536]. The reciprocal homodimerization of the IL-6/IL-6Rα/gp130 trimer triggers the activation of associated Janus kinase (JAK). Then, JAK causes autophosphorylation as well as the phosphorylation of gp130. After that, the phosphorylated positions on JAK and gp130 serve as the docking sites of downstream effector signal transducer and activator of transcription 3 (STAT3) SH2 domain, followed by reciprocal dimerization of phosphorylated STAT3, nuclear translocation, DNA binding and cancer gene transcription [Darnell J E. STATs and gene regulation. Science, 1997, 277, 1630-1635; Jinxia D, Fedora G, Nouri N. Small Molecule Inhibitors of Stat3 Signaling Pathway. Curr Cancer Drug Targets, 2007, 7, 91-107]. Other than the IL-6/gp130/STAT3 signaling pathway, IL-6 can also activate the PI3K/AKT pathway and the Raf/MEK/ERK pathway. The existence of these different pathways activated by IL-6 appears to be highly cell type-dependent [Haegeman G. Structural analysis of the sequence coding for an inducible 26-kDa protein in human fibroblasts. Eur J Biochem 1986, 159, 625-632; Yamasaki K. Cloning and expression of the human interleukin-6 (BSF-2/IFN beta 2) receptor. Science 1988, 241, 825-828].

The extracellular structure and assembly of the IL-6/IL-6Rα/gp130 complex was solved in 2003 by the Garcia group [Boulanger M J, Chow D C, Brevnova E E, et al. Hexameric structure and assembly of the interleukin-6/IL-6 alpha-receptor/gp130 complex. Science 2003, 300, 2101-2104], and the full-length transmembrane IL-6/IL-6Rα/gp130 cytokine receptor complex was solved by the same group in 2011 [Patrick J, Georgios S, Amanda J, et al. structural snapshots of full-length Jak1, a transmembrane gp130/IL-6/IL-6Rα cytokine receptor complex, and the receptor-Jak1 holocomplex. *Structure* 2011, 19, 45-55]. The IL-6 extracellular signaling portion is a symmetric hexamer, which contains two IL-6, two IL-Rα and two gp130 subunits assembling sequentially and cooperatively. There are five main binding epitopes involved in this complex, namely site I, site II (IIa and IIb) and site III (IIIa and IIIb). [Boulanger M J, Chow D C, Brevnova E E, et al. Hexameric structure and assembly of the interleukin-6/IL-6 alpha-receptor/gp130 complex. *Science* 2003, 300, 2101-2104].

Site I is formed when IL-6 binds to IL-6Rα. Binding occurs between the D3 domain of IL-6Rα and the A and D helices of IL-6. It covers an area of 1200 Å$^2$. The key residues in this binding site are Phe229 and Phe279 on the IL-6Rα D3 domain, Arg179 and Lys171 on IL-6. Site II is formed when the IL-6/IL-6Rα complex binds to gp130. Site IIa consists of the elbow region of D2 and D3 on gp130 and the A and C helices on IL-6. It covers an area of 1272 Å$^2$, where Phe169 on the gp130 elbow region and Arg24, Lys27, Arg30 and Asp34 contribute the most to the binding surface. Site IIb consists of the D3 domain on IL-6Rα and the D3 domain on gp130, which covers a surface area of 1078 Å$^2$. Site III is formed when two IL-6/IL-6Rα/gp130 trimers dimerize with each other. Site IIIa consists of the tip of the IL-6 four-helix bundle and the bottom β sheet of the D1 domain of gp130, which covers an area of 1276 Å$^2$. The N-terminal peptide of gp130 (from Leu2 to Cys6) is solvent-exposed and inserts in a groove on the surface of IL-6 formed by the A, B and C, D inter-helical loops. Trp157 on IL-6 is also found to be critical, contributing 21% of the total buried surface area. This finding is consistent with previous results obtained through mutagenesis that this aromatic signature residue is of great importance in Site IIIc [Paonessa G. Graziani R, De S A, et al. Two distinct and independent sites on IL-6 trigger gp 130 dimer formation and signaling. *EMBO J* 1995, 14, 1942-1951; Barton V A, Hudson K R, Heath J K. Identification of Three Distinct Receptor Binding Sites of Murine Interleukin-11. *J Biol Chem* 1999, 274, 5755-5761]. Site IIIb involves the interaction between the tip of D1 domain on gp130 and the D2 domain of IL-6Rα, which covers a surface area of 473 Å$^2$.

Other than IL-6, there are seven other members in the IL-6 family of cytokines, which are IL-11, leukemia inhibitory factor (LIF), oncostatin M (OSM), cardiotrophin-1 (CT-1), ciliary neurotrophic factor (CNTF), cardiotrophin-like cytokine (CLC) and IL-27 [Ursula A W, Jacqueline M S. The gp130 Receptor Cytokine Family: Regulators of Adipocyte Development and Function. *Curr Pharm Des.* 2011, 4, 340-346]. They are grouped together because all of these cytokines require the signal receptor subunit gp130 in the signal transduction process, so they are also referred to as gp130 related cytokines. These cytokines act in a pleiotropic manner, and are also redundant in regulating various biological processes [Ernst M, Jenkins B J. Acquiring signalling specificity from the cytokine receptor gp130. *Trends in genetics* 2004, 20, 23-32]. The IL-6 family of cytokines participate in signal transduction mainly through the JAK/STAT pathway and the most common STAT activated is STAT3 [Heinrich P C, Behrmann I, Haan S, et al. Principles of interleukin (IL)-6-type cytokine signalling and its regulation. *Biochem J* 2003, 374, 1-20].

As mentioned above, as all members in the IL-6 family of cytokines transduce their signals through glycoprotein 130 (gp130), they still require other receptors to form the signal transduction complex and the stoichiometry varies. For IL-6 and IL-11, both initially bind to the IL-6 receptor α or IL-11 receptor α [White U A, Stewart W C, Mynatt R L, et al. Neuropoietin attenuates adipogenesis and induces insulin resistance in adipocytes. *J Biol Chem* 2008, 283, 22505-22512], respectively. The dimer then recruits and associates with gp130 to form a trimer, followed by homodimerization of two of these trimers for signal transduction. For LIF and CT-1, both require the LIF receptor (LIFR) to form a complex with gp130 to mediate signal transduction [Gearing D P, Thut C J, VandeBos T, et al. Leukemia inhibitory factor receptor is structurally related to the IL-6 signal transducer, gp130. *EMBO J* 1991, 10, 2839-2848; Pennica D, Shaw K J, Swanson T A, et al. Cardiotrophin-1. Biological activities and binding to the leukemia inhibitory factor receptor/gp130 signaling complex. *J Biol Chem* 1995, 270, 10915-10922]. In addition to LIFR, CT-1 has also been reported to recruit another as yet unidentified alpha receptor [Robledo O, Guillet C, Chevalier S, et al. Hepatocyte-derived cell lines express a functional receptor for cardiotrophin-1. *Eur Cytokine Netw* 1997, 8, 245-52]. For CNTF and CLC, both require CNTFRα and LIFR to form a complex with gp130 for signal transduction [Davis S, Aldrich T H, Stahl N, et al. LIFR beta and gp130 as heterodimerizing signal transducers of the tripartite CNTF receptor. *Science* 1993, 260, 1805-1808; Elson G C, Lelievre E, Guillet C, et al. CLF associates with CLC to form a functional heteromeric ligand for the CNTF receptor complex. *Nat Neurosci* 2000, 3, 867-872]. For OSM, it has been reported to either utilize the LIFR complex or alternatively utilize an OSM receptor (OSMR) to form a complex with gp130 during signaling [Ichihara M, Hara T, Kim H, et al. Oncostatin M and leukemia inhibitory factor do not use the same functional receptor in mice. *Blood* 1997, 90, 165-173], although some studies indicate that OSM primarily signals via the OSMR and not the LIFR. For IL-27, its cell signaling engages a gp130/WSX-1 heterodimeric receptor complex [Pflanz S, Hibbert L, Mattson J, et al. WSX-1 and glycoprotein 130 constitute a signal-transducing receptor for IL-27. *J Immunol* 2004, 172, 2225-2231].

From this discussion, it is apparent that IL-6 and IL-11 signal transduction require the dimerization of two gp130 subunits, while in signaling by other IL-6 family members, only one gp130 is involved. As a result, the binding site III in IL-6 signaling is unique from LIF, CNTF, CLC, CT-1, OSM and IL-27. It may share some similarity with IL-11 signaling, although the complex crystal structure of this signaling complex remains unknown.

IL-6 was first discovered as an inflammatory cytokine and plays an important role in the immune response. Tissue damage or pathogen invasion is always associated with inflammation, which is necessary to help remove necrotic debris. Macrophages are recruited to the infected area in the inflammatory response, which produces reactive oxygen species (ROS) and proteases [Ma J, Chen T, Mandelin J. Regulation of macrophage activation. *Cell Mol Life Sci* 2003, 60, 2334-2346]. This response helps to kill or degrade the pathogens. Under such a harsh microenvironment, normal cells would also be killed in the absence of a mediator to protect these cells. IL-6, together with various other inflammatory mediators, not only plays an important role in driving inflammatory mechanisms, but also acts as the protector for both cells in the immune system and the injured or infected tissues [Shinozaki M, Hirahashi J, Lebedeva T, et al. IL-15, a survival factor for kidney epithelial cells, counteracts apoptosis and inflammation during nephritis. *J Clin Invest* 2002, 109, 951-960; Tourbah A, Linnington C, Bachelin C, et al Inflammation promotes survival and migration of the CG4 oligodendrocyte progenitors transplanted in the spinal cord of both inflammatory and demyelinated EAE rats. *J Neurosci Res* 1997, 50, 853-861]. However, this protection can go too far and, in some cases, it also extends to cells that strayed from normal cell cycle regulatory pathways [Hideshima T, Nakamura N, Chauhan D, et al. Biologic sequelae of interleukin-6 induced PI3-K/Akt signaling in multiple myeloma. *Oncogene* 2001, 20, 5991-6000], which may eventually cause cancer. Strong support for the role of IL-6 in inflammation and cancer comes from research showing that IL-6 was produced by stroma and inflammatory cells within the tumor microenviroment. The abundant IL-6 then plays its role in activating JAK/STAT3 signal transduction and promotes cell proliferation. In inflammatory cells and tumor cells, extremely high levels of activated STAT3 were observed particularly at the invasive edge of tumors [Bromberg J, Wang T. Inflammation and Cancer: IL-6 and STAT3 Complete the Link. *Cancer Cell* 2009, 15, 79-80]. Another piece of evidence showing the role of IL-6 in protecting cancer cells comes from the fact that IL-6 is found to mediate many unwanted effects, such as making cancer cells resistant to chemotherapeutic drugs [Hodge D R, Xiao W, Wang L H, et al. Activating mutations in STAT3 and STAT5 differentially affect cellular proliferation and apoptotic resistance in multiple myeloma cells. *Cancer Biol Ther* 2004, 3, 188-194; Frassanito M A, Cusmai A, Iodice G, et al. Autocrine interleukin-6 production and highly malignant multiple myeloma: relation with resistance to drug-induced apoptosis. *Blood* 2001, 97, 483-489].

So far, researchers have found that there are numerous cell types which can respond to IL-6; the cell types include but are not limited to, lung, heart, ovary, kidney, liver, macrophages, astrocytes, endometrial stromal cells, monocytes, amnion-derived cells, Kupffer cells, osteoblasts, microglia, multiple myeloma, Leydig cell precursors (testes), mast cells, fibroblasts (dental pulp, gingival, nasal turbinate, polyps, synovial), human endothelial cells, and prostatic intraepithelial neoplasia cells [Suganuma M, Okabe S, Kurusu M, et al. Discrete roles of cytokines, TNF-alpha, IL-1, IL-6 in tumour promotion and cell transformation. *Int J Oncol* 2002, 20, 131-136]. Low level production of IL-6 typically occurs in these cells. However in a situation like inflammation, IL-6 is constantly expressed at a high level, which drives inflammation itself but also increases the risk of tumorigenesis in these types of cells, mainly through the IL-6/JAK/STAT3 signal transduction pathway. Indeed, various types of cancers are found to be associated with the IL-6/JAK/STAT3 signal transduction pathway, which includes multiple myeloma, chronic lymphocytic leukemia (CLL), acute myelogenous leukemia (AML), large granular lymphocyte leukemia (LGL), lung cancer, breast cancer, renal cancer, prostate cancer, pancreatic carcinoma, melanoma, colon carcinoma, gastric carcinoma, cervical cancer, ovarian cancer, liver cancer, and head and neck cancers [David R H, Elaine M H, William L F. The role of IL-6 and STAT3 in inflammation and cancer. *Eur J Cancer* 2005, 2502-2512].

As discussed above, IL-6 belongs to the gp130-related cytokine family. It plays an important role in the IL-6/gp130/STAT3 signaling pathway, which was found to be protumorigenic in many cancers. IL-6 first binds to the IL-6 receptor a (IL-6Rα), which recruits gp130 on the cell membrane; then dimerization of two of the IL-6/IL-6Rα/gp130 trimers allows signal transduction via gp130 cytoplasmic domains. This activates JAK then STAT3 (Tyr705 phosphorylation), leading to STAT3 nuclear translocation, DNA binding, and the transcription of multiple oncogenes. To date, very few small molecules have been identified as IL-6/gp130 inhibitors. MDL-A is a natural product that was found to specifically interfere with the IL-6/gp130 interaction surface. However, it's no longer produced in nature (due to mutation in the bacterial strain) and synthetic complexity together with its relatively low binding affinity limits its potential as a lead compound. Although some MDL-A analogues were designed and made, their tedious synthesis and relatively weak potency make them less promising. Raloxifene and bazedoxifene were found to be IL-6/gp130 inhibitors, but they are already FDA approved drugs known as selective estrogen receptor modulators (SERMs) used for the treatment of postmenopausal osteoporosis, which may cause side effects when used to treat cancer. SC144 is another potent small molecule found to bind to gp130, but it inhibits both IL-6 and LIF induced STAT3 nuclear translocation, indicating it may not be a specific IL-6/gp130 inhibitor. Therefore, looking for novel small molecule IL-6/gp130 inhibitors with high potency and specificity as anticancer agents is highly desirable.

BRIEF SUMMARY OF THE INVENTION

This invention is directed towards compounds, compositions, and methods of treating disease, disorders and conditions in a subject, including, inflammation, cancer, and autoimmune diseases by use of the compounds and compositions thereof.

It is understood that the embodiments of the invention discussed below with respect to the preferred variable selections can be taken alone or in combination with one or more embodiments, or preferred variable selections, of the invention, as if each combination were explicitly listed herein.

In one aspect, the invention is directed to a compound of Formula (I), or a pharmaceutically acceptable salt, solvate, hydrate or prodrug thereof:

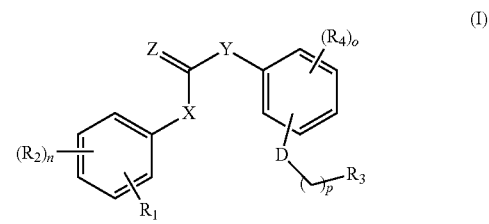

wherein:

$R_1$ is optionally substituted heterocyclyl or optionally substituted heteroaryl;

each $R_2$ is independently halo, cyano, —$OR_5$, $NO_2$, alkyl, haloalkyl, hydroxyalkyl, alkoxyalkyl, or —$NR_6R_7$;

$R_3$ is optionally substituted cycloalkyl, optionally substituted heterocyclyl, or optionally substituted aryl;

each $R_4$ is independently halo, cyano, —$OR_5$, $NO_2$, alkyl, haloalkyl, hydroxyalkyl, alkoxyalkyl, or —$NR_6R_7$;

each $R_5$ is independently hydrogen or optionally substituted alkyl;

each $R_6$ is independently hydrogen or optionally substituted alkyl;

each $R_7$ is independently hydrogen or optionally substituted alkyl;

D is a bond, —O—, —S—, or —N($R_6$)—;

X is —O—, —S—, or —N($R_6$)—;

Y is a bond, —O—, —S—, or —N($R_6$)—;

Z is O, S, or NR$_6$;
n is 0, 1, 2, 3, or 4;
o is 0, 1, 2, 3, or 4; and
p is 0, 1, 2, 3, or 4.

In another aspect, the invention is directed to a compound of Formula (I), or a pharmaceutically acceptable salt, solvate, hydrate or prodrug thereof:

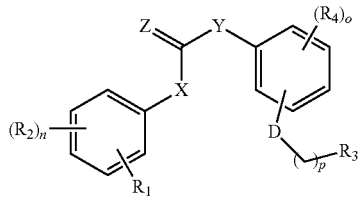
(I)

wherein:

R$_1$ is heterocyclyl or optionally substituted heteroaryl, each optionally substituted with 1, 2, 3, 4, or 5 independent:
a) alkyl (e.g., methyl);
b) oxo;
c) —OR$_5$;
d) halo;
e) —OC(O)R$_5$;
f) —NHC(O)R$_5$; or
g) —NR$_6$R$_7$;

each R$_2$ is independently halo, cyano, —OR$_5$, NO$_2$, alkyl, haloalkyl, hydroxyalkyl, alkoxyalkyl, or —NR$_6$R$_7$;

R$_3$ is optionally substituted cycloalkyl, optionally substituted heterocyclyl, or optionally substituted aryl;

each R$_4$ is independently halo, cyano, —OR$_5$, NO$_2$, alkyl, haloalkyl, hydroxyalkyl, alkoxyalkyl, or —NR$_6$R$_7$;

each R$_5$ is independently hydrogen or optionally substituted alkyl;

each R$_6$ is independently hydrogen or optionally substituted alkyl;

each R$_7$ is independently hydrogen or optionally substituted alkyl;

D is a bond, —O—, —S—, or —N(R$_6$)—;
X is —O—, —S—, or —N(R$_6$)—;
Y is a bond, —O—, —S—, or —N(R$_6$)—;
Z is O, S, or NR$_6$;
n is 0, 1, 2, 3, or 4;
o is 0, 1, 2, 3, or 4; and
p is 0, 1, 2, 3, or 4.

In another aspect, the compound of Formula (I) is a compound of Formula (II), or a pharmaceutically acceptable salt, solvate, hydrate or prodrug thereof:

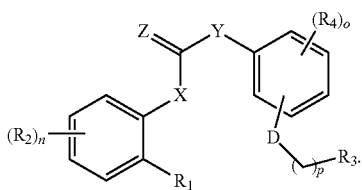
(II)

In another aspect, the compound of Formula (I) is a compound of Formula (III), or a pharmaceutically acceptable salt, solvate, hydrate or prodrug thereof:

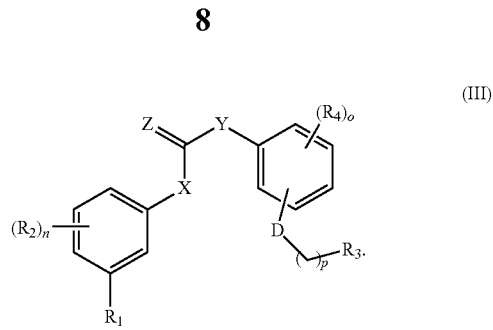
(III)

In another aspect, the compound of Formula (I) is a compound of Formula (IV), or a pharmaceutically acceptable salt, solvate, hydrate or prodrug thereof:

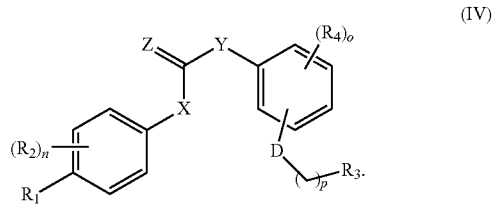
(IV)

In another aspect, the compound of Formula (I) is a compound of Formula (V), or a pharmaceutically acceptable salt, solvate, hydrate or prodrug thereof:

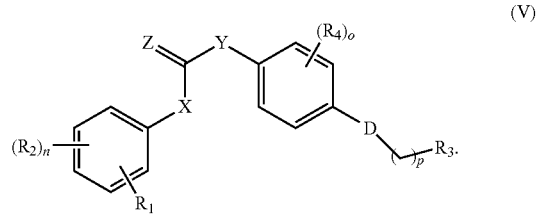
(V)

In another aspect, the compound of Formula (I) is a compound of Formula (VI), or a pharmaceutically acceptable salt, solvate, hydrate or prodrug thereof:

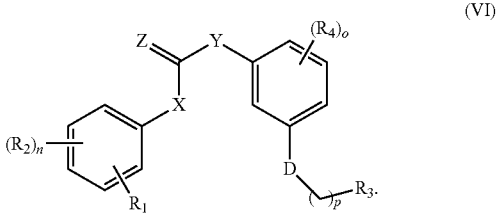
(VI)

In another aspect, the compound of Formula (I) is a compound of Formula (VII), or a pharmaceutically acceptable salt, solvate, hydrate or prodrug thereof:

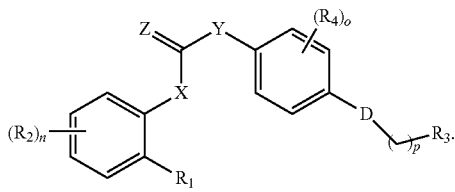
(VII)

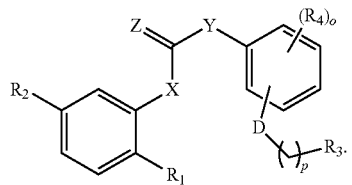
(XI)

In another aspect, the compound of Formula (I) is a compound of Formula (VIII), or a pharmaceutically acceptable salt, solvate, hydrate or prodrug thereof:

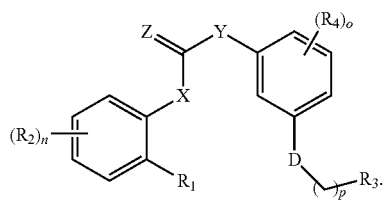
(VIII)

In another aspect, the compound of Formula (I) is a compound of Formula (XII), or a pharmaceutically acceptable salt, solvate, hydrate or prodrug thereof:

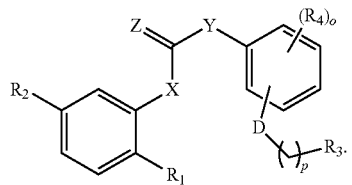
(XII)

In another aspect, the compound of Formula (I) is a compound of Formula (IX), or a pharmaceutically acceptable salt, solvate, hydrate or prodrug thereof:

In another aspect, the compound of Formula (I) is a compound of Formula (XIII), or a pharmaceutically acceptable salt, solvate, hydrate or prodrug thereof:

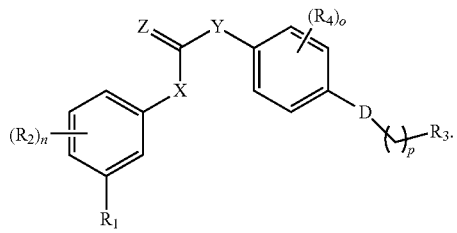
(IX)

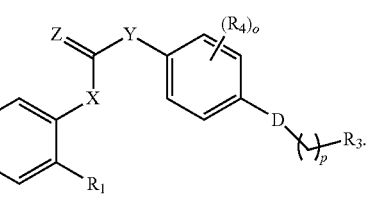
(XIII)

Another aspect is a compound of the formulae herein, wherein X is —NH—.

Another aspect is a compound of the formulae herein, wherein Z is O.

Another aspect is a compound of the formulae herein, wherein Y is a bond or —NR$_6$—.

Another aspect is a compound of the formulae herein, wherein R$_1$ is optionally substituted heteroaryl or heterocycloalkyl. In another aspect, R$_1$ is optionally substituted 5 or 6 membered heteroaryl or heterocycloalkyl. In another aspect, R$_1$ is pyrrolyl, pyrazolyl, imidazolyl, isoxazolyl, oxazolyl, isothiazolyl, thiazolyl, oxadiazolyl, thiadiazolyl, triazolyl, tetrazolyl, oxatriazolyl, pyrazinyl, pyridyl, pyridazinyl, or pyrimidinyl, each of which is optionally substituted.

In another aspect, the compound of Formula (I) is a compound of Formula (X), or a pharmaceutically acceptable salt, solvate, hydrate or prodrug thereof:

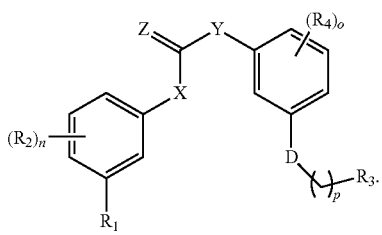
(X)

Another aspect is a compound of the formulae herein, wherein R$_1$ is optionally substituted heteroaryl or heterocycloalkyl. In another aspect, R$_1$ is optionally substituted 5 or 6 membered heteroaryl or heterocycloalkyl. In another aspect, R$_1$ is optionally substituted 8-12 membered bicyclic heteroaryl having 1-6 heteroatoms if bicyclic, said heteroatoms selected from O, N, or S, and the remainder ring atoms being carbon (with appropriate hydrogen atoms unless otherwise indicated). In another aspect, R$_1$ is optionally substituted 7-12 membered bicyclic heterocycloalkyl comprising 1-6 heteroatoms, said heteroatoms selected from O, N, or S. In another aspect, R$_1$ is pyrrolyl, pyrazolyl, imidazolyl, isoxazolyl, oxazolyl, isothiazolyl, thiazolyl, oxadiazolyl, In another aspect, the compound of Formula (I) is a compound of Formula (XI), or a pharmaceutically acceptable salt, solvate, hydrate or prodrug thereof:

thiadiazolyl, triazolyl, tetrazolyl, oxatriazolyl, pyrazinyl, pyridyl, pyridazinyl, pyrimidinyl, azetidinonyl, azetidinethionyl, pyrrolidinonyl, pyrrolidinethionyl, piperidinonyl, piperidinethionyl, tetrahydropyrimidinonyl, tetrahydropyrimidinethionyl, imidazolidinonyl, imidazolidinethionyl, 1,3-diazetidinonyl, 1,3-diazetidinethionyl, 1,2-oxazetidinyle, 1,2-thiazetidinyl, isoxazolidinyl, isothiazolidinyl, 1,2-oxazinanyl, 1,2-thiazinanyl, pyrimidinedionyl, 5-methylpyrimidine-2,4(1H,3H)-dionyl, isoxazol-5(2H)-onyl, 1,7-dihydro-2H-pyrrolo[2,3-d]pyrimidine-2,4(3H)-dionyl, 1,4,5,6-tetrahydro-7H-indol-7-onyl, 1H-pyrrolo[2,3-b]pyridyl, quinazoline-2,4(1H,3H)-dionyl, furo[2,3-d]pyrimidine-2,4 (1H,3H)-dionyl, 1,3-dihydro-2H-benzo[d]imidazol-2-onyl, 1H-indole-4,7-dionyl, 5,6-dimethyl-1H-indole-4,7-dionyl, 5,6-dihydro-1H-indole-4,7-dionyl, 4,5-dihydropyrano[3,4-b]pyrrol-7(1H)-onyl, 1,4,5,6-tetrahydro-7H-pyrrolo[2,3-c]pyridin-7-onyl, 1,6-dihydro-7H-pyrrolo[2,3-c]pyridin-7-onyl, pyrano[3,4-b]pyrrol-7(1H)-onyl, 1,3-dihydro-2H-imidazol-2-onyl, 4-fluoro-1H-pyrazolyl, 3,4-difluoro-1H-pyrazolyl, 3-fluoro-1H-pyrazolyl, 4-chloro-1H-pyrazolyl, 3,4-dichloro-1H-pyrazolyl, 3-chloro-1H-pyrazolyl, 3-methoxy-1H-pyrazolyl, 1H-pyrazol-3-yl acetate, 4-methoxy-1H-pyrazolyl, 1H-pyrazol-4-yl acetate, N-(1H-pyrazol-4-yl)acetamidyl, N,N-dimethyl-1H-pyrazol-4-amino, N,N-dimethyl-1H-pyrazol-3-amino, 4-(trifluoromethyl)-1H-pyrazolyl, 3-(trifluoromethyl)-1H-pyrazolyl, N-(1H-pyrazol-3-yl)acetamide, 1H-pyrazol-3-amino, each of which is optionally substituted.

Another aspect is a compound of the formulae herein, wherein $R_1$ is optionally substituted 5-membered heteroaryl. In another aspect, $R_1$ is optionally substituted pyrrolyl or optionally substituted pyrazolyl. In another aspect, $R_1$ is

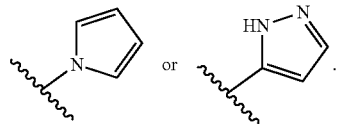 [SMILES: *n1cccc1 ; *c1ccn[nH]1]

In another aspect, $R_1$ is pyrazolyl, dihydropyrazolyl, or pyridazinyl, each of which is optionally substituted.

Another aspect is a compound of the formulae herein, wherein $R_1$ is selected from:

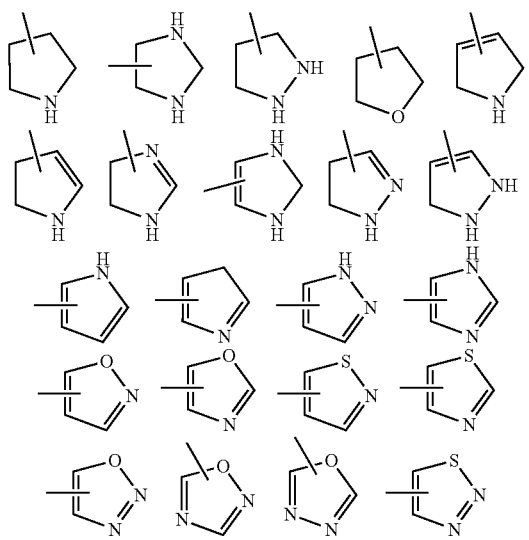

Another aspect is a compound of the formulae herein, wherein $R_1$ is selected from:

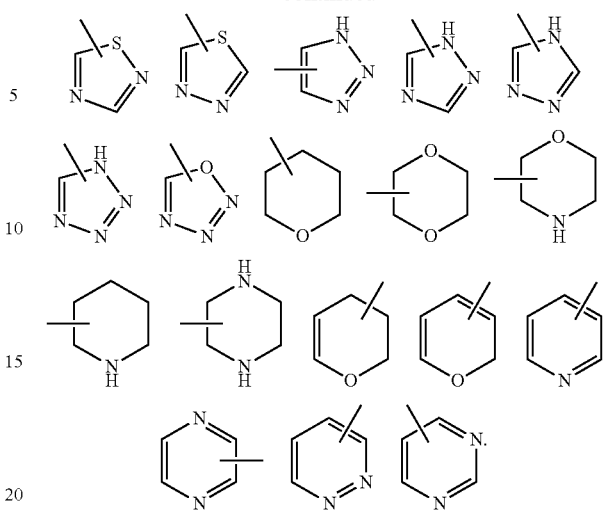

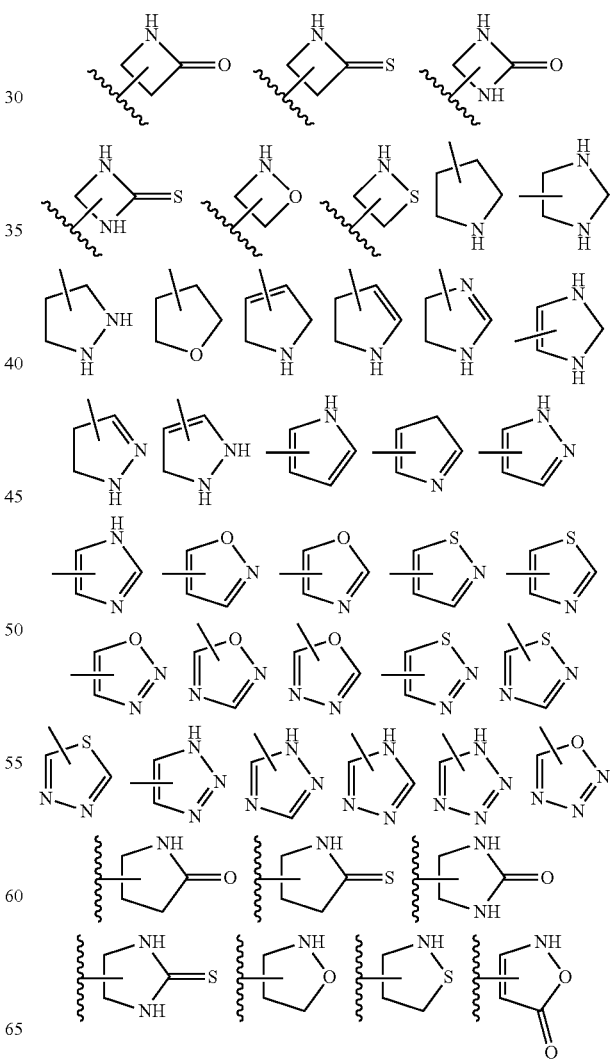

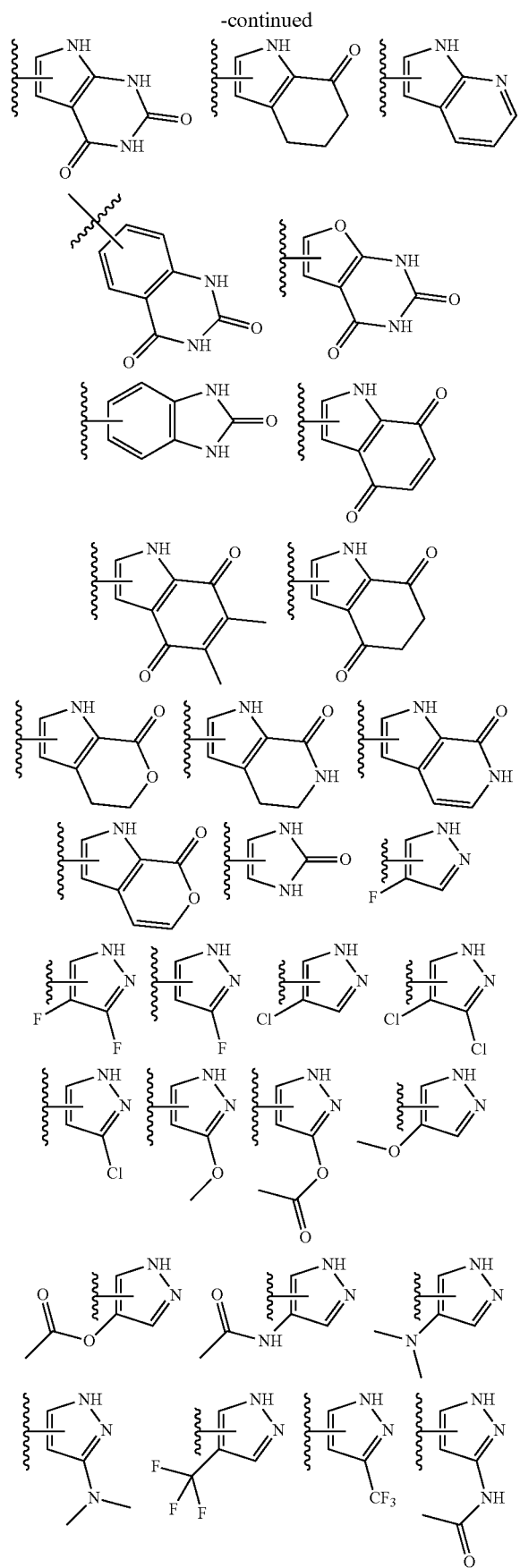
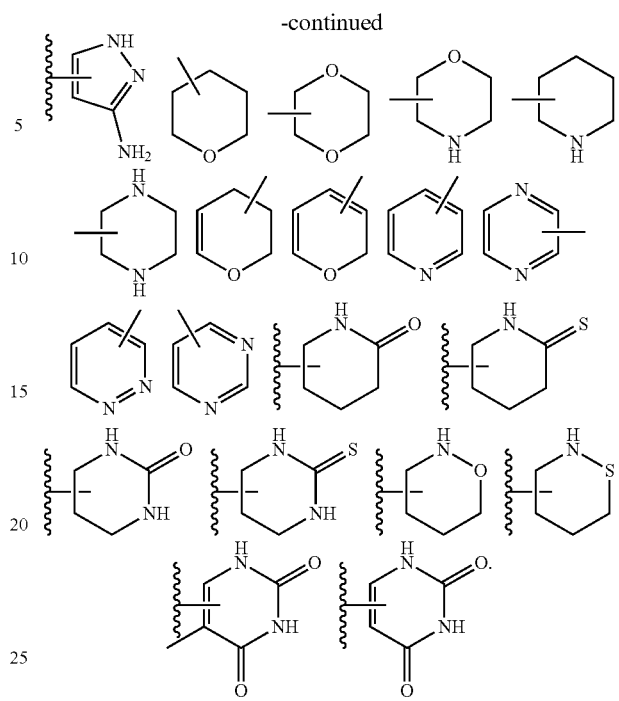

Another aspect is a compound of the formulae herein, wherein $R_3$ is optionally substituted aryl or optionally substituted heterocyclyl. In another aspect, $R_3$ is optionally substituted phenyl or optionally substituted 5-7 membered heterocyclyl. In another aspect, $R_3$ is optionally substituted 6 membered heterocyclyl. In another aspect, $R_3$ is pyrrolidinyl, piperidinyl, azepanyl, tetrahydrofuranyl, tetrahydropyranyl, morpholinyl, or piperazinyl, each of which is optionally substituted (preferably, piperidinyl, tetrahydropyranyl, morpholinyl, or piperazinyl, each of which is optionally substituted; more preferably, optionally substituted piperidinyl). In another aspect, $R_3$ is selected from aziridnyl, azetidinyl, pyrrolidinyl, piperidinyl, azepanyl, and azocanyl, each of which is optionally substituted.

Another aspect is a compound of the formulae herein, wherein $R_3$ is selected from:

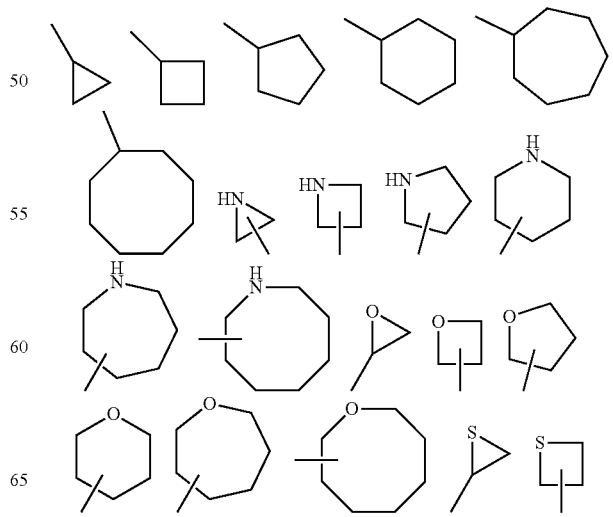

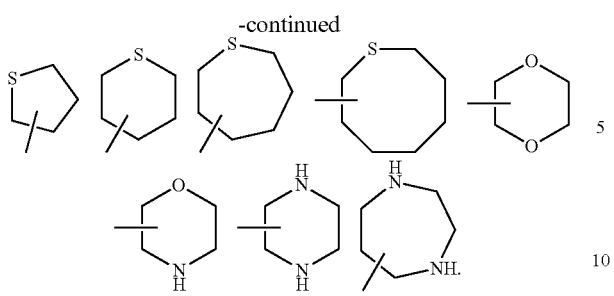

In another aspect, the compound of Formula (I) is a compound of Formula (XIV), or a pharmaceutically acceptable salt, solvate, hydrate or prodrug thereof:

(XIV)

In another aspect, the compound of Formula (I) is a compound of Formula (XV), or a pharmaceutically acceptable salt, solvate, hydrate or prodrug thereof:

(XV)

Another aspect is a compound of Formula (XIV), or a pharmaceutically acceptable salt, solvate, hydrate or prodrug thereof, wherein $R_1$ is optionally substituted heteroaryl. In another aspect, $R_1$ is optionally substituted pyrrolyl or optionally substituted pyrazolyl. In another aspect, $R_1$ is pyrrolyl or pyrazolyl. In another aspect, $R_1$ is

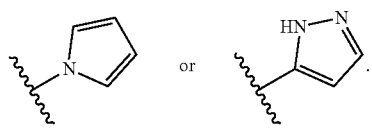 [SMILES: *n1cccc1 ; *c1ccn[nH]1]

Another aspect is a compound of Formula (XV), or a pharmaceutically acceptable salt, solvate, hydrate or prodrug thereof, wherein $R_1$ is optionally substituted heteroaryl. In another aspect, $R_1$ is optionally substituted pyrrolyl or optionally substituted pyrazolyl. In another aspect, $R_1$ is pyrrolyl or pyrazolyl. In another aspect, $R_1$ is

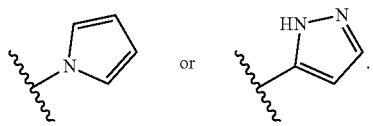 [SMILES: *n1cccc1 ; *c1ccn[nH]1]

Another aspect is a compound of Formula (XIV) or Formula (XV), or a pharmaceutically acceptable salt, solvate, hydrate or prodrug thereof, according to Formula (XVI):

(XVI)

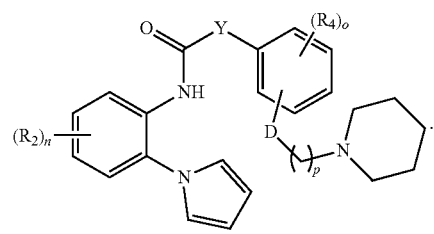

Another aspect is a compound of Formula (XIV) or Formula (XV), or a pharmaceutically acceptable salt, solvate, hydrate or prodrug thereof, according to Formula (XVII):

(XVII)

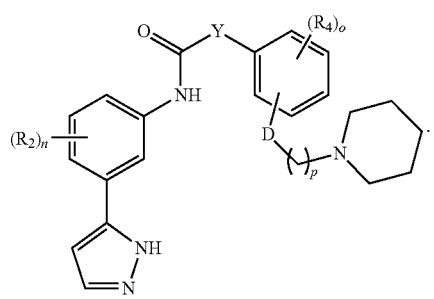

Another aspect is a compound of Formula (XIV) or Formula (XV), or a pharmaceutically acceptable salt, solvate, hydrate or prodrug thereof, according to Formula (XVIII):

(XVIII)

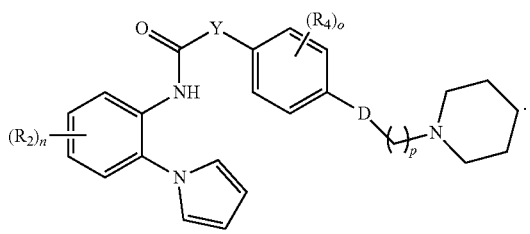

Another aspect is a compound of Formula (XIV) or Formula (XV), or a pharmaceutically acceptable salt, solvate, hydrate or prodrug thereof, according to Formula (XIX):

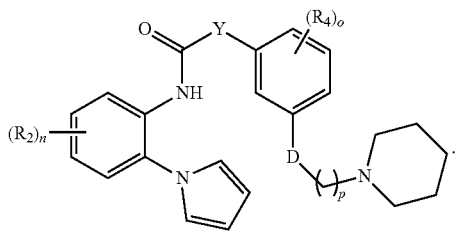

(XIX)

Another aspect is a compound of Formula (XIV) or Formula (XV), or a pharmaceutically acceptable salt, solvate, hydrate or prodrug thereof, according to Formula (XX):

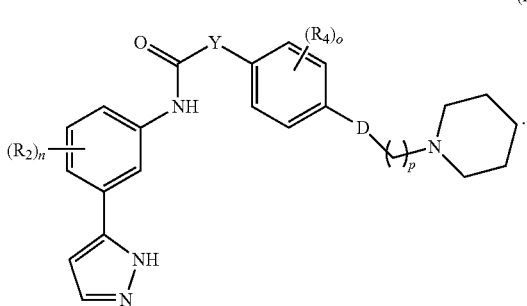

(XX)

Another aspect is a compound of Formula (XIV) or Formula (XV), or a pharmaceutically acceptable salt, solvate, hydrate or prodrug thereof, according to Formula (XXI):

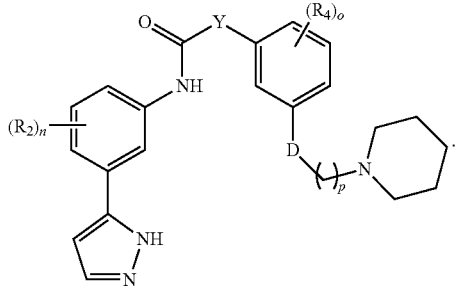

(XXI)

Another aspect is a compound of any of Formulae (XIV)-(XXI), wherein Y is a bond or —NR$_6$—.

Another aspect is a compound of any of Formulae (XIV)-(XXI), wherein Y is a bond.

Another aspect is a compound of any of Formulae (XIV)-(XXI), wherein Y is —NH—.

Another aspect is a compound of the formulae herein, wherein the compound is selected from:

N-(5-fluoro-2-(1H-pyrrol-1-yl)phenyl)-4-(2-(piperidin-1-yl)ethoxy)benzamide (LLM3);
N-(5-fluoro-2-(1H-pyrrol-1-yl)phenyl)-4-(3-(piperidin-1-yl)propoxy)benzamide (LLM4);
N-(5-fluoro-2-(1H-pyrrol-1-yl)phenyl)-4-phenethoxybenzamide (LLM5);
N-(5-fluoro-2-(1H-pyrrol-1-yl)phenyl)-4-(3-phenylpropoxy)benzamide (LLM6);
N-(5-fluoro-2-(1H-pyrrol-1-yl)phenyl)-4-(4-phenylbutoxy)benzamide (LLM7);
N-(3-(1H-pyrazol-5-yl)phenyl)-4-(3-(piperidin-1-yl)propoxy)benzamide (LLM41);
N-(3-(1H-pyrazol-5-yl)phenyl)-4-(2-(piperidin-1-yl)ethoxy)benzamide (LLM42);
N-(3-(1H-pyrazol-5-yl)phenyl)-3-(3-(piperidin-1-yl)propoxy)benzamide (LLM45);
N-(3-(1H-pyrazol-5-yl)phenyl)-3-(2-(piperidin-1-yl)ethoxy)benzamide (LLM46);
1-(3-(1H-pyrazol-5-yl)phenyl)-3-(3-(3-(piperidin-1-yl)propoxy)phenyl)urea (LLM413);
1-(3-(1H-pyrazol-5-yl)phenyl)-3-(3-(2-(piperidin-1-yl)ethoxy)phenyl)urea (LLM414);
N-(2-(1H-pyrazol-5-yl)phenyl)-4-(3-(piperidin-1-yl)propoxy)benzamide (LLM417);
N-(2-(1H-pyrazol-5-yl)phenyl)-4-(2-(piperidin-1-yl)ethoxy)benzamide (LLM418);
N-(3-(1H-pyrazol-5-yl)phenyl)-3-(piperidin-1-yl)benzamide (LLM437);
N-(3-(1H-pyrazol-5-yl)phenyl)-3-(piperidin-1-ylmethyl)benzamide (LLM438);
or a pharmaceutically acceptable salt, solvate, hydrate or prodrug thereof.

Another aspect is a compound of the formulae herein, wherein the compound is selected from:

N-(5-fluoro-2-(1H-pyrrol-1-yl)phenyl)-4-(2-(piperidin-1-yl)ethoxy)benzamide (LLM3);
N-(5-fluoro-2-(1H-pyrrol-1-yl)phenyl)-4-(3-(piperidin-1-yl)propoxy)benzamide (LLM4);
N-(5-fluoro-2-(1H-pyrrol-1-yl)phenyl)-4-phenethoxybenzamide (LLM5);
N-(5-fluoro-2-(1H-pyrrol-1-yl)phenyl)-4-(3-phenylpropoxy)benzamide (LLM6);
N-(5-fluoro-2-(1H-pyrrol-1-yl)phenyl)-4-(4-phenylbutoxy)benzamide (LLM7);
N-(3-(1H-pyrazol-5-yl)phenyl)-4-(3-(piperidin-1-yl)propoxy)benzamide (LLM41);
N-(3-(1H-pyrazol-5-yl)phenyl)-4-(2-(piperidin-1-yl)ethoxy)benzamide (LLM42);
N-(3-(1H-pyrazol-5-yl)phenyl)-3-(3-(piperidin-1-yl)propoxy)benzamide (LLM45);
N-(3-(1H-pyrazol-5-yl)phenyl)-3-(2-(piperidin-1-yl)ethoxy)benzamide (LLM46);
1-(3-(1H-pyrazol-5-yl)phenyl)-3-(3-(3-(piperidin-1-yl)propoxy)phenyl)urea (LLM413);
1-(3-(1H-pyrazol-5-yl)phenyl)-3-(3-(2-(piperidin-1-yl)ethoxy)phenyl)urea (LLM414);
N-(2-(1H-pyrazol-5-yl)phenyl)-4-(3-(piperidin-1-yl)propoxy)benzamide (LLM417);
N-(2-(1H-pyrazol-5-yl)phenyl)-4-(2-(piperidin-1-yl)ethoxy)benzamide (LLM418);
N-(3-(1H-pyrazol-5-yl)phenyl)-3-(piperidin-1-yl)benzamide (LLM437);
N-(3-(1H-pyrazol-5-yl)phenyl)-3-(piperidin-1-ylmethyl)benzamide (LLM438);
N-(2-(4-oxoazetidin-2-yl)phenyl)-4-(2-(piperidin-1-yl)ethoxy)benzamide;
4-(2-(piperidin-1-yl)ethoxy)-N-(2-(4-thioxoazetidin-2-yl)phenyl)benzamide;
N-(2-(5-oxopyrrolidin-2-yl)phenyl)-4-(2-(piperidin-1-yl)ethoxy)benzamide;
4-(2-(piperidin-1-yl)ethoxy)-N-(2-(5-thioxopyrrolidin-2-yl)phenyl)benzamide;
N-(2-(6-oxopiperidin-2-yl)phenyl)-4-(2-(piperidin-1-yl)ethoxy)benzamide;

4-(2-(piperidin-1-yl)ethoxy)-N-(2-(6-thioxopiperidin-2-yl)phenyl)benzamide;
N-(2-(2-oxohexahydropyrimidin-4-yl)phenyl)-4-(2-(piperidin-1-yl)ethoxy)benzamide;
4-(2-(piperidin-1-yl)ethoxy)-N-(2-(2-thioxohexahydropyrimidin-4-yl)phenyl)benzamide;
N-(2-(2-oxoimidazolidin-4-yl)phenyl)-4-(2-(piperidin-1-yl)ethoxy)benzamide;
4-(2-(piperidin-1-yl)ethoxy)-N-(2-(2-thioxoimidazolidin-4-yl)phenyl)benzamide;
N-(2-(4-oxo-1,3-diazetidin-2-yl)phenyl)-4-(2-(piperidin-1-yl)ethoxy)benzamide;
4-(2-(piperidin-1-yl)ethoxy)-N-(2-(4-thioxo-1,3-diazetidin-2-yl)phenyl)benzamide;
N-(2-(1,2-oxazetidin-3-yl)phenyl)-4-(2-(piperidin-1-yl)ethoxy)benzamide;
N-(2-(1,2-thiazetidin-3-yl)phenyl)-4-(2-(piperidin-1-yl)ethoxy)benzamide;
N-(2-(isoxazolidin-3-yl)phenyl)-4-(2-(piperidin-1-yl)ethoxy)benzamide;
N-(2-(isothiazolidin-3-yl)phenyl)-4-(2-(piperidin-1-yl)ethoxy)benzamide;
N-(2-(1,2-oxazinan-3-yl)phenyl)-4-(2-(piperidin-1-yl)ethoxy)benzamide;
N-(2-(1,2-thiazinan-3-yl)phenyl)-4-(2-(piperidin-1-yl)ethoxy)benzamide;
N-(2-(5-methyl-2,6-dioxo-1,2,3,6-tetrahydropyrimidin-4-yl)phenyl)-4-(2-(piperidin-1-yl)ethoxy)benzamide;
N-(2-(2,6-dioxo-1,2,3,6-tetrahydropyrimidin-4-yl)phenyl)-4-(2-(piperidin-1-yl)ethoxy)benzamide;
N-(2-(5-oxopyrrolidin-3-yl)phenyl)-4-(2-(piperidin-1-yl)ethoxy)benzamide;
4-(2-(piperidin-1-yl)ethoxy)-N-(2-(5-thioxopyrrolidin-3-yl)phenyl)benzamide;
N-(2-(6-oxopiperidin-3-yl)phenyl)-4-(2-(piperidin-1-yl)ethoxy)benzamide;
4-(2-(piperidin-1-yl)ethoxy)-N-(2-(6-thioxopiperidin-3-yl)phenyl)benzamide;
N-(2-(5-oxo-2,5-dihydroisoxazol-3-yl)phenyl)-4-(2-(piperidin-1-yl)ethoxy)benzamide;
N-(3-(2,4-dioxo-1,2,3,4-tetrahydro-7H-pyrrolo[2,3-d]pyrimidin-7-yl)phenyl)-4-(2-(piperidin-1-yl)ethoxy)benzamide;
N-(2-(7-oxo-4,5,6,7-tetrahydro-1H-indol-2-yl)phenyl)-4-(2-(piperidin-1-yl)ethoxy)benzamide;
N-(2-(1H-pyrrolo[2,3-b]pyridin-2-yl)phenyl)-4-(2-(piperidin-1-yl)ethoxy)benzamide;
N-(3-(2,4-dioxo-1,2,3,4-tetrahydroquinazolin-8-yl)phenyl)-4-(2-(piperidin-1-yl)ethoxy)benzamide;
N-(3-(2,4-dioxo-1,2,3,4-tetrahydrofuro[3,2-d]pyrimidin-7-yl)phenyl)-4-(2-(piperidin-1-yl)ethoxy)benzamide;
N-(3-(2-oxo-2,3-dihydro-1H-benzo[d]imidazol-4-yl)phenyl)-4-(2-(piperidin-1-yl)ethoxy)benzamide;
N-(2-(4,7-dioxo-4,7-dihydro-1H-indol-3-yl)phenyl)-4-(2-(piperidin-1-yl)ethoxy)benzamide;
N-(2-(5,6-dimethyl-4,7-dioxo-4,7-dihydro-1H-indol-3-yl)phenyl)-4-(2-(piperidin-1-yl)ethoxy)benzamide;
N-(2-(7-oxo-4,5,6,7-tetrahydro-1H-indol-3-yl)phenyl)-4-(2-(piperidin-1-yl)ethoxy)benzamide;
N-(2-(4,7-dioxo-4,5,6,7-tetrahydro-1H-indol-3-yl)phenyl)-4-(2-(piperidin-1-yl)ethoxy)benzamide;
N-(2-(7-oxo-1,4,5,7-tetrahydropyrano[3,4-b]pyrrol-3-yl)phenyl)-4-(2-(piperidin-1-yl)ethoxy)benzamide;
N-(2-(7-oxo-4,5,6,7-tetrahydro-1H-pyrrolo[2,3-c]pyridin-3-yl)phenyl)-4-(2-(piperidin-1-yl)ethoxy)benzamide;
N-(2-(7-oxo-6,7-dihydro-1H-pyrrolo[2,3-c]pyridin-3-yl)phenyl)-4-(2-(piperidin-1-yl)ethoxy)benzamide;
N-(2-(7-oxo-1,7-dihydropyrano[3,4-b]pyrrol-3-yl)phenyl)-4-(2-(piperidin-1-yl)ethoxy)benzamide;
N-(2-(2-oxo-2,3-dihydro-1H-imidazol-4-yl)phenyl)-4-(2-(piperidin-1-yl)ethoxy)benzamide;
1-(2-(1H-pyrazol-5-yl)phenyl)-3-(3-(2-(piperidin-1-yl)ethoxy)phenyl)urea;
1-(2-(5-methyl-2,6-dioxo-1,2,3,6-tetrahydropyrimidin-4-yl)phenyl)-3-(3-(2-(piperidin-1-yl)ethoxy)phenyl)urea;
1-(2-(2,6-dioxo-1,2,3,6-tetrahydropyrimidin-4-yl)phenyl)-3-(3-(2-(piperidin-1-yl)ethoxy)phenyl)urea;
1-(2-(1H-pyrazol-5-yl)phenyl)-3-(4-(2-(piperidin-1-yl)ethoxy)phenyl)urea;
N-(2-(4-fluoro-1H-pyrazol-5-yl)phenyl)-4-(2-(piperidin-1-yl)ethoxy)benzamide;
N-(2-(3,4-difluoro-1H-pyrazol-5-yl)phenyl)-4-(2-(piperidin-1-yl)ethoxy)benzamide;
N-(2-(3-fluoro-1H-pyrazol-5-yl)phenyl)-4-(2-(piperidin-1-yl)ethoxy)benzamide;
N-(2-(4-chloro-1H-pyrazol-5-yl)phenyl)-4-(2-(piperidin-1-yl)ethoxy)benzamide;
N-(2-(3,4-dichloro-1H-pyrazol-5-yl)phenyl)-4-(2-(piperidin-1-yl)ethoxy)benzamide;
N-(2-(3-chloro-1H-pyrazol-5-yl)phenyl)-4-(2-(piperidin-1-yl)ethoxy)benzamide;
N-(2-(3-methoxy-1H-pyrazol-5-yl)phenyl)-4-(2-(piperidin-1-yl)ethoxy)benzamide;
5-(2-(4-(2-(piperidin-1-yl)ethoxy)benzamido)phenyl)-1H-pyrazol-3-yl acetate;
N-(2-(4-methoxy-1H-pyrazol-5-yl)phenyl)-4-(2-(piperidin-1-yl)ethoxy)benzamide;
5-(2-(4-(2-(piperidin-1-yl)ethoxy)benzamido)phenyl)-1H-pyrazol-4-yl acetate;
N-(2-(4-acetamido-1H-pyrazol-5-yl)phenyl)-4-(2-(piperidin-1-yl)ethoxy)benzamide;
N-(2-(4-(dimethylamino)-1H-pyrazol-5-yl)phenyl)-4-(2-(piperidin-1-yl)ethoxy)benzamide;
N-(2-(3-(dimethylamino)-1H-pyrazol-5-yl)phenyl)-4-(2-(piperidin-1-yl)ethoxy)benzamide;
N-(4-methyl-2-(1H-pyrazol-5-yl)phenyl)-4-(2-(piperidin-1-yl)ethoxy)benzamide;
N-(4,5-dimethoxy-2-(1H-pyrazol-5-yl)phenyl)-4-(2-(piperidin-1-yl)ethoxy)benzamide;
N-(4,5-dihydroxy-2-(1H-pyrazol-5-yl)phenyl)-4-(2-(piperidin-1-yl)ethoxy)benzamide;
N-(5-bromo-2-(1H-pyrazol-5-yl)phenyl)-4-(2-(piperidin-1-yl)ethoxy)benzamide;
4-(2-(piperidin-1-yl)ethoxy)-N-(2-(4-(trifluoromethyl)-1H-pyrazol-5-yl)phenyl)benzamide;
4-(2-(piperidin-1-yl)ethoxy)-N-(2-(3-(trifluoromethyl)-1H-pyrazol-5-yl)phenyl)benzamide;
N-(3,5-dibromo-2-(1H-pyrazol-5-yl)phenyl)-4-(2-(piperidin-1-yl)ethoxy)benzamide;
N-(3-bromo-2-(1H-pyrazol-5-yl)phenyl)-4-(2-(piperidin-1-yl)ethoxy)benzamide;
N-(2-(3-acetamido-1H-pyrazol-5-yl)phenyl)-4-(2-(piperidin-1-yl)ethoxy)benzamide;
N-(2-(3-amino-1H-pyrazol-5-yl)phenyl)-4-(2-(piperidin-1-yl)ethoxy)benzamide;
or a pharmaceutically acceptable salt, solvate, hydrate or prodrug thereof.

Another aspect is a compound of the formulae herein, wherein the compound is selected from:
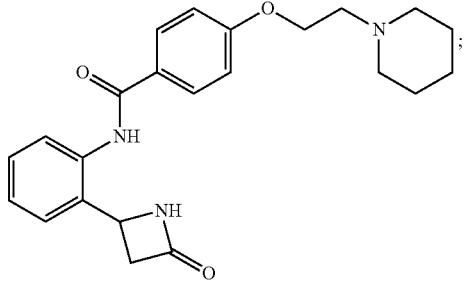
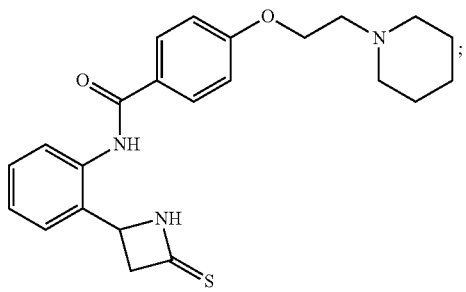
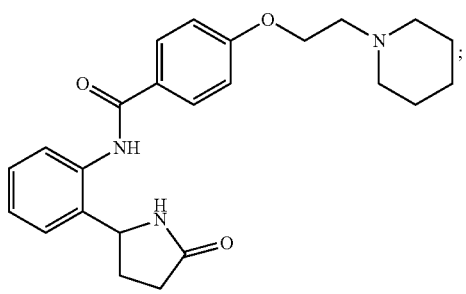
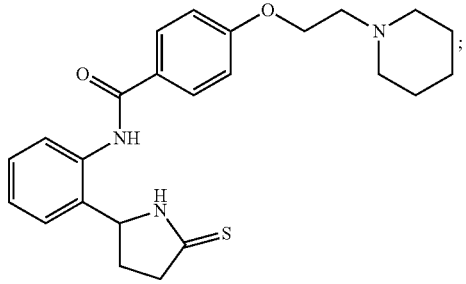
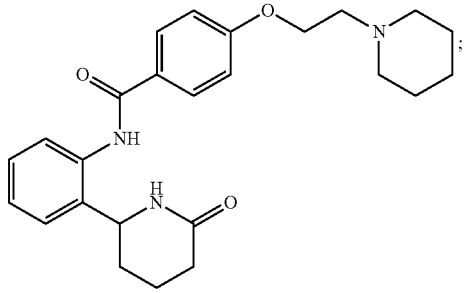
-continued
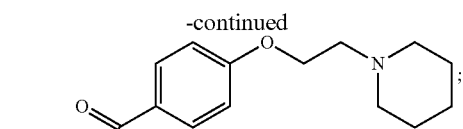
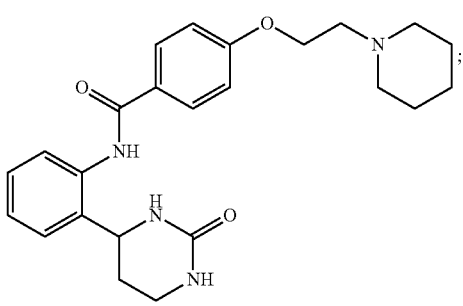
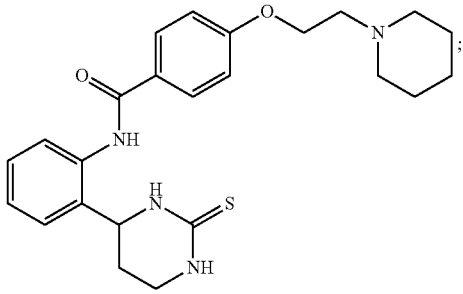
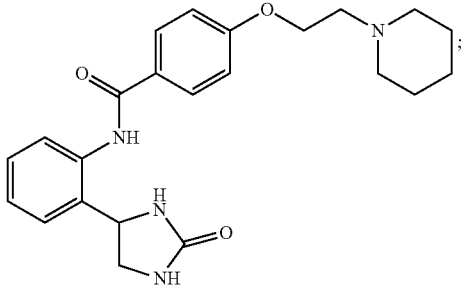
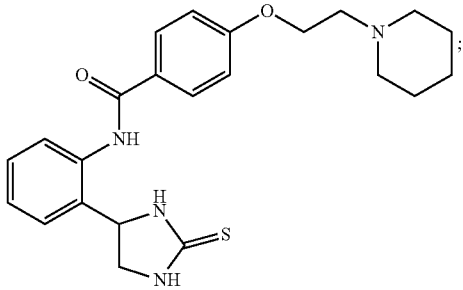

23 -continued

24 -continued

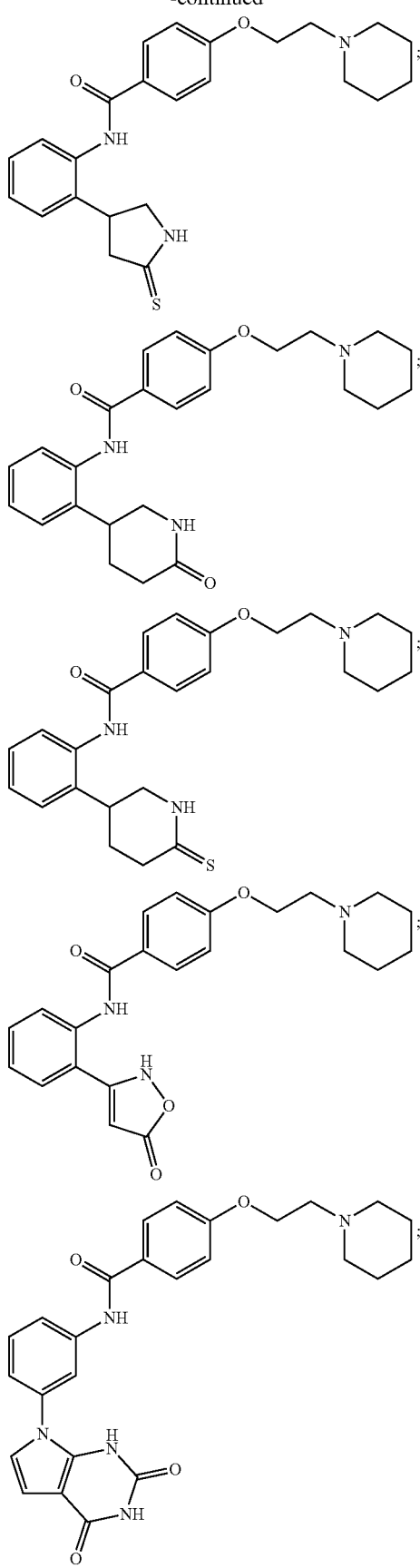
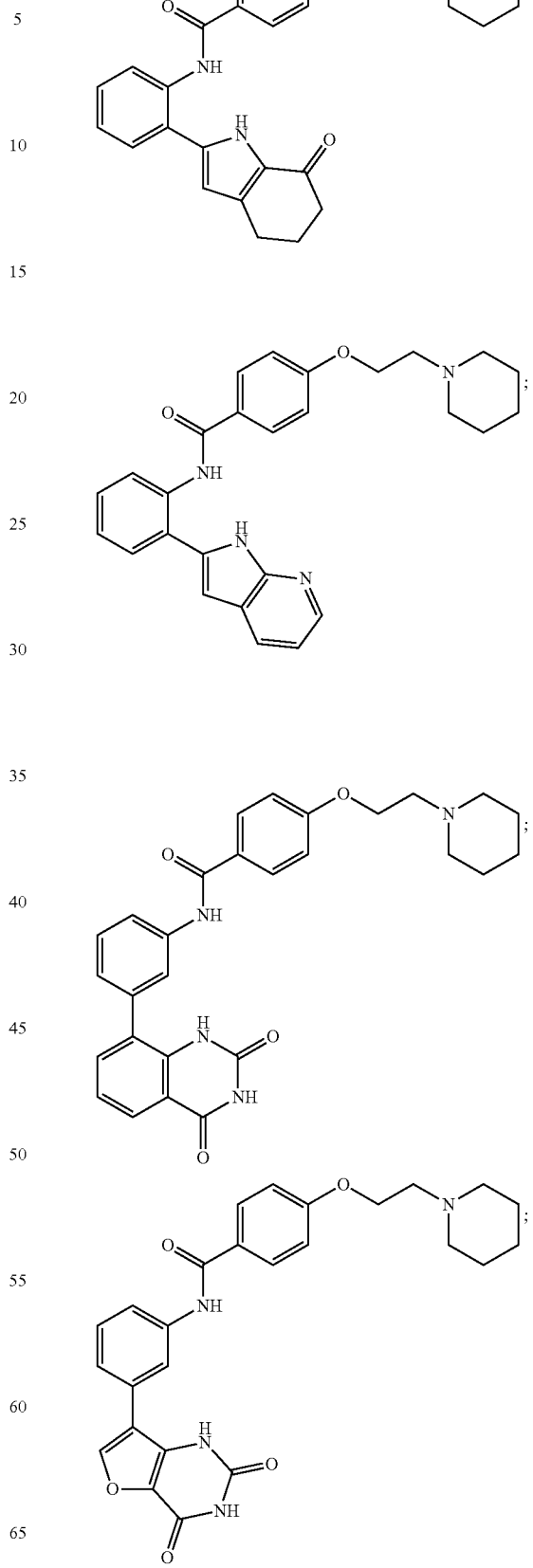

27
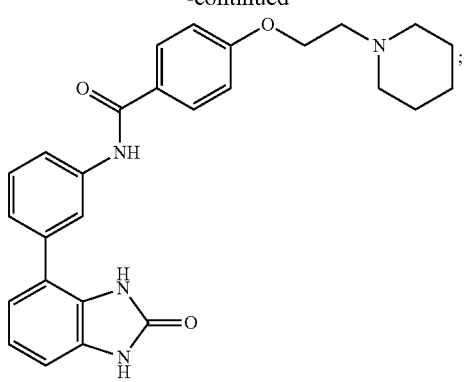
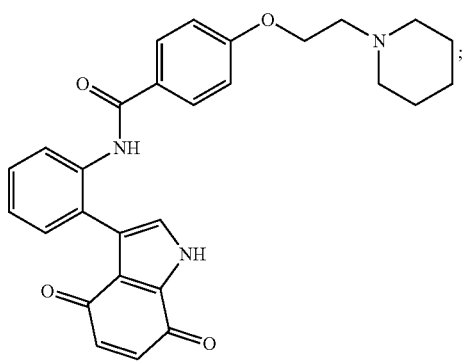
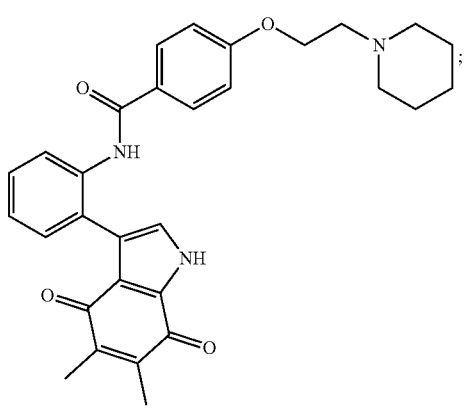
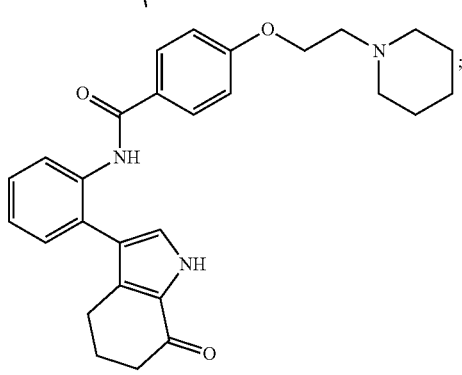
28
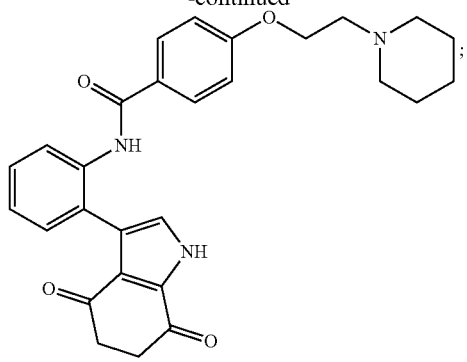
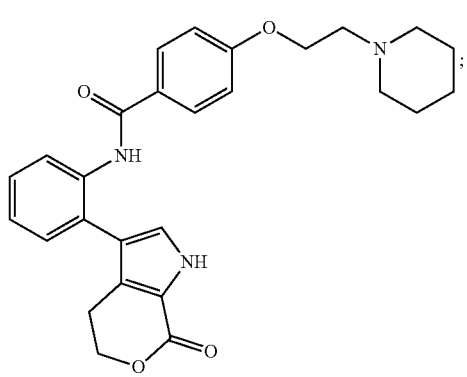
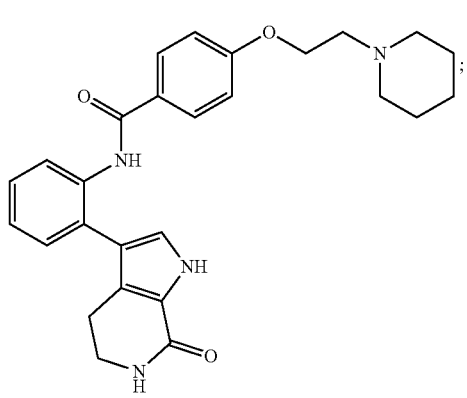
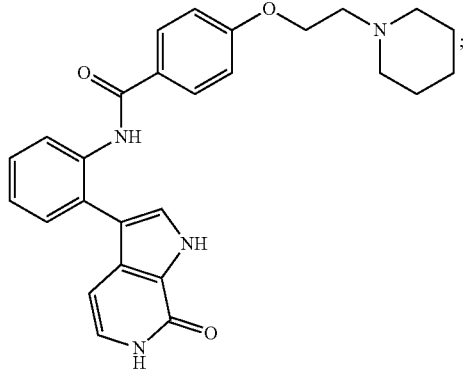

29
-continued
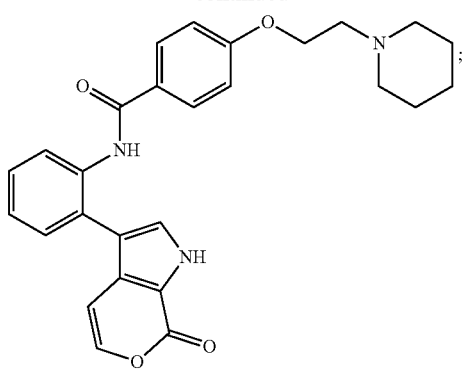
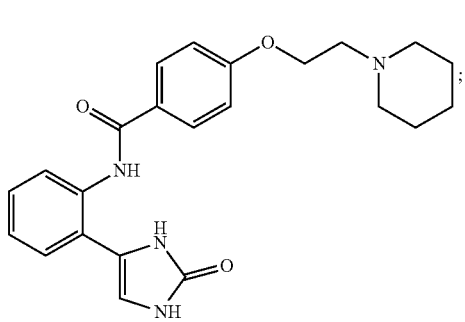
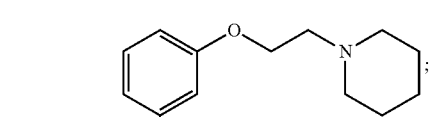
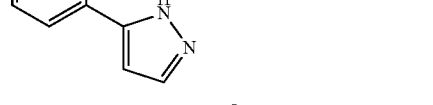
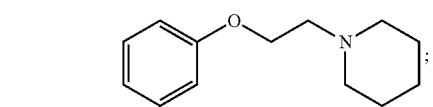
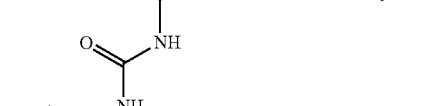
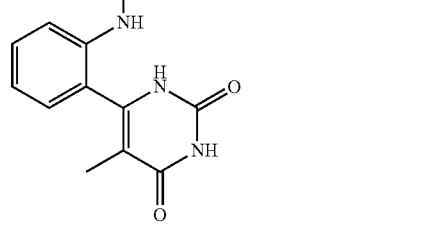
30
-continued
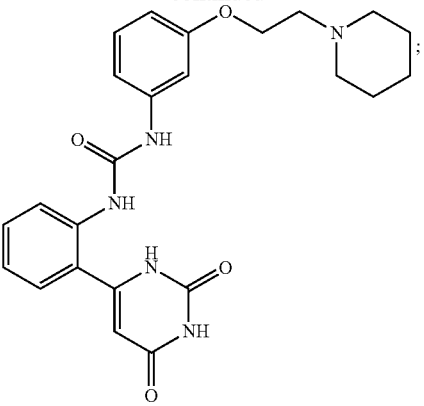
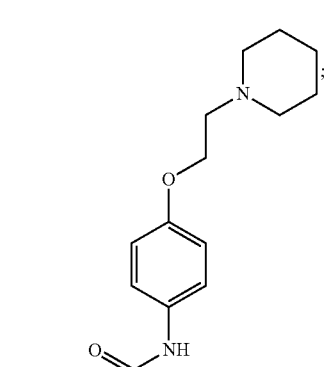
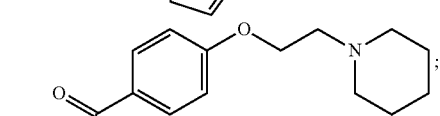
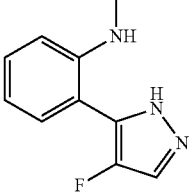
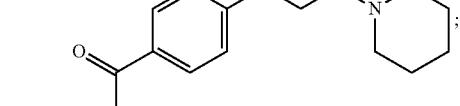
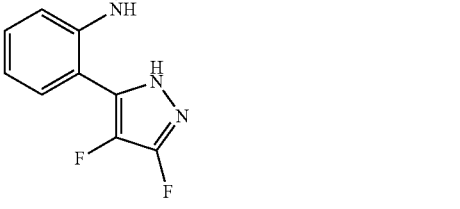

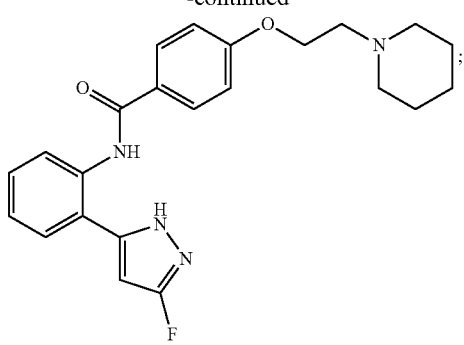
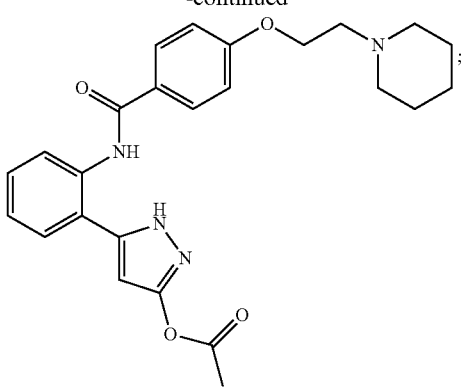
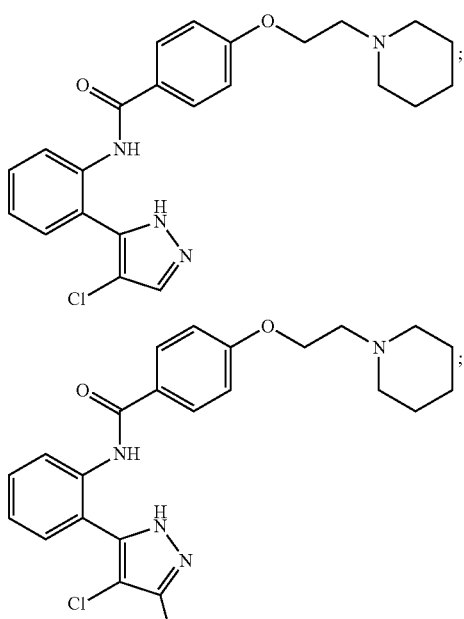
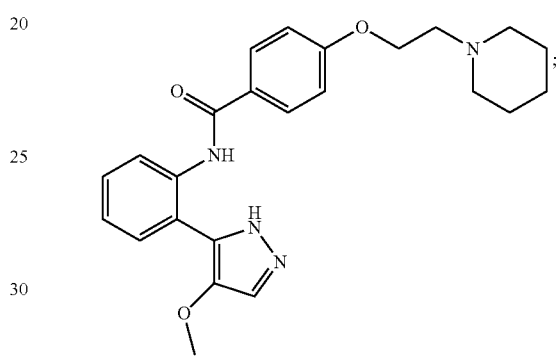
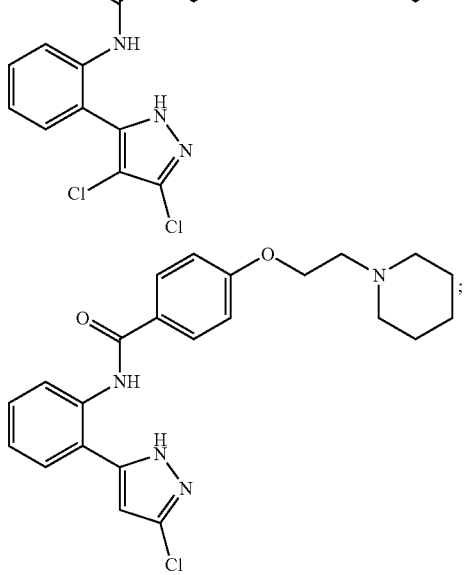
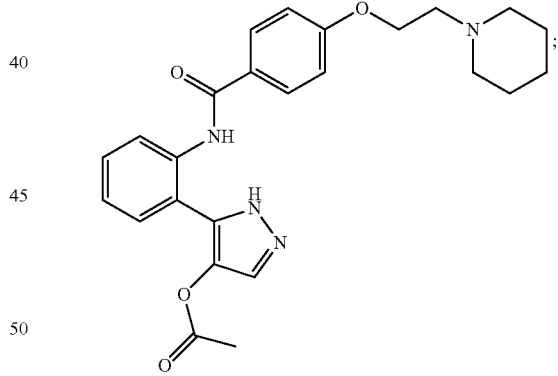
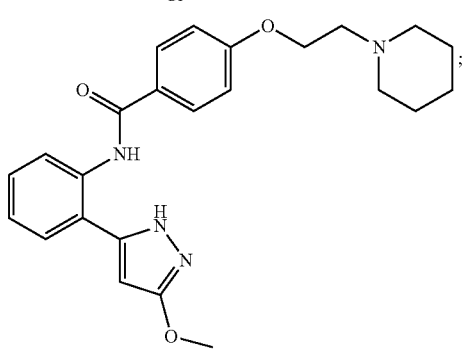
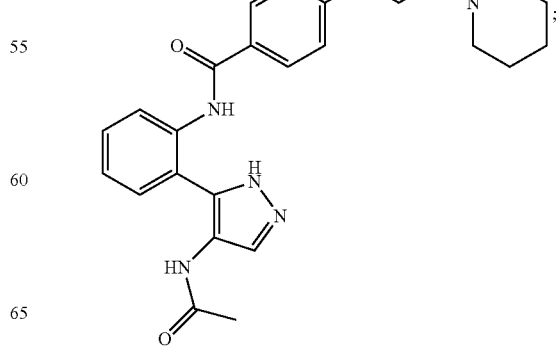

33
-continued
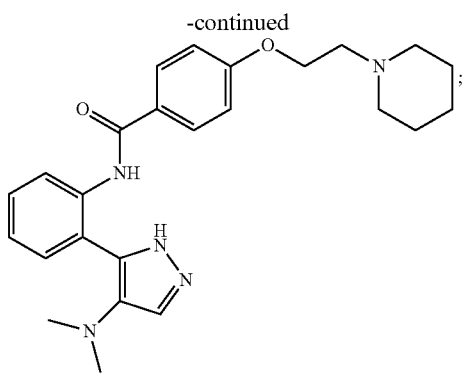
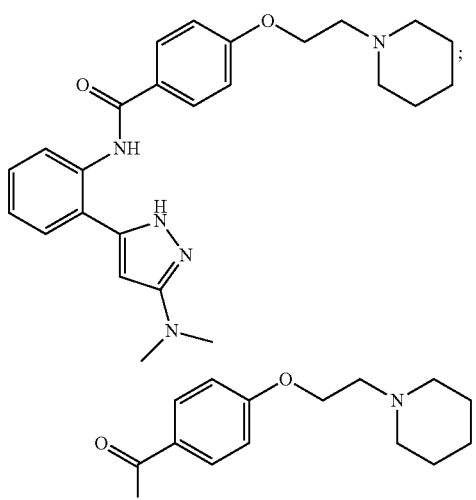
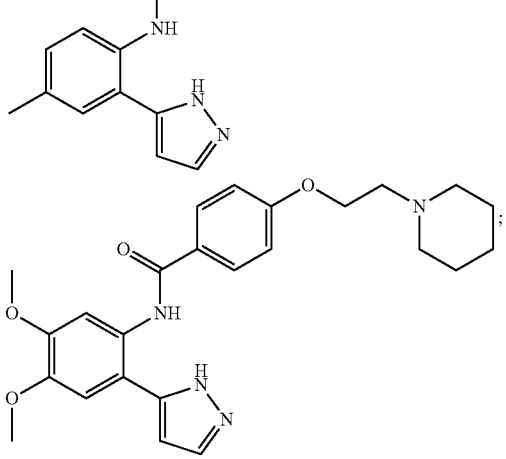
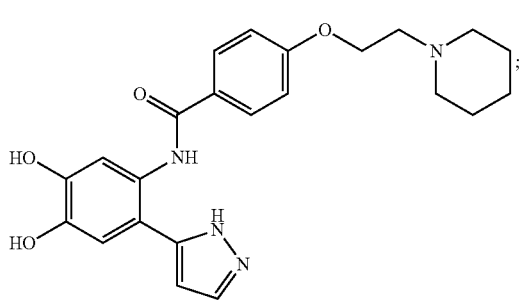
34
-continued
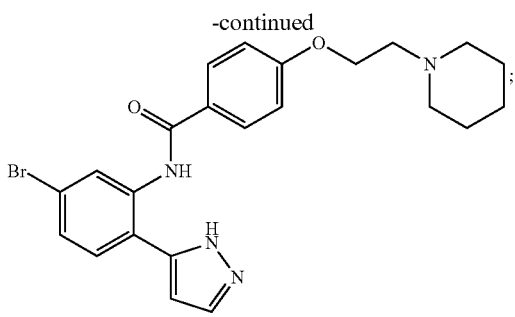
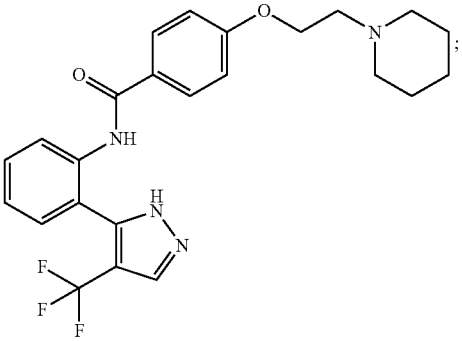
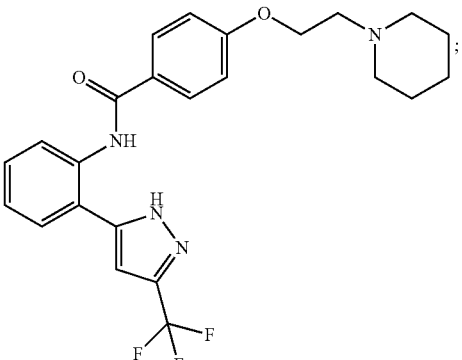
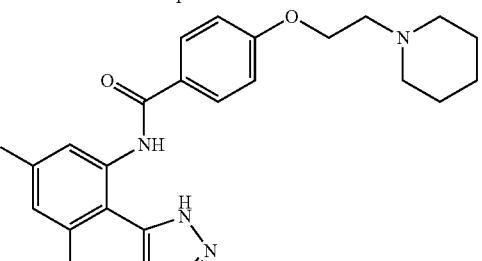
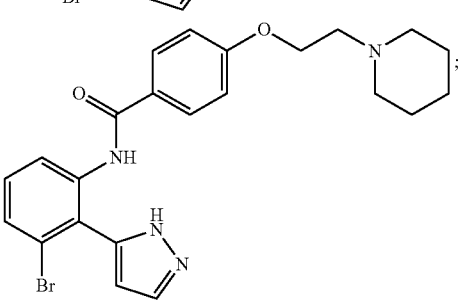

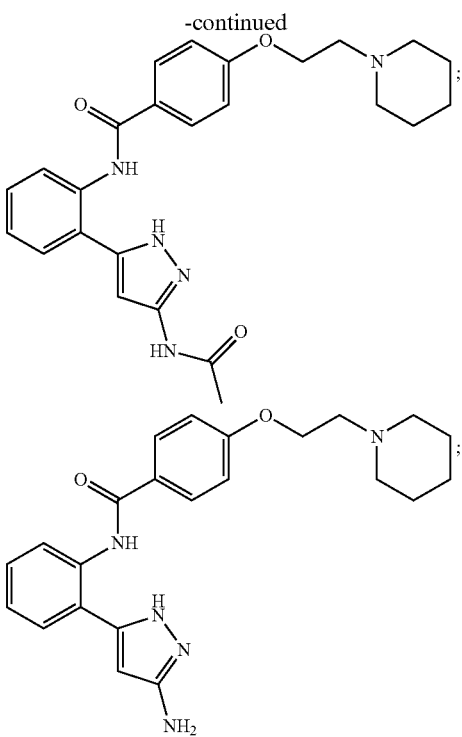

or a pharmaceutically acceptable salt, solvate, hydrate or prodrug thereof.

In another aspect, the invention provides a pharmaceutical composition comprising the compound of any of the formulae herein (e.g., formulae (I)-(XXI)), or a pharmaceutically acceptable salt, solvate, hydrate or prodrug thereof, and a pharmaceutically acceptable carrier. In another aspect, the pharmaceutical composition further comprises an additional therapeutic agent (e.g., an anticancer agent).

In other aspects, the invention provides a method of treating a disease, disorder, or symptom thereof in a subject, comprising administering to the subject any compound or composition delineated herein. In another aspect, the compound or composition is administered in an amount and under conditions sufficient to ameliorate the disease, disorder, or symptom thereof in a subject.

In another aspect, the disease, disorder, or symptom includes proliferative diseases and disorders, autoimmune disorders (e.g., multiple sclerosis, rheumatoid arthritis, giant cell arteritis, etc.), inflammation, cancer, Alzheimer's disease and other neurodegenerative disorders, stroke, chronic kidney disease, type II diabetes, cancer, tumor growth, cancer of the colon, breast, bone, brain and others (e.g., osteosarcoma, neuroblastoma, colon adenocarcinoma), cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, cutaneous T-cell lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma). Other diseases and disorders that can be treated include the treatment of inflammatory disorders, neurodegenerative diseases, protozoal and latent viral infections, and (fibro)proliferative disorders, and aging itself.

In another aspect, the invention provides a method of inhibiting IL-6 signaling comprising administering a compound of any of the formulae herein (e.g., formulae (I)-(XXI)), or a pharmaceutically acceptable salt, solvate, hydrate or prodrug thereof. In another aspect, the inhibition of IL-6 is in vitro. In another aspect, the inhibition of IL-6 is in vivo. In another aspect, the method of inhibition of IL-6 further comprises administering the compound, or a pharmaceutically acceptable salt, solvate, hydrate or prodrug thereof, to a subject.

In another aspect, the invention provides a method of inhibiting IL-6/gp130 comprising administering a compound of any of the formulae herein (e.g., formulae (I)-(XXI)), or a pharmaceutically acceptable salt, solvate, hydrate or prodrug thereof. In another aspect, the inhibition is in vitro. In another aspect, the inhibition is in vivo. In another aspect, the method further comprises administering the compound, or a pharmaceutically acceptable salt, solvate, hydrate or prodrug thereof, to a subject.

In another aspect, the invention provides a method of inhibiting the formation of the dimerization of two of the IL-6/IL-6Rα/gp130 trimers comprising administering a compound of any of the formulae herein (e.g., formulae (I)-(XXI)), or a pharmaceutically acceptable salt, solvate, hydrate or prodrug thereof. In another aspect, the inhibition is in vitro. In another aspect, the inhibition is in vivo. In another aspect, the method further comprises administering the compound, or a pharmaceutically acceptable salt, solvate, hydrate or prodrug thereof, to a subject.

As discussed above, the homodimerization of IL-ML-#Rα/gp130 trimers is unique to IL-6 and IL-11 among the other IL family members. Also, as discussed above, the IL-NIL-#Rα/gp130 trimers possess beneficial biological functions unrelated to inflammation, autoimmune disorders, or cancer and, thus, it is preferable to inhibit homodimerization of IL-ML-#Rα/gp130 trimers to the corresponding hexamer without disrupting the formation of or biological activity of the corresponding IL-ML-#Rα/gp130 trimer. This selective inhibition of homodimerization of IL-ML-#Rα/gp130 trimers relative to the inhibition of the formation or biological activity of the corresponding IL-NIL-#Rα/gp130 trimer is believed to result in an improved side effect profile (e.g., minimizing or avoiding immunosuppressive effects or immune-related side effects). Thus, one aspect of the invention is a method of selectively inhibiting the homodimerization of IL-6/IL-6Rα/gp130 trimers relative to the inhibition of the formation or biological activity of the corresponding IL-6/IL-6Rα/gp130 trimer, the method comprising administering a compound of any of the formulae herein (e.g., formulae (I)-(XXI)), or a pharmaceutically acceptable salt, solvate, hydrate or prodrug thereof. In another aspect, the selectivity is in the range of about 1.1-fold to 10,000-fold; 1.1-fold to 1,000-fold; 1.1-fold to 100-fold; 5-fold to 100-fold; 10-fold to 100-fold, etc.

In other aspects, the invention provides a method of treating a subject suffering from or susceptible to inflammation, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof.

In other aspects, the invention provides a method of treating inflammation in a subject identified as in need thereof, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof.

In other aspects, the invention provides a method of treating a subject suffering from or susceptible to inflammation, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that said subject is treated for said inflammation.

In other aspects, the invention provides a method of treating inflammation in a subject identified as in need thereof, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that said subject is treated for said inflammation.

In other aspects, the invention provides a method of treating a subject suffering from or susceptible to inflammation, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that said inflammation in said subject is reduced.

In other aspects, the invention provides a method of treating inflammation in a subject identified as in need thereof, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that said inflammation in said subject is reduced.

In other aspects, the invention provides a method of treating a subject suffering from or susceptible to a proliferative disease, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof.

In other aspects, the invention provides a method of treating a proliferative disease in a subject identified as in need thereof, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof.

In other aspects, the invention provides a method of treating a subject suffering from or susceptible to a proliferative disease, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that said subject is treated for said proliferative disease.

In other aspects, the invention provides a method of treating a proliferative disease in a subject identified as in need thereof, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that said subject is treated for said proliferative disease.

In other aspects, the invention provides a method of modulating the proliferation activity in a subject, comprising contacting the subject with a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, in an amount and under conditions sufficient to modulate proliferation activity.

In one aspect, the invention provides a method of treating a subject suffering from or susceptible to a proliferation related disorder or disease, comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof.

In another aspect, the invention provides a method of treating a subject suffering from or susceptible to a proliferation related activity related disorder or disease, wherein the subject has been identified as in need of treatment for a proliferation related disorder or disease, comprising administering to said subject in need thereof, a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that said subject is treated for said disorder.

In another aspect, the invention provides a method of treating a subject suffering from or susceptible to a cell proliferation related disorder or disease, wherein the subject has been identified as in need of treatment for a cell proliferation related disorder or disease, comprising administering to said subject in need thereof, a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that cell proliferation in said subject is modulated (e.g., down regulated). In another aspect, the compounds or compositions delineated herein preferentially target cancer cells over nontransformed cells.

In another aspect, the proliferative disease is cancer.

In another aspect, the cancer is multiple myeloma, lymphoma, chronic lymphocytic leukemia (CLL), acute myelogenous leukemia (AML), large granular lymphocyte leukemia (LGL), sarcoma, lung cancer, breast cancer, renal cancer, prostate cancer, pancreatic cancer, melanoma, colon carcinoma, gastric carcinoma, cervical cancer, ovarian cancer, liver cancer, or head and neck cancer.

In a specific aspect, the invention provides a method of treating cancer, tumor growth, cancer of the colon, breast, bone, brain and others (e.g., osteosarcoma, neuroblastoma, colon adenocarcinoma), comprising administering to said subject in need thereof, an effective amount of any compound or seaweed extract delineated herein, and pharmaceutically acceptable salts thereof. Other cancers that may be treated by the compositions and methods of the invention include cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, cutaneous T-cell lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma). Other diseases and disorders that can be treated include the treatment of inflammatory disorders, neurodegenerative diseases, protozoal and latent viral infections, and (fibro)proliferative disorders.

In another aspect, the invention provides a method of treating a subject suffering from or susceptible to autoimmune diseases, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof.

In another aspect, the invention provides a method of treating autoimmune diseases in a subject identified as in need thereof, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof.

In another aspect, the invention provides a method of treating a subject suffering from or susceptible to autoimmune diseases, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that said subject is treated for said autoimmune diseases In another aspect, the invention provides a method of treating autoimmune diseases in a subject identified as in need thereof, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that said subject is treated for said autoimmune diseases.

In another aspect, the invention provides a method of treating a subject suffering from or susceptible to autoimmune diseases, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that said autoimmune diseases in said subject is reduced.

In another aspect, the invention provides a method of treating autoimmune diseases in a subject identified as in need thereof, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that said autoimmune diseases in said subject is reduced.

In another aspect, the autoimmune disease is acute disseminated encephalomyelitis, acute motor axonal neuropathy, Addison's disease, adiposis dolorosa, adult-onset Still's disease, alopecia areata, ankylosing Spondylitis, anti-Glomerular Basement Membrane nephritis, anti-neutrophil cytoplasmic antibody-associated vasculitis, anti-N-Methyl-D-Aspartate Receptor Encephalitis, antiphospholipid syndrome, antisynthetase syndrome, aplastic anemia, autoimmune Angioedema, autoimmune enteropathy, autoimmune hemolytic anemia, autoimmune hepatitis, autoimmune inner ear disease, autoimmune lymphoproliferative syndrome, autoimmune neutropenia, autoimmune oophoritis, autoimmune orchitis, autoimmune pancreatitis, autoimmune polyendocrine syndrome, autoimmune polyendocrine syndrome type 2, autoimmune polyendocrine syndrome type 3, autoimmune progesterone dermatitis, autoimmune retinopathy, autoimmune thrombocytopenic purpura, autoimmune thyroiditis, autoimmune urticaria, autoimmune uveitis, balo concentric sclerosis, Behçet's disease, Bickerstaff's encephalitis, bullous pemphigoid, celiac disease, chronic fatigue syndrome, chronic inflammatory demyelinating polyneuropathy, Churg-Strauss syndrome, cicatricial pemphigoid, Cogan syndrome, cold agglutinin disease, complex regional pain syndrome, CREST syndrome, Crohn's disease, dermatitis herpetiformis, dermatomyositis, diabetes mellitus type 1, discoid lupus erythematosus, endometriosis, enthesitis, enthesitis-related arthritis, eosinophilic esophagitis, eosinophilic fasciitis, epidermolysis bullosa acquisita, erythema nodosum, essential mixed cryoglobulinemia, Evans syndrome, Felty syndrome, fibromyalgia, gastritis, gestational pemphigoid, giant cell arteritis, Goodpasture syndrome, Graves' disease, Graves ophthalmopathy, Guillain-Barré syndrome, Hashimoto's encephalopathy, Henoch-Schonlein purpura, Hidradenitis suppurativa, idiopathic inflammatory demyelinating diseases, IgG4-related systemic disease, inclusion body myositis, Inflamatory Bowel Disease (IBD), intermediate uveitis, interstitial cystitis, Juvenile Arthritis, Kawasaki's disease, Lambert-Eaton myasthenic syndrome, leukocytoclastic vasculitis, lichen planus, lichen sclerosus, ligneous conjunctivitis, linear IgA disease, lupus nephritis, lupus vasculitis, Lyme disease (Chronic), Ménière's disease, microscopic colitis, microscopic polyangiitis, mixed connective tissue disease, Mooren's ulcer, morphea, Mucha-Habermann disease, multiple sclerosis, myasthenia gravis, myocarditis, myositis, neuromyelitis optica, neuromyotonia, opsoclonus myoclonus syndrome, optic neuritis, Ord's thyroiditis, palindromic rheumatism, paraneoplastic cerebellar degeneration, Parry Romberg syndrome, Parsonage-Turner syndrome, Pediatric Autoimmune Neuropsychiatric Disorder Associated with Streptococcus, pemphigus vulgaris, pernicious anemia, pityriasis lichenoides et varioliformis acuta, POEMS syndrome, polyarteritis nodosa, polymyalgia rheumatic, polymyositis, postmyocardial infarction syndrome, postpericardiotomy syndrome, primary biliary cirrhosis, primary immunodeficiency, primary sclerosing cholangitis, progressive inflammatory neuropathy, psoriasis, psoriatic arthritis, pure red cell aplasia, pyoderma gangrenosum, Raynaud phenomenon, reactive arthritis, relapsing polychondritis, restless leg syndrome, retroperitoneal fibrosis, rheumatic fever, rheumatoid arthritis, rheumatoid vasculitis, sarcoidosis, Schnitzler syndrome, scleroderma, Sjogren's syndrome, stiff person syndrome, subacute bacterial endocarditis, Susac's syndrome, Sydenham chorea, sympathetic ophthalmia, Systemic Lupus Erythematosus, systemic scleroderma, thrombocytopenia, Tolosa-Hunt syndrome, transverse myelitis, ulcerative colitis, undifferentiated connective tissue disease, urticaria, urticarial vasculitis, vasculitis, or vitiligo.

In another aspect, the autoimmune disease is multiple sclerosis, rheumatoid arthritis, or giant cell arteritis.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

BRIEF DESCRIPTION OF THE DRAWINGS

The present invention is further described below with reference to the following non-limiting examples and with reference to the following figures, in which.

DETAILED DESCRIPTION

Definitions

Figure 1:
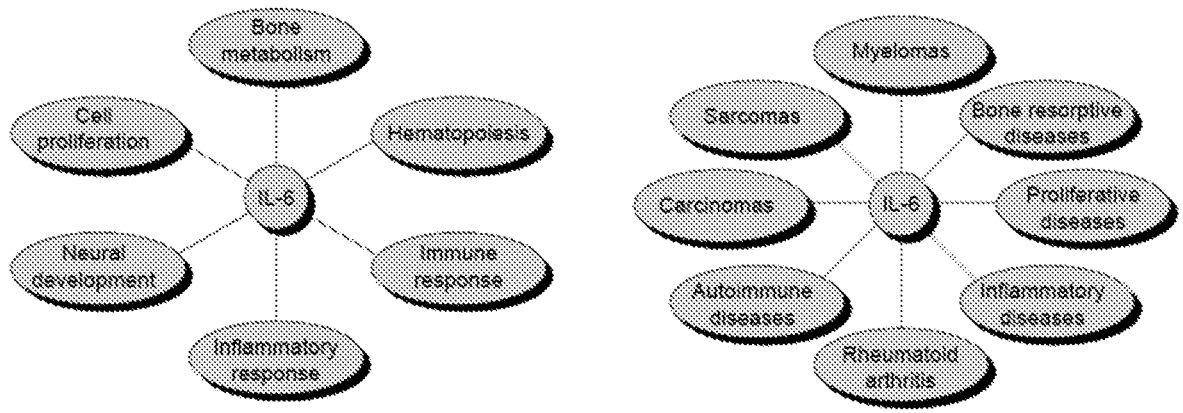
FIG. 1. depicts the roles IL-6 plays in normal and pathological conditions.

In order that the invention may be more readily understood, certain terms are first defined here for convenience.

As used herein, the term "treating" a disorder encompasses ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes blocking, inhibiting, attenuating, protecting against, modulating, reversing the effects of and reducing the occurrence of e.g., the harmful effects of a disorder.

As used herein, "inhibiting" encompasses preventing, reducing and halting progression.

As used herein, "activating" encompasses permitting, increasing and enhancing progression.

The term "modulate" refers to increases or decreases in the activity of a cell in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A "peptide" is a sequence of at least two amino acids. Peptides can consist of short as well as long amino acid sequences, including proteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "protein" refers to series of amino acid residues connected one to the other by peptide bonds between the alpha-amino and carboxy groups of adjacent residues.

Amino acids may be referred to herein by either their commonly known three letter symbols or by the one-letter symbols recommended by the IUPAC-IUB Biochemical Nomenclature Commission.

As to amino acid sequences, one of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I. The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the elastase inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 µg/kg to about 200 mg/kg, preferably about 0.01 mg/kg to about 200 mg/kg, more preferably about 0.015 mg/kg to about 30 mg/kg of body weight. In other embodiments, the therapeutically effect amount may range from about 1.0 pM to about 10 µM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 µg/kg to about 200 mg/kg of body weight, one time per day for between about 1 to 10 weeks, preferably between 2 to 8 weeks, more preferably between about 3 to 7 weeks, and even more preferably for about 4, 5, or 6 weeks. In another example, a subject may be treated daily for several years in the setting of a chronic condition or illness. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Furthermore the compounds of the invention include olefins having either geometry: "Z" refers to what is referred to as a "cis" (same side) conformation whereas "E" refers to what is referred to as a "trans" (opposite side) conformation. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "haloalkyl" refers to an alkyl group that is substituted by one or more halo substituents. Examples of haloalkyl groups include fluoromethyl, difluoromethyl, trifluoromethyl, bromomethyl, chloromethyl, and 2,2,2-trifluoroethyl.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The term "arylalkynyl" refers to an unsaturated hydrocarbon chain that may be a straight chain or branched chain, containing 2 to 12 carbon atoms and at least one carbon-carbon triple bond wherein one or more of the sp hybridized carbons of the alkynyl unit attaches to an aryl moiety. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "alkylthio" refers to an —S-alkyl substituent.

The term "alkoxyalkyl" refers to an -alkyl-O-alkyl substituent.

The term "haloalkoxy" refers to an —O-alkyl that is substituted by one or more halo substituents. Examples of haloalkoxy groups include trifluoromethoxy, and 2,2,2-trifluoroethoxy.

The term "haloalkoxyalkyl" refers to an -alkyl-O-alkyl' where the alkyl' is substituted by one or more halo substituents.

The term "haloalkylaminocarbonyl" refers to a —C(O)-amino-alkyl where the alkyl is substituted by one or more halo substituents.

The term "haloalkylthio" refers to an —S-alkyl that is substituted by one or more halo substituents. Examples of haloalkylthio groups include trifluoromethylthio, and 2,2,2-trifluoroethylthio.

The term "haloalkylcarbonyl" refers to an —C(O)-alkyl that is substituted by one or more halo substituents. An example of a haloalkylcarbonyl group includes trifluoroacetyl.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "cycloalkoxy" refers to an —O-cycloalkyl substituent.

The term "cycloalkoxyalkyl" refers to an -alkyl-O-cycloalkyl substituent.

The term "cycloalkylalkoxy" refers to an —O-alkyl-cycloalkyl substituent.

The term "cycloalkylaminocarbonyl" refers to an —C(O)—NH-cycloalkyl substituent.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "aryloxy" refers to an —O-aryl substituent.

The term "arylalkoxy" refers to an —O-alkyl-aryl substituent.

The term "arylalkylthio" refers to an —S-alkyl-aryl substituent.

The term "arylthioalkyl" refers to an -alkyl-S-aryl substituent.

The term "arylalkylaminocarbonyl" refers to a —C(O)-amino-alkyl-aryl substituent.

The term "arylalkylsulfonyl" refers to an —S(O)$_2$-alkyl-aryl substituent.

The term "arylalkylsulfinyl" refers to an —S(O)-alkyl-aryl substituent.

The term "aryloxyalkyl" refers to an -alkyl-O-aryl substituent.

The term "alkylaryl" refers to an -aryl-alkyl substituent.

The term "arylalkyl" refers to an -alkyl-aryl substituent.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heteroaryloxy" refers to an —O-heteroaryl substituent.

The term "heteroarylalkoxy" refers to an —O-alkyl-heteroaryl substituent.

The term "heteroaryloxyalkyl" refers to an -alkyl-O-heteroaryl substituent. The term "nitrogen-containing heteroaryl" refers to a heteroaryl group having 1-4 ring nitrogen heteroatoms if monocyclic, 1-6 ring nitrogen heteroatoms if bicyclic, or 1-9 ring nitrogen heteroatoms if tricyclic.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Compounds of the Invention

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, 2$^{nd}$ Edition*, Carlson R, Ed, 2005; Elsevier Science Ltd.; Jähnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

As can be appreciated by the skilled artisan, methods of synthesizing the compounds of the formulae herein will be evident to those of ordinary skill in the art, including in the schemes and examples herein. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired compounds of the present invention.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

The present invention also contemplates solvates (e.g., hydrates) of a compound of herein, compositions thereof, and their use in the treatment of a disease, disorder, or symptom thereof herein. As used herein, "solvate" refers to the physical association of a compound of the invention with one or more solvent or water molecules, whether organic or inorganic. In certain instances, the solvate is capable of isolation, for example, when one or more solvate molecules are incorporated in the crystal lattice of the crystalline solid.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Methods of Treatment

This invention is directed towards compounds, compositions, and methods of treating diseases and disorders by use of the compounds and compositions delineated herein.

In other aspects, the invention provides a method of treating a disease, disorder, or symptom thereof in a subject, comprising administering to the subject any compound or composition delineated herein. In another aspect, the compound or composition is administered in an amount and under conditions sufficient to ameliorate the disease, disorder, or symptom thereof in a subject.

In another aspect, the disease, disorder, or symptom includes proliferative diseases and disorders, inflammation, autoimmune disorders (e.g., multiple sclerosis, rheumatoid arthritis, giant cell arteritis, etc.), cancer, Alzheimer's disease and other neurodegenerative disorders, stroke, chronic kidney disease, type II diabetes, cancer, tumor growth, cancer of the colon, breast, bone, brain and others (e.g., osteosarcoma, neuroblastoma, colon adenocarcinoma), cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, cutaneous T-cell lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma). Other diseases and disorders that can be treated include the treatment of inflammatory disorders, neurodegenerative diseases, protozoal and latent viral infections, and (fibro)proliferative disorders, and aging itself.

In another aspect, the invention provides a method of inhibiting IL-6 signaling comprising administering a compound of any of the formulae herein (e.g., formulae (I)-(XXI)), or a pharmaceutically acceptable salt, solvate, hydrate or prodrug thereof. In another aspect, the inhibition of IL-6 is in vitro. In another aspect, the inhibition of IL-6 is in vivo. In another aspect, the method of inhibition of IL-6 further comprises administering the compound, or a pharmaceutically acceptable salt, solvate, hydrate or prodrug thereof, to a subject.

In another aspect, the invention provides a method of inhibiting IL-6/gp130 comprising administering a compound of any of the formulae herein (e.g., formulae (I)-(XXI)), or a pharmaceutically acceptable salt, solvate, hydrate or prodrug thereof. In another aspect, the inhibition is in vitro. In another aspect, the inhibition is in vivo. In another aspect, the method further comprises administering the compound, or a pharmaceutically acceptable salt, solvate, hydrate or prodrug thereof, to a subject.

In another aspect, the invention provides a method of inhibiting the formation of the dimerization of two of the IL-6/IL-6Rα/gp130 trimers comprising administering a compound of any of the formulae herein (e.g., formulae (I)-(XXI)), or a pharmaceutically acceptable salt, solvate, hydrate or prodrug thereof. In another aspect, the inhibition is in vitro. In another aspect, the inhibition is in vivo. In another aspect, the method further comprises administering the compound, or a pharmaceutically acceptable salt, solvate, hydrate or prodrug thereof, to a subject.

As discussed above, the homodimerization of IL-ML-#Rα/gp130 trimers is unique to IL-6 and IL-11 among the other IL family members. Also, as discussed above, the IL-NIL-#Rα/gp130 trimers possess beneficial biological functions unrelated to inflammation or cancer and, thus, it is preferable to inhibit homodimerization of IL-ML-#Rα/gp130 trimers to the corresponding hexamer without disrupting the formation or biological activity of the corresponding IL-ML-#Rα/gp130 trimer. This selective inhibition of homodimerization of IL-ML-#Rα/gp130 trimers relative to the inhibition of the formation or biological activity of the corresponding IL-NIL-#Rα/gp130 trimer is believed to result in an improved side effect profile. Thus, one aspect of the invention is a method of selectively inhibiting the homodimerization of IL-6/IL-6Rα/gp130 trimers relative to the inhibition of the formation or biological activity of the corresponding IL-6/IL-6Rα/gp130 trimer, the method comprising administering a compound of any of the formulae herein (e.g., formulae (I)-(XXI)), or a pharmaceutically acceptable salt, solvate, hydrate or prodrug thereof. In another aspect, the selectivity is in the range of about 1.1-fold to 10,000; 1.1-fold to 1,000-fold; 1.1-fold to 100-fold; 5-fold to 100-fold; 10-fold to 100-fold, etc.

In other aspects, the invention provides a method of treating a subject suffering from or susceptible to inflammation, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof.

In other aspects, the invention provides a method of treating inflammation in a subject identified as in need thereof, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof.

In other aspects, the invention provides a method of treating a subject suffering from or susceptible to inflammation, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that said subject is treated for said inflammation.

In other aspects, the invention provides a method of treating inflammation in a subject identified as in need thereof, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that said subject is treated for said inflammation.

In other aspects, the invention provides a method of treating a subject suffering from or susceptible to inflammation, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that said inflammation in said subject is reduced.

In other aspects, the invention provides a method of treating inflammation in a subject identified as in need thereof, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that said inflammation in said subject is reduced.

In other aspects, the invention provides a method of treating a subject suffering from or susceptible to a proliferative disease, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof.

In other aspects, the invention provides a method of treating a proliferative disease in a subject identified as in need thereof, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof.

In other aspects, the invention provides a method of treating a subject suffering from or susceptible to a proliferative disease, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that said subject is treated for said proliferative disease.

In other aspects, the invention provides a method of treating a proliferative disease in a subject identified as in need thereof, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that said subject is treated for said proliferative disease.

In other aspects, the invention provides a method of modulating the proliferation activity in a subject, comprising contacting the subject with a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, in an amount and under conditions sufficient to modulate proliferation activity.

In one aspect, the invention provides a method of treating a subject suffering from or susceptible to a proliferation related disorder or disease, comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof.

In another aspect, the invention provides a method of treating a subject suffering from or susceptible to a proliferation related activity related disorder or disease, wherein the subject has been identified as in need of treatment for a proliferation related disorder or disease, comprising administering to said subject in need thereof, a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that said subject is treated for said disorder.

In another aspect, the invention provides a method of treating a subject suffering from or susceptible to a cell proliferation related disorder or disease, wherein the subject has been identified as in need of treatment for a cell proliferation related disorder or disease, comprising administering to said subject in need thereof, a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that cell proliferation in said subject is modulated (e.g., down regulated). In another aspect, the compounds or compositions delineated herein preferentially target cancer cells over nontransformed cells.

In another aspect, the proliferative disease is cancer.

In another aspect, the cancer is multiple myeloma, lymphoma, chronic lymphocytic leukemia (CLL), acute myelogenous leukemia (AML), large granular lymphocyte leukemia (LGL), sarcoma, lung cancer, breast cancer, renal cancer, prostate cancer, pancreatic cancer, melanoma, colon carcinoma, gastric carcinoma, cervical cancer, ovarian cancer, liver cancer, or head and neck cancer.

In a specific aspect, the invention provides a method of treating cancer, tumor growth, cancer of the colon, breast, bone, brain and others (e.g., osteosarcoma, neuroblastoma, colon adenocarcinoma), comprising administering to said subject in need thereof, an effective amount of any compound or seaweed extract delineated herein, and pharmaceutically acceptable salts thereof. Other cancers that may be treated by the compositions and methods of the invention include cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, cutaneous T-cell lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma). Other diseases and disorders that can be treated include the treatment of inflammatory disorders, neurodegenerative diseases, protozoal and latent viral infections, and (fibro)proliferative disorders.

In another aspect, the invention provides a method of treating a subject suffering from or susceptible to autoimmune diseases, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof.

In another aspect, the invention provides a method of treating autoimmune diseases in a subject identified as in need thereof, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof.

In another aspect, the invention provides a method of treating a subject suffering from or susceptible to autoimmune diseases, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that said subject is treated for said autoimmune diseases In another aspect, the invention provides a method of treating autoimmune diseases in a subject identified as in need thereof, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that said subject is treated for said autoimmune diseases.

In another aspect, the invention provides a method of treating a subject suffering from or susceptible to autoimmune diseases, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that said autoimmune diseases in said subject is reduced.

In another aspect, the invention provides a method of treating autoimmune diseases in a subject identified as in need thereof, the method comprising administering to the subject a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, such that said autoimmune diseases in said subject is reduced.

In another aspect, the autoimmune disease is acute disseminated encephalomyelitis, acute motor axonal neuropathy, Addison's disease, adiposis dolorosa, adult-onset Still's disease, alopecia areata, ankylosing Spondylitis, anti-Glomerular Basement Membrane nephritis, anti-neutrophil cytoplasmic antibody-associated vasculitis, anti-N-Methyl-D-Aspartate Receptor Encephalitis, antiphospholipid syndrome, antisynthetase syndrome, aplastic anemia, autoimmune Angioedema, autoimmune enteropathy, autoimmune hemolytic anemia, autoimmune hepatitis, autoimmune inner ear disease, autoimmune lymphoproliferative syndrome, autoimmune neutropenia, autoimmune oophoritis, autoimmune orchitis, autoimmune pancreatitis, autoimmune polyendocrine syndrome, autoimmune polyendocrine syndrome type 2, autoimmune polyendocrine syndrome type 3, autoimmune progesterone dermatitis, autoimmune retinopathy, autoimmune thrombocytopenic purpura, autoimmune thyroiditis, autoimmune urticaria, autoimmune uveitis, balo concentric sclerosis, Behçet's disease, Bickerstaff's encephalitis, bullous pemphigoid, celiac disease, chronic fatigue syndrome, chronic inflammatory demyelinating polyneuropathy, Churg-Strauss syndrome, cicatricial pemphigoid, Cogan syndrome, cold agglutinin disease, complex regional pain syndrome, CREST syndrome, Crohn's disease, dermatitis herpetiformis, dermatomyositis, diabetes mellitus type 1, discoid lupus erythematosus, endometriosis, enthesitis, enthesitis-related arthritis, eosinophilic esophagitis, eosinophilic fasciitis, epidermolysis bullosa acquisita, erythema nodosum, essential mixed cryoglobulinemia, Evans syndrome, Felty syndrome, fibromyalgia, gastritis, gestational pemphigoid, giant cell arteritis, Goodpasture syndrome, Graves' disease, Graves ophthalmopathy, Guillain-Barré syndrome, Hashimoto's encephalopathy, Henoch-Schonlein purpura, Hidradenitis suppurativa, idiopathic inflammatory demyelinating diseases, IgG4-related systemic disease, inclusion body myositis, Inflamatory Bowel Disease (IBD), intermediate uveitis, interstitial cystitis, Juvenile Arthritis, Kawasaki's disease, Lambert-Eaton myasthenic syndrome, leukocytoclastic vasculitis, lichen planus, lichen sclerosus, ligneous conjunctivitis, linear IgA disease, lupus nephritis, lupus vasculitis, Lyme disease (Chronic), Ménière's disease, microscopic colitis, microscopic polyangiitis, mixed connective tissue disease, Mooren's ulcer, morphea, Mucha-Habermann disease, multiple sclerosis, myasthenia gravis, myocarditis, myositis, neuromyelitis optica, neuromyotonia, opsoclonus myoclonus syndrome, optic neuritis, Ord's thyroiditis, palindromic rheumatism, paraneoplastic cerebellar degeneration, Parry Romberg syndrome, Parsonage-Turner syndrome, Pediatric Autoimmune Neuropsychiatric Disorder Associated with Streptococcus, pemphigus vulgaris, pernicious anemia, pityriasis lichenoides et varioliformis acuta, POEMS syndrome, polyarteritis nodosa, polymyalgia rheumatic, polymyositis, postmyocardial infarction syndrome, postpericardiotomy syndrome, primary biliary cirrhosis, primary immunodeficiency, primary sclerosing cholangitis, progressive inflammatory neuropathy, psoriasis, psoriatic arthritis, pure red cell aplasia, pyoderma gangrenosum, Raynaud phenomenon, reactive arthritis, relapsing polychondritis, restless leg syndrome, retroperitoneal fibrosis, rheumatic fever, rheumatoid arthritis, rheumatoid vasculitis, sarcoidosis, Schnitzler syndrome, scleroderma, Sjogren's syndrome, stiff person syndrome, subacute bacterial endocarditis, Susac's syndrome, Sydenham chorea, sympathetic ophthalmia, Systemic Lupus Erythematosus, systemic scleroderma, thrombocytopenia, Tolosa-Hunt syndrome, transverse myelitis, ulcerative colitis, undifferentiated connective tissue disease, urticaria, urticarial vasculitis, vasculitis, or vitiligo.

In another aspect, the autoimmune disease is multiple sclerosis, rheumatoid arthritis, or giant cell arteritis.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

Pharmaceutical Compositions

In one aspect, the invention provides a pharmaceutical composition comprising the compound and a pharmaceutically acceptable carrier.

In another embodiment, the invention provides a pharmaceutical composition further comprising an additional therapeutic agent. In another embodiment, the invention provides a pharmaceutical composition further comprising an additional therapeutic agent. In a further embodiment, the additional therapeutic agent is an anti-cancer agent, antifungal agent, cardiovascular agent, anti-inflammatory agent, chemotherapeutic agent, an anti-angiogenesis agent, cytotoxic agent, an anti-proliferation agent, metabolic disease agent, ophthalmologic disease agent, central nervous system (CNS) disease agent, urologic disease agent, or gastrointestinal disease agent. In a further embodiment, the additional therapeutic agent is an anti-cancer agent, chemotherapeutic agent, an anti-angiogenesis agent, cytotoxic agent, or an anti-proliferation agent.

In one aspect, the invention provides a kit comprising an effective amount of a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, in unit dosage form, together with instructions for administering the compound to a subject suffering from or susceptible to inflammation, a proliferative disease, an autoimmune disease, etc.

In one aspect, the invention provides a kit comprising an effective amount of a compound of any of the formulae herein (e.g., formulae (I)-(XXI)), or a pharmaceutically acceptable salt, solvate, hydrate or prodrug thereof, or a pharmaceutical composition comprising a compound of any of the formulae herein (e.g., formulae (I)-(XXI)), or a pharmaceutically acceptable salt, solvate, hydrate or prodrug thereof, in unit dosage form, together with instructions for administering the compound to a subject suffering from or susceptible to a cell proliferation disease or disorder, including cancer, solid tumor, angiogenesis, etc.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebro ventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific organozinc compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage. The carrier can be a solvent or dispersion medium containing, for example, water, DMSO, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compound of the invention in the required amount in the appropriate solvent with various of the other ingredients enumerated above, as required, followed by filtered sterilization. Generally, dispersions are prepared by incorporating the various sterilized compounds into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yields a powder of the active ingredient plus any additional desired ingredient from previously sterile-filtered solution thereof.

For oral therapeutic administration, the compound may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains compound concentration sufficient to treat a disorder in a subject.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragacanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present.

Topical administration of the pharmaceutical compositions of this invention is especially useful when the desired treatment involves areas or organs readily accessible by topical application. For topical application topically to the skin, the pharmaceutical composition should be formulated with a suitable ointment, lotion, or cream containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

For topical administration, the active compound(s), extracts, enriched extracts, or prodrug(s) can be formulated as solutions, gels, ointments, creams, suspensions, and the like.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

EXAMPLES

The present invention will now be demonstrated using specific examples that are not to be construed as limiting.

Synthesis

The solvents and reagents used in the present study were purchased from commercial suppliers and were used as received. Progress of the chemical reactions was monitored by thin-layer chromatography on silica gel 60-F254 aluminum plates and detected under UV light. Silica gel for flash silica gel column chromatography was purchased from Sigma-Aldrich Chemical Co. (Milwaukee, Wis.). The purities of all tested compounds are higher than 95% as assessed by HPLC, carried out with a Gemini 5μ C18 110A column (250 mm×4.6 mm) supplied by Phenomenex Inc. CA, USA. Proton nuclear magnetic resonance spectra were obtained with Bruker Avance 300 (300 MHz) or 400 (400 MHz) NMR spectrometer (Billerica, Mass.). Agilent LC/MSD TOF system G3250AA was used for the mass spectra measurements.

The synthesis of these LLM compounds is illustrated in Scheme 1. Firstly, the starting material 1 was condensed with dimethoxytetrahydrofuran in refluxing acetic acid to form the pyrrole ring [Guillon J, Grellier P, Labaied M, et al. Antimalarial activity, and molecular modeling of new pyrrolo[1,2-a]quinoxalines, bispyrrolo[1,2-a]quinoxalines, bispyrido[3,2-α]pyrrolo[1,2-a]pyrazines, and bispyrrolo[1,2-a]thieno[3,2-e]pyrazines. *J Med Chem* 2004, 47, 1997-2009; Lv W, Budke B, Pawlowski M, et al. Development of small molecules that specifically inhibit the D-loop activity of RAD51. *J Med Chem* 2016, 59, 4511-4525], affording compound 2. The nitro group of 2 was then reduced to an amino group using palladium on carbon as catalyst and ammonium formate as hydrogen donor [Ram S, Ehrenkaufer R. Ammonium formate in organic synthesis: a versatile agent in catalytic hydrogen transfer reductions. *Synthesis* 1988, 2, 91-95]. In the condensation reaction of compound 3 and compound 4, at first the conventional EDC condensation method was used, but very little product was obtained. The failure of this reaction may result from the low nucleophilicity of the amino group on compound 3. It was reported that using methanesulfonyl chloride and N-methylimidazole as a combination for the amide condensation reaction is promising when the nucleophilicity of the amine is low [Mao L, Wang Z, Li Y, et al. A convenient synthesis of amino acid arylamides utilizing methanesulfonyl chloride and N-methylimidazole, *SYNLETT*, 2011, 1, 129-133]. After applying these conditions, the yield of the reaction was increased from trace amounts to 23%. The acetyl group was then removed under basic conditions in high yield to give key intermediate 6. Finally, compound 6 reacted with various alkyl chlorides to afford the target compounds.

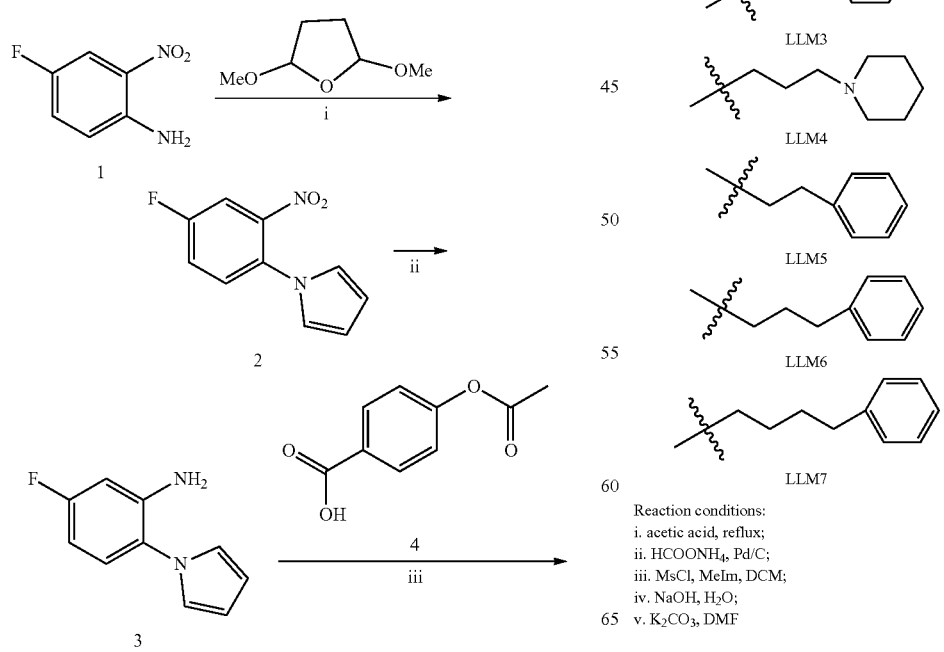

Scheme 1. Synthesis of LLM compounds.

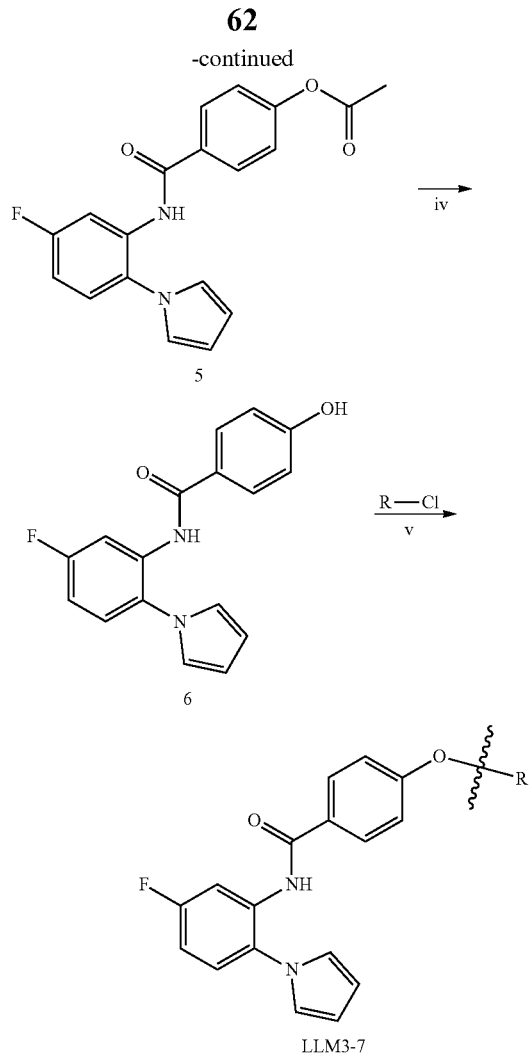

Reaction conditions:
i. acetic acid, reflux;
ii. HCOONH$_4$, Pd/C;
iii. MsCl, MeIm, DCM;
iv. NaOH, H$_2$O;
v. K$_2$CO$_3$, DMF

Example 1: N-(5-fluoro-2-(1H-pyrrol-1-yl)phenyl)-4-(2-(piperidin-1-yl)ethoxy)benzamide (LLM3)

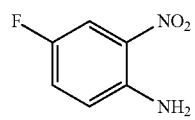

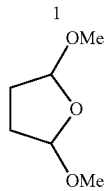

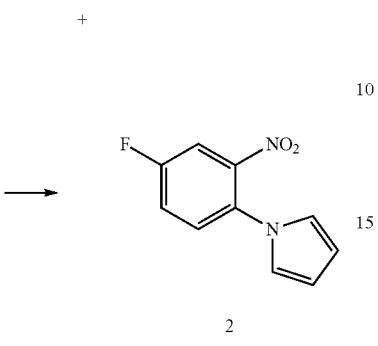

1-(4-fluoro-2-nitrophenyl)-1H-pyrrole (2). 4-fluoro-2-nitroaniline 1 (19.22 mmol) was dissolved in 15 ml glacial acetic acid, followed by the addition of 5-dimethoxytetrahydrofuran (19.22 mmol). The mixture was heated to reflux for 1 hour. After cooling down, the reaction mixture was poured into cold water and then extracted with ethyl acetate (100 ml×3). The organic layer was collected and dried with anhydrous $Na_2SO_4$ and then evaporated to dryness under reduced pressure to give the crude product, which was further purified by flash silica gel column chromatography (ethyl acetate:hexanes=1:10) to give an orange solid (yield 70%). $^1$H NMR (CDCl$_3$) δ 7.61 (1H, q, J1=2.8 Hz, J2=7.6 Hz), 7.48 (1H, m), 7.38 (1H, m), 6.76 (2H, t, J=2.2 Hz), 6.36 (2H, t, J=2.2 Hz). $^{13}$C NMR (CDCl$_3$) δ 157.3, 137.4, 125.6, 122.4, 121.2, 120.3, 111.7, 110.4.

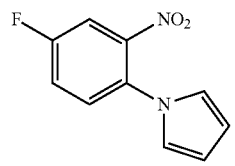

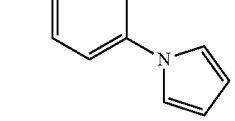

5-fluoro-2-(1H-pyrrol-1-yl)aniline (3). Compound 2 (0.97 mmol) and palladium on charcoal (10%, 20 mg) were suspended in ethanol and heated to reflux. Ammonium formate (9.7 mmol) was added in three portions in two hours. After the reaction was done, the reaction mixture was immediately filtered when hot. The liquid was condensed with rotary evaporator under reduced pressure and re-dissolved in 300 ml ethyl acetate. Then the organic layer was washed with brine (100 ml×3), dried with anhydrous $Na_2SO_4$, and evaporated to dryness under reduced pressure to give crude product, which was further purified by flash silica gel column chromatography (ethyl acetate:hexanes=1: 6) to give beige crystals (yield 80%). $^1$H NMR (CDCl$_3$) δ 7.14 (1H, q, J1=6 Hz, J2=8.8 Hz), 6.79 (2H, t, J=2 Hz), 6.67 (1H, d, J=8.8 Hz), 6.59 (1H, m), 6.33 (2H, t, J=2 Hz).

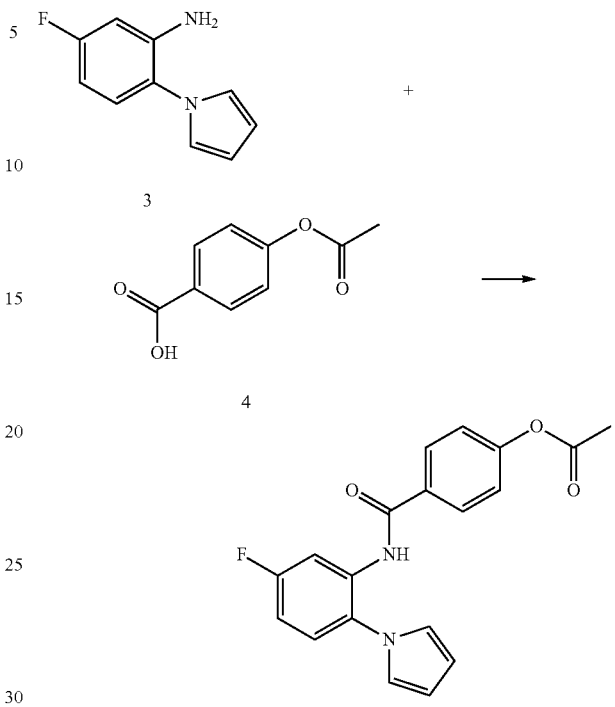

4-((5-fluoro-2-(1H-pyrrol-1-yl)phenyl)carbamoyl)phenyl acetate (5). N-methylimidazole (2.78 mmol) was added to a stirred dichloromethane (10 ml) solution of 4 (6.94 mmol) at 0° C., and the mixture was stirred for 10 min. Methanesulfonyl chloride (2.78 mmol) in dichloromethane (1 ml) was slowly added to the mixture at 0° C. and stirred at that temperature for 20 min. Then compound 3 (2.78 mmol) in dichloromethane (1 ml) was added to the mixture. The reaction was then brought to room temperature and stirred for two hours. After the reaction was done, cold water (200 ml) was added to the reaction mixture, and then extracted with dichloromethane (100 ml×3). The organic layer was dried with anhydrous $Na_2SO_4$ and evaporated to dryness under reduced pressure to give the crude product, which was further purified by flash silica gel column chromatography (ethyl acetate:hexanes=1:10) to give a white solid (yield 23%). $^1$H NMR (CDCl$_3$) δ 8.48 (1H, m), 7.68 (1H, s), 7.61 (2H, d, J=8.8 Hz), 7.33 (1H, m), 7.15 (2H, d, J=8.8 Hz). 6.88 (1H, m), 6.81 (2H, m), 6.46 (2H, m), 2.32 (3H, s).

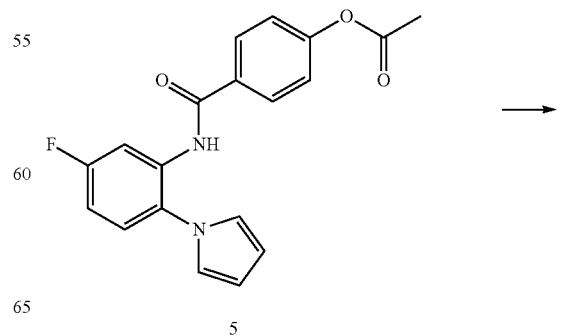

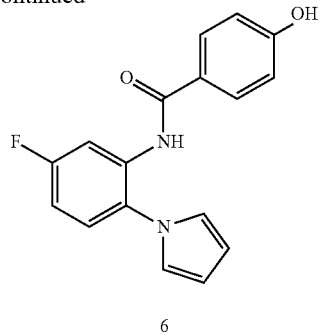

6

N-(5-fluoro-2-(1H-pyrrol-1-yl)phenyl)-4-hydroxybenzamide (6). Compound 5 (0.59 mmol) was dissolved in 5 ml methanol. The solution was cooled in an ice bath, then 0.5 ml of 4 M NaOH solution was slowly added. The reaction was completed almost immediately. 50 ml ethyl acetate and 50 ml water were added to the reaction mixture. The organic layer was separated and washed with brine (20 ml×3). After drying with anhydrous $Na_2SO_4$, the solvent was removed via a rotary evaporator under reduced pressure to give a white solid (yield 96%). $^1$H NMR ($CDCl_3$) δ 8.46 (1H, m), 7.64 (1H, s), 7.49 (2H, d, J=8.8 Hz), 7.32 (1H, m), 6.87 (1H, m), 6.84 (4H, m), 6.48 (2H, t, J=2.2 Hz).

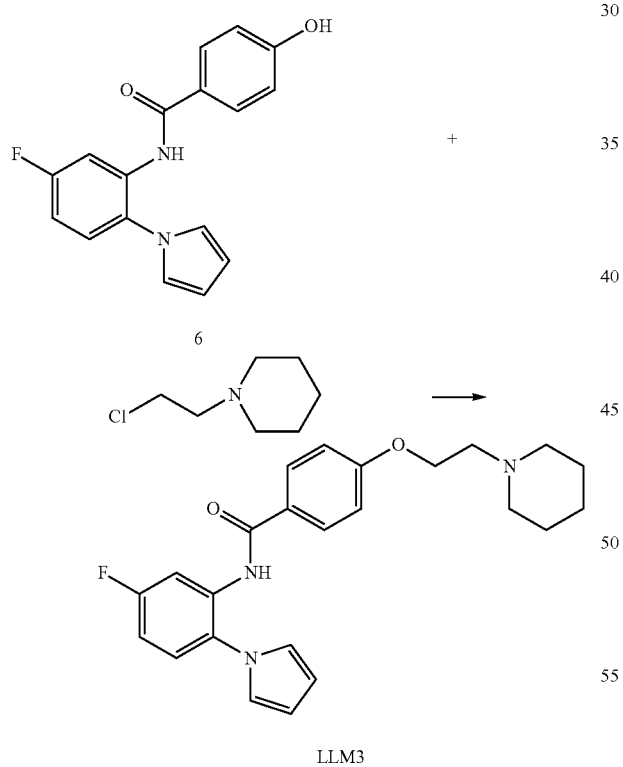

LLM3

N-(5-fluoro-2-(1H-pyrrol-1-yl)phenyl)-4-(2-(piperidin-1-yl)ethoxy)benzamide (LLM3). To a solution of compound 6 (0.06 mmol) in 2 ml DMF was added potassium carbonate (0.18 mmol). The mixture was heated to 90° C. and 1-(2-chloroethyl)piperidine hydrochloride (0.066 mmol) was added. The reaction mixture was then stirred at 90° C. for two hours. After the reaction was completed, the mixture was poured into 50 ml water and then extracted with dichloromethane (50 ml×3). The organic layer was dried with anhydrous $Na_2SO_4$ and evaporated to dryness under reduced pressure to give the crude product, which was further purified by flash silica gel column chromatography (methanol:dichloromethane=1:12) to give a light yellow paste (yield 63%). MS (ESI) m/z 408 (M+H$^+$). $^1$H NMR (DMSO-$d_6$) δ 9.48 (1H, s), 7.75 (2H, d, J=9.0 Hz), 7.59 (1H, m), 7.45 (1H, m), 7.22 (1H, m), 7.03 (2H, (1H, q, J=9.0 Hz), 6.98 (2H, t, J=2.0 Hz), 6.20 (2H, t, J=2.0 Hz), 4.14 (2H, t, J=6.0 Hz), 2.70 (2H, t, J=6.0 Hz), 2.47 (4H, m), 1.50 (4H, m), 1.38 (2H, m). $^{13}$C NMR (DMSO-$d_6$) δ 165.02, 161.37, 161.16, 159.22, 133.82, 132.22, 129.43, 127.66, 125.83, 121.72, 114.26, 114.08, 113.30, 109.42, 65.74, 57.10, 54.31, 25.42, 23.79.

Example 2: N-(5-fluoro-2-(1H-pyrrol-1-yl)phenyl)-4-(3-(piperidin-1-yl)propoxy)benzamide (LLM4)

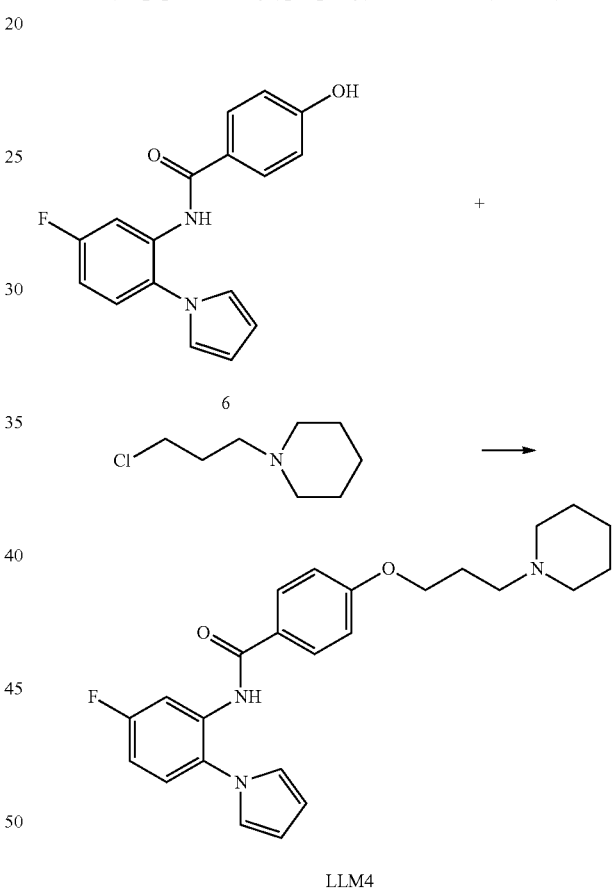

LLM4

LLM4 was prepared under similar conditions as described for the preparation of LLM3, but using 1-(3-chloropropyl)piperidine hydrochloride instead of 1-(2-chloroethyl)piperidine hydrochloride to provide the desired product as a light yellow paste (yield 57%). MS (ESI) m/z 422 (M+H$^+$). $^1$H NMR ($CDCl_3$) δ 8.47 (1H, q, J=2.8 Hz and 10.8 Hz), 7.65 (1H, s), 7.50 (2H, d, J=8.8 Hz), 7.27 (1H, m), 6.90 (2H, m), 6.82 (2H, t, J=2.2 Hz), 6.47 (2H, t, J=2.2 Hz), 4.06 (2H, t, J=6.0 Hz), 2.51-2.59 (6H, m), 2.05 (2H, m), 1.65 (4H, m), 1.59 (2H, m). $^{13}$C NMR ($CDCl_3$) δ 164.44, 163.62, 162.20, 161.17, 136.31, 128.80, 128.30, 126.27, 125.89, 122.43, 114.56, 110.49, 110.00, 108.03, 66.52, 55.66, 54.48, 26.20, 25.42, 24.06.

Example 3: N-(5-fluoro-2-(1H-pyrrol-1-yl)phenyl)-4-phenethoxybenzamide (LLM5)

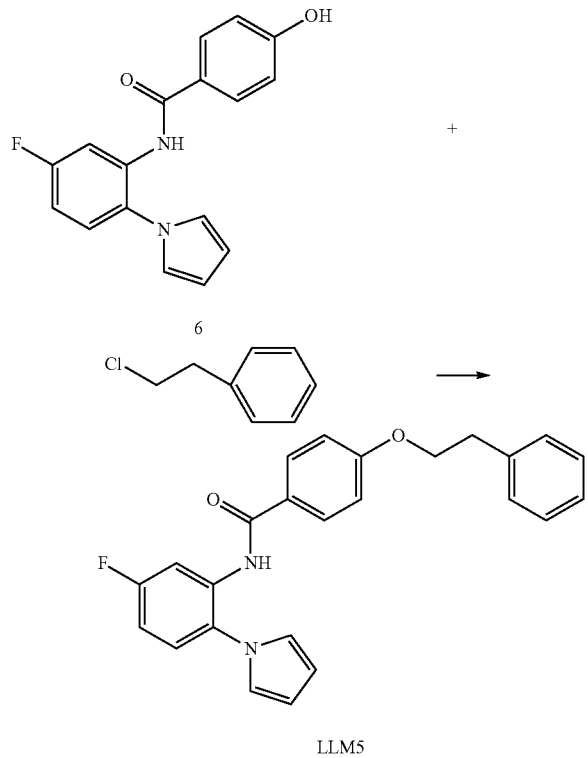

LLM5

LLM5 was prepared under similar conditions as described for the preparation of LLM3, but using (2-chloroethyl)benzene instead of 1-(2-chloroethyl)piperidine hydrochloride to give the desired product as a light yellow solid (yield 69%). MS (ESI) m/z 423 (M+Na$^+$). $^1$H NMR (CDCl$_3$) δ 8.48 (1H, q, J=2.8 Hz and 10.8 Hz), 7.63 (1H, s), 7.51 (2H, m), 7.23-7.31 (6H, m), 6.88 (2H, m), 6.85 (1H, m), 6.81 (2H, t, J=2.2 Hz), 6.45 (2H, t, J=2.2 Hz), 4.21 (2H, t, J=6.8 Hz), 3.10 (2H, t, J=6.8 Hz). $^{13}$C NMR (CDCl$_3$) δ 165.48, 161.78, 161.63, 159.69, 138.62, 134.28, 134.19, 132.19, 129.93, 129.43, 128.80, 128.04, 126.81, 126.347, 122.18, 114.70, 114.55, 109.89, 68.86, 35.24.

Example 4: N-(5-fluoro-2-(1H-pyrrol-1-yl)phenyl)-4-(3-phenylpropoxy)benzamide (LLM6)

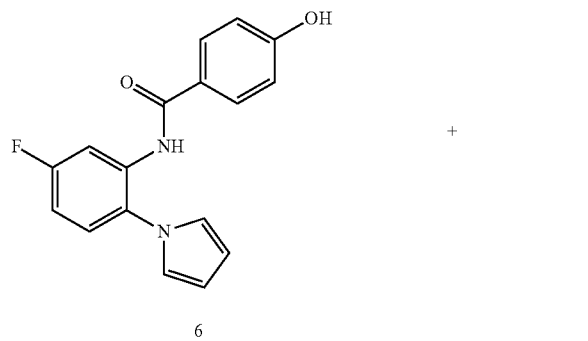

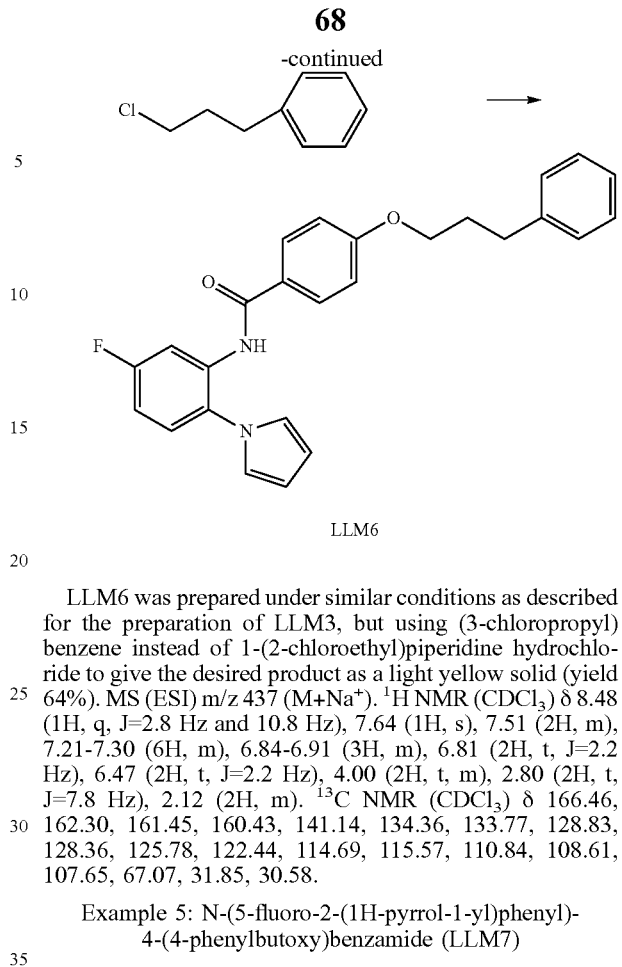

LLM6

LLM6 was prepared under similar conditions as described for the preparation of LLM3, but using (3-chloropropyl)benzene instead of 1-(2-chloroethyl)piperidine hydrochloride to give the desired product as a light yellow solid (yield 64%). MS (ESI) m/z 437 (M+Na$^+$). $^1$H NMR (CDCl$_3$) δ 8.48 (1H, q, J=2.8 Hz and 10.8 Hz), 7.64 (1H, s), 7.51 (2H, m), 7.21-7.30 (6H, m), 6.84-6.91 (3H, m), 6.81 (2H, t, J=2.2 Hz), 6.47 (2H, t, J=2.2 Hz), 4.00 (2H, t, m), 2.80 (2H, t, J=7.8 Hz), 2.12 (2H, m). $^{13}$C NMR (CDCl$_3$) δ 166.46, 162.30, 161.45, 160.43, 141.14, 134.36, 133.77, 128.83, 128.36, 125.78, 122.44, 114.69, 115.57, 110.84, 108.61, 107.65, 67.07, 31.85, 30.58.

Example 5: N-(5-fluoro-2-(1H-pyrrol-1-yl)phenyl)-4-(4-phenylbutoxy)benzamide (LLM7)

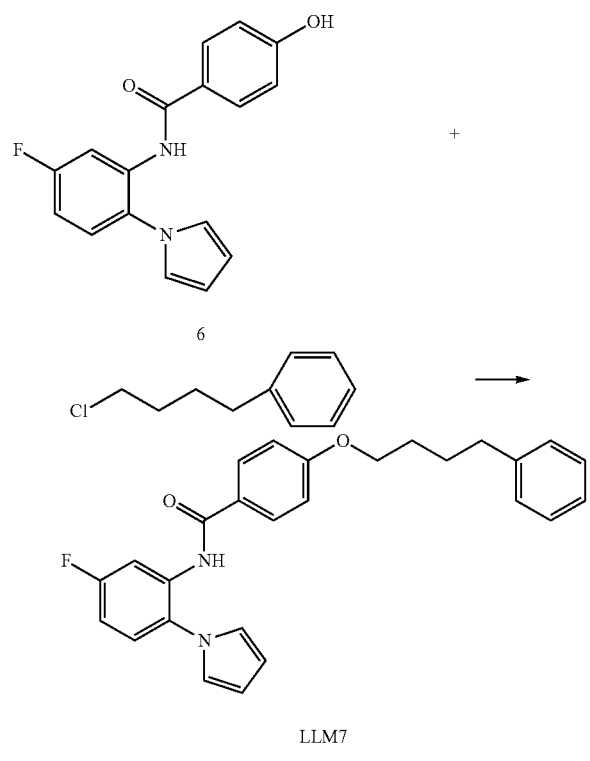

LLM7

N-(5-fluoro-2-(1H-pyrrol-1-yl)phenyl)-4-(4-phenylbutoxy)benzamide (LLM7). LLM7 was prepared under similar conditions as described for the preparation of LLM3, but using (4-chlorobutyl)benzene instead of 1-(2-chloroethyl)piperidine hydrochloride to give the desired product as a light yellow solid (yield 56%). MS (ESI) m/z 451 (M+Na⁺). $^1$H NMR (CDCl$_3$) δ 8.46 (1H, q, J=2.8 Hz and 10.8 Hz), 7.64 (1H, s), 7.50 (2H, m), 7.21-7.31 (6H, m), 6.82-6.90 (3H, m), 6.80 (2H, t, J=2.2 Hz), 6.46 (2H, t, J=2.2 Hz), 4.03 (2H, t, m), 2.84 (2H, t, J=7.8 Hz), 2.01-2.12 (4H, m). $^{13}$C NMR (CDCl$_3$) δ 165.50, 162.03, 161.63, 159.72, 142.43, 134.41, 134.22, 132.65, 129.89, 128.78, 128.75, 127.17, 126.19, 122.20, 114.64, 113.57, 109.89, 68.08, 35.18, 28.57, 27.81.

The synthesis of LLM4X compounds is illustrated in Scheme 2. Firstly, the starting material 1a/1b was protected with a Boc group to afford compound 2a/2b. Then the nitro group was reduced to an amino group using palladium on carbon as catalyst and ammonium formate as hydrogen donor to give intermediate 3a/3b [Ram S, Ehrenkaufer R. Ammonium formate in organic synthesis: a versatile agent in catalytic hydrogen transfer reductions. *Synthesis* 1988, 2, 91-95]. 3a was condensed with various substituted benzoic acids to obtain compounds 4, 6 and 10 [Mao L, Wang Z, Li Y, et al. A convenient synthesis of amino acid arylamides utilizing methanesulfonyl chloride and N-methylimidazole, *SYNLETT,* 2011, 1, 129-133]. Removal of the acetyl group on compounds 4 and 6 under basic conditions gave compounds 5 and 7. S$_N$2 substitution employing different length side chains and deprotection of the Boc group gave targeted molecules LLM41, LLM42, LLM45 and LLM46. Deprotection of the Boc group on compound 10 gave targeted molecules LLM437 and LLM438. 3a was linked with 3-(benzyloxy)aniline through a urea linkage using triphosgene to give compound 8 [Lopez O, Maza S, Maya I, et al. New synthetic approaches to sugar ureas. Access to ureido-β-cyclodextrins. *Tetrahedron.* 2005, 16, 9058-9069]. The benzyl group was removed under reducing conditions to expose the phenol group [Ram S, Ehrenkaufer R. Ammonium formate in organic synthesis: a versatile agent in catalytic hydrogen transfer reductions. Synthesis 1988, 2, 91-95]. S$_N$2 substitution using different length side chains and deprotection of the Boc group gave targeted molecules LLM413 and LLM414. LLM417 and LLM418 were synthesized by a similar synthetic route as shown in Scheme 2 for the preparation of LLM41 and LLM42 except that 3b was used as an intermediate instead of 3a.

Scheme 2. Synthesis of LLM4X compounds.

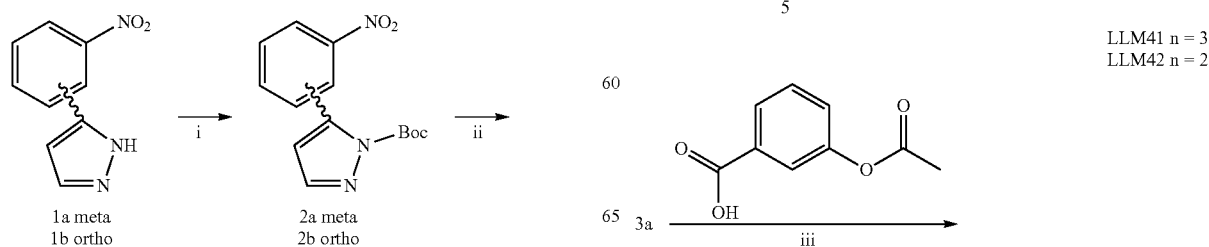

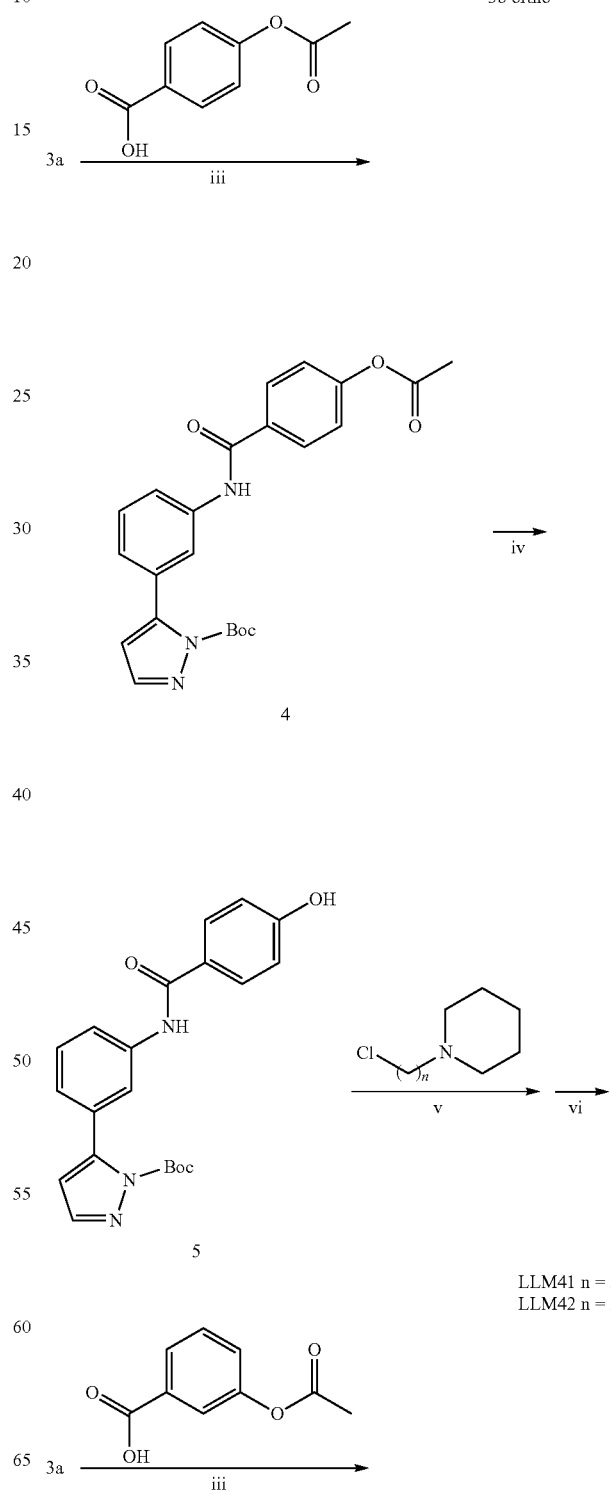

LLM41 n = 3
LLM42 n = 2

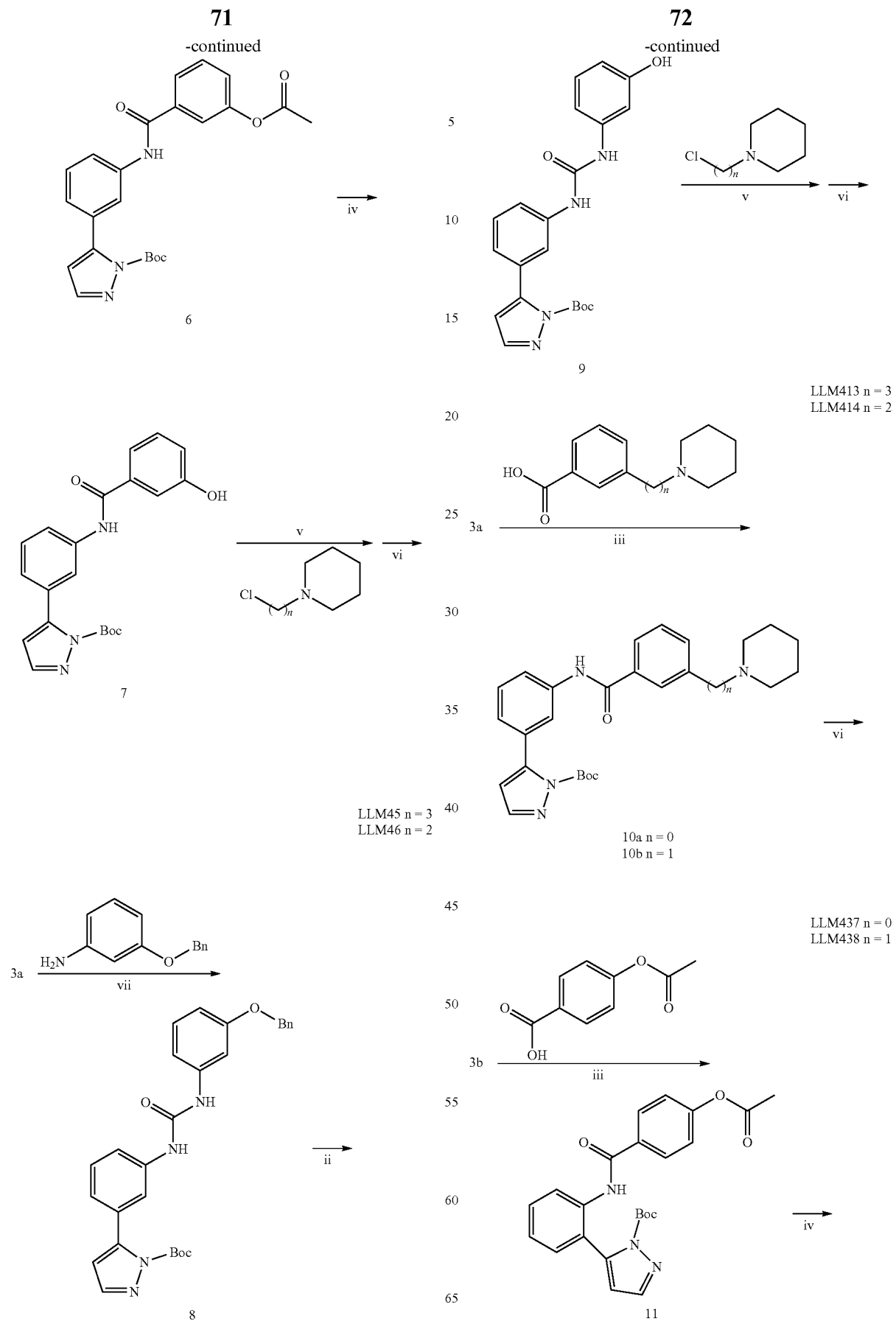

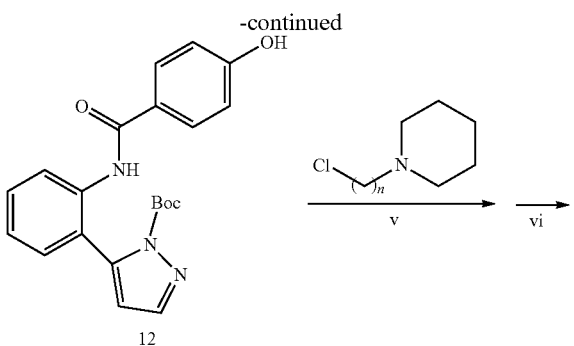

LLM417 n = 3
LLM418 n = 2

Reaction conditions:
i. (Boc)$_2$O, TEA, MeCN, 70° C.;
ii. Pd/C, H$_2$, EtOH, reflux;
iii. MsCl, MeIm, DCM, 0° C.-20° C.;
iv. K$_2$CO$_3$, MeOH, H$_2$O;
v. K$_2$CO$_3$, DMF, 95° C.;
vi. HCl/MeOH, 50° C.;
vii. triphosgene, DIEA, THF, 25° C.

Example 6: N-(3-(1H-pyrazol-5-yl)phenyl)-4-(3-(piperidin-1-yl)propoxy)benzamide (LLM41)

Tert-butyl 5-(3-nitrophenyl)-1H-pyrazole-1-carboxylate (2a). 5-(3-nitrophenyl)-1H-pyrazole 1a (2.64 mmol) was dissolved in 10 ml acetonitrile, followed by the addition of di-tert-butyl dicarbonate (2.91 mmol) and triethylamine (5.27 mmol). The reaction mixture was stirred at 60° C. for 30 min. Then the reaction mixture was condensed to around 3 ml, white precipitate was formed and filtered to give compound 2a as a white solid (yield 80%). $^1$H NMR (CDCl$_3$) δ 8.71 (1H, t, J=4.0 Hz), 8.27 (1H, m), 8.22 (1H, m), 8.16 (1H, d, J=2.2 Hz), 7.61 (1H, t, J=10 Hz), 6.79 (1H, d, J=2.2 Hz), 1.66 (9H, s).

Tert-butyl 5-(2-nitrophenyl)-1H-pyrazole-1-carboxylate (2b). 5-(2-nitrophenyl)-1H-pyrazole 1a was used as starting material, and was reacted according to the similar procedure as described in the synthesis of 2a to give 2b as a white solid (yield 78%). $^1$H NMR (CDCl$_3$) δ 8.10 (1H, t, J=2.8 Hz), 7.81 (2H, m), 7.62 (1H, t, J=7.6 Hz), 7.52 (1H, m), 6.26 (1H, d, J=2.8 Hz), 1.66 (9H, s).

Tert-butyl 5-(3-aminophenyl)-1H-pyrazole-1-carboxylate (3a). Compound 2a (2.0 mmol) and palladium on charcoal (10%, 58 mg) were suspended in ethanol and heated to reflux. Ammonium formate (20 mmol) was added in three portions in two hours. After the reaction was completed, the reaction mixture was immediately filtered. The liquid was condensed with rotary evaporator under reduced pressure and re-dissolved in 500 ml ethyl acetate. Then the organic layer was washed with brine (200 ml×3) and dried with anhydrous Na$_2$SO$_4$ and evaporated to dryness under reduced pressure to give crude product, which was future purified by flash silica gel column chromatography (ethyl acetate:hexanes=1:6) to give 3a as a white solid (yield 75%). $^1$H NMR (CDCl$_3$) δ 7.81 (1H, s), 7.61 (1H, d, J=2.2 Hz), 7.41 (1H, m), 7.31-7.34 (2H, m), 6.61 (1H, d, J=2.2 Hz), 1.53 (9H, s).

Tert-butyl 5-(2-aminophenyl)-1H-pyrazole-1-carboxylate (3b). Compound 2b was reduced according to the similar procedure as described in the synthesis of 3a to give 3b as a white solid (yield 80%). $^1$H NMR (CDCl$_3$) δ 8.08 (1H, t, J=4 Hz), 7.52 (2H, m), 7.14 (1H, t, m), 7.71-7.78 (3H, m), 5.73 (2H, s), 1.66 (9H, s).

Tert-butyl 5-(3-(4-acetoxybenzamido)phenyl)-1H-pyrazole-1-carboxylate (4). N-methylimidazole (6.94 mmol) was added to a stirred dichloromethane (10 ml) solution of 4-acetoxybenzoic acid (2.78 mmol) at 0° C., and the mixture was stirred for 10 min. Methanesulfonyl chloride (2.78 mmol) in dichloromethane (1 ml) was slowly added to the mixture under 0° C. and stirred at that temperature for 20 min. Then compound 3a (2.78 mmol) in dichloromethane (1 ml) was added to the mixture. The reaction was then brought to room temperature and stirred for two hours. After the reaction was completed, cold water (200 ml) was added to the reaction mixture, and then extracted with dichloromethane (100 ml×3). The organic layer was dried with anhydrous Na$_2$SO$_4$ and evaporated to dryness under reduced pressure to give crude product, which was future purified by flash silica gel column chromatography (methanol:dichloromethane=1:15) to give a white solid (yield 35%). $^1$H NMR (CDCl$_3$) δ 8.10 (1H, d, J=3.6 Hz), 8.05 (1H, s), 7.97 (1H, s), 7.91 (2H, m), 7.67 (1H, d, J=7.6 Hz), 7.44 (1H, t, J=7.6 Hz). 7.24 (1H, s), 7.21 (1H, s), 6.73 (1H, d, J=3.6 Hz), 2.34 (3H, m), 1.67 (9H, s).

Tert-butyl 5-(3-(4-hydroxybenzamido)phenyl)-1H-pyrazole-1-carboxylate (5). Compound 4 (0.69 mmol) was dissolved in 7 ml methanol. 0.5 ml of 4 M potassium carbonate solution was slowly added and the reaction was heated to 60° C. and maintained at that temperature for 1 hour. 50 ml ethyl acetate and 50 ml water was added into reaction mixture. The organic layer was separated and washed with brine (20 ml×3). After dried with anhydrous Na$_2$SO$_4$, the solvent was removed through rotary evaporator under reduced pressure to give white solid (yield 86%).

N-(3-(1H-pyrazol-5-yl)phenyl)-4-(3-(piperidin-1-yl)propoxy)benzamide (LLM41). To a solution of compound 5 (0.28 mmol) in 3 ml DMF was added potassium carbonate (0.84 mmol). The mixture was heated to 90° C. and 1-(3-chloropropyl)piperidine hydrochloride (0.31 mmol) was added. Then the reaction mixture was stirred at 90° C. for two hours. After reaction was completed, the mixture was poured into 50 ml water and then extracted with dichloromethane (50 ml×3). The organic layer was dried with anhydrous Na$_2$SO$_4$ and evaporated to dryness under reduced pressure to give a light yellow paste. Then the paste was dissolved in 3 ml 1.25 M hydrogen chloride methanol solution and heated to 50° C. and maintained at that temperature for 30 min. 30 ml water was added to reaction mixture and the pH of solution was adjusted to 7 by adding 2 M sodium bicarbonate drop-wise. The aqueous solution was extracted with dichloromethane (30 ml×3), and then the organic layer was dried with Na$_2$SO$_4$ and evaporated to dryness under reduced pressure to give crude product, which was future purified by flash silica gel column chromatography (methanol:dichloromethane=1:20) and preparative layer chromatography (methanol:dichloromethane=1:8) to give a light yellow paste (yield 25%). MS (ESI) m/z 405 (M+H$^+$). $^1$H NMR (CDCl$_3$) δ 8.05 (1H, d, J=2.1 Hz), 7.82 (2H, m), 7.75 (1H, d, J=9.3 Hz), 7.61 (1H, d, J=2.1 Hz), 7.49 (1H, d, J=7.8 Hz). 7.28 (1H, t, J=7.8 Hz), 6.93 (2H, m), 6.62 (1H, d, J=2.1 Hz), 4.05 (2H, t, J=6.3 Hz), 2.52 (2H, m), 2.44 (4H, m), 2.03 (2H, m), 1.60 (4H, m), 1.46 (2H, m). $^{13}$C NMR (CDCl$_3$) δ 165.47, 162.30, 138.63, 133.207, 129.67, 129.63, 128.56, 121.89, 118.98, 117.53, 114.78, 102.85, 66.81, 55.72, 54.92, 29.34, 25.81, 24.31.

Example 7: N-(3-(1H-pyrazol-5-yl)phenyl)-4-(2-(piperidin-1-yl)ethoxy)benzamide (LLM42)

LLM42 was prepared under similar conditions as described for the preparation of LLM41, but using 1-(2- chloroethyl)piperidine hydrochloride instead of 1-(3-chloropropyl)piperidine hydrochloride to give desired compound as a light yellow paste (yield 19%). MS (ESI) m/z 391 (M+H$^+$). $^1$H NMR (CDCl$_3$) δ 8.36 (1H, s), 8.06 (1H, s), 7.81 (2H, d, J=8.8 Hz), 7.67 (1H, d, J=8.4 Hz), 7.58 (1H, d, J=2.1 Hz), 7.47 (1H, d, J=7.8 Hz). 7.34 (1H, t, J=7.8 Hz), 6.87 (2H, d, J=8.8 Hz), 6.58 (1H, d, J=2.1 Hz), 4.14 (2H, t, J=6.0 Hz), 2.83 (2H, t, J=6.0 Hz), 2.58 (4H, m), 1.64 (4H, m), 1.46 (2H, m). $^{13}$C NMR (Acetone-d$_6$) δ 164.83, 140.00, 134.73, 133.93, 129.37, 128.78, 127.58, 126.28, 121.73, 120.58, 119.16, 117.18, 114.17, 101.78, 66.34, 57.24, 54.53, 25.34, 23.69.

Example 8: N-(3-(1H-pyrazol-5-yl)phenyl)-3-(3-(piperidin-1-yl)propoxy)benzamide (LLM45)

Tert-butyl 5-(3-(3-acetoxybenzamido)phenyl)-1H-pyrazole-1-carboxylate (6). Under similar conditions as described in the preparation of compound 4, but using 3-acetoxybenzoic acid instead of 4-acetoxybenzoic acid to give compound 6 as a white solid (yield 29%).

Tert-butyl 5-(3-(3-hydroxybenzamido)phenyl)-1H-pyrazole-1-carboxylate (7). Under similar conditions as described in the preparation of compound 5, compound 7 was obtained as a white solid (yield 82%). $^1$H NMR (DMSO-d$_6$) δ 10.30 (1H, s), 8.33 (2H, m), 7.88 (1H, d, 8.1 Hz), 7.60 (1H, d, 9.3 Hz), 7.44 (2H, m), 7.36 (2H, m), 6.97 (2H, m), 1.62 (9H, s).

N-(3-(1H-pyrazol-5-yl)phenyl)-3-(3-(piperidin-1-yl)propoxy)benzamide (LLM45). Compound 7 was reacted under similar conditions as described in the preparation of LLM41 to give LLM45 as a light yellow paste (yield 21%). MS (ESI) m/z 405 (M+H$^+$). $^1$H NMR (CDCl$_3$) δ 8.20 (1H, s), 8.10 (1H, m), 8.09 (1H, d, J=3 Hz), 7.92 (1H, q, J1=8.1 Hz, J2=1.5 Hz), 7.67 (1H, m), 7.34-7.46 (4H, m). 7.06 (1H, m), 6.75 (1H, d, J=3 Hz), 4.10 (2H, t, J=6.3 Hz), 2.63-2.72 (6H, m), 2.13 (2H, m), 1.71 (4H, m), 1.49 (2H, m). $^{13}$C NMR (DMSO-d$_6$) δ 165.33, 158.78, 146.36, 140.372, 136.63, 134.05, 132.37, 130.07, 122.34, 121.37, 120.44, 118.32, 116.64, 116.58, 113.87, 106.12, 68.38, 57.15, 30.97, 26.25, 24.37.

Example 9: N-(3-(1H-pyrazol-5-yl)phenyl)-3-(2-(piperidin-1-yl)ethoxy)benzamide (LLM46)

Compound 7 was reacted under similar conditions as described in the preparation of LLM41, but using 1-(2-chloroethyl)piperidine hydrochloride instead of 1-(3-chloropropyl)piperidine hydrochloride to give compound LLM46 as a light yellow paste (yield 31%). MS (ESI) m/z 391 (M+H$^+$). $^1$H NMR (CDCl$_3$) δ 8.38 (1H, s), 8.09 (1H, t, J=2.0 Hz), 8.06 (1H, d, J=2.8 Hz), 7.87 (1H, q, J1=8.4 Hz, J2=1.2 Hz), 7.65 (1H, d, J=8.4 Hz), 7.32-7.47 (4H, m). 7.05 (1H, q, J1=8.4 Hz, J2=2.0 Hz), 6.71 (1H, d, J=2.8 Hz), 4.16 (2H, t, J=6.0 Hz), 2.79 (2H, t, J=6.0 Hz), 2.52 (4H, m), 1.61 (4H, m), 1.43 (2H, m). $^{13}$C NMR (DMSO-d$_6$) δ 165.70, 162.78, 147.52, 140.10, 136.52, 133.42, 132.45, 130.04, 129.60, 122.17, 121.55, 120.50, 118.33, 118.21, 114.02, 107.17, 66.13, 57.69, 54.80, 27.96, 25.88.

Example 10: 1-(3-(1H-pyrazol-5-yl)phenyl)-3-(3-(3-(piperidin-1-yl)propyl)phenyl)urea (LLM413)

Tert-butyl 5-(3-(3-(3-(benzyloxy)phenyl)ureido)phenyl)-1H-pyrazole-1-carboxylate (8). 3-(benzyloxy)aniline (2.54 mmol) was dissolved in 10 ml THF. To the solution was added triphosgene (1.015 mmol) and DIEA (6.35 mmol) and stirred at 0° C. for 15 min, then compound 3a (2.54 mmol) was added and the reaction mixture was stirred at room temperature for another 1 h. After the reaction was done, 100 ml EA and 100 ml water was added to quench the reaction. The organic layer was separated and washed with brine (50 ml×3). Solvent was removed through rotary evaporator under reduced pressure to give crude product, which was further purified by recrystallization from EtOH:H$_2$O (1:1) to afford a white solid (yield 53%). $^1$H NMR (CDCl$_3$) δ 8.07 (1H, d, J=2.8 Hz), 7.74 (1H, t, J=1.8 Hz), 7.53 (1H, s), 7.51 (1H, s), 7.30-7.42 (8H, m), 7.13-7.21 (3H, m). 6.89 (1H, q, J1=8.4 Hz, J2=1.8 Hz), 6.71 (1H, d, J=7.2 Hz), 6.68 (1H, d, J=2.8 Hz), 5.03 (2H, s), 1.67 (9H, s).

Tert-butyl 5-(3-(3-(3-hydroxyphenyl)ureido)phenyl)-1H-pyrazole-1-carboxylate (9). Compound 8 (1.34 mmol) and palladium on charcoal (10%, 20 mg) were suspended in EtOH and heated to reflux. Ammonium formate (13.4 mmol) was added in two portions in two hours. After the reaction was done, the reaction mixture was immediately filtered when hot. The liquid was condensed with rotary evaporator under reduced pressure and re-dissolved in 300 ml EA. Then the organic layer washed with brine (100 ml×3) and dried with anhydrous Na$_2$SO$_4$ and evaporated to dryness under reduced pressure to give crude product, which was future purified by flash silica gel column chromatography (EA:hexanes=1:2) to give a white solid (yield 84%). $^1$H NMR (CDCl$_3$) δ 7.77 (1H, d, J=3.0 Hz), 7.74 (1H, s), 7.72 (1H, s), 7.70 (1H, s), 7.32 (1H, d, J=7.8 Hz), 7.17 (1H, d, J=9.3 Hz), 7.05 (1H, t, J=7.8 Hz). 6.91 (1H, t, J=7.8 Hz), 6.84 (1H, m), 6.70 (1H, d, J=9.3 Hz), 6.43 (1H, q, J1=8.1 Hz), 1.62 (9H, s).

1-(3-(1H-pyrazol-5-yl)phenyl)-3-(3-(3-(piperidin-1-yl)propoxy)phenyl)urea (LLM413). Compound 9 was reacted under similar conditions as described in the preparation of LLM41 to give LLM413 as a light yellow paste (yield 27%). MS (ESI) m/z 420 (M+H$^+$). $^1$H NMR (CDCl$_3$) δ 9.01 (1H,$), 8.95 (1H, s), 8.07 (1H, s), 8.02 (1H, d, J=3 Hz), 7.47-7.53 (2H, m), 7.27 (1H, t, J=7.8 Hz), 6.70-7.12 (3H, m), 6.68 (1H, d, J=3.0 Hz), 6.35 (1H, m), 3.73 (2H, t, J=5.4 Hz), 2.90-2.96 (6H, m), 2.04-2.08 (2H, m), 1.79 (4H, m), 1.51 (2H, m). $^{13}$C NMR (CDCl$_3$) δ 159.43 155.66, 147.76, 139.97, 139.40, 136.33, 132.42, 130.78, 129.71, 129.25, 121.21, 120.39, 117.71, 112.71, 109.89, 106.83, 85.66, 55.84, 54.41, 27.98, 25.99, 23.80.

Example 11: 1-(3-(1H-pyrazol-5-yl)phenyl)-3-(3-(2-(piperidin-1-yl)ethoxy)phenyl)urea (LLM414)

Compound 9 was reacted under similar conditions as described in the preparation of LLM41, but using 1-(2-chloroethyl)piperidine hydrochloride instead of 1-(3-chloropropyl)piperidine hydrochloride to give compound LLM414 as light yellow paste (yield 19%). MS (ESI) m/z 406 (M+H$^+$). $^1$H NMR (CDCl$_3$) δ 8.05 (1H, d, J=3.0 Hz), 7.85 (1H, s), 7.73 (1H, s), 7.69 (1H, s), 7.50-7.54 (2H, m), 7.30 (1H, t, J=6.8 Hz), 7.13 (1H, t, J=6.8 Hz), 6.95-6.98 (2H, m), 6.67 (1H, d, J=3.0 Hz), 6.54-6.57 (1H, m), 4.06 (2H, t, J=3.8 Hz), 2.82 (2H, t, J=3.8 Hz), 1.64 (4H, m), 1.44 (2H, m). $^{13}$C NMR (DMSO-d$_6$) δ 159.44, 155.02, 146.33, 139.77, 138.89, 136.62, 133.86, 131.37, 129.51, 129.17, 121.05, 120.46, 118.30, 112.68, 108.27, 102.96, 85.52, 55.84, 53.13, 24.37, 23.49.

Example 12: N-(3-(1H-pyrazol-5-yl)phenyl)-3-(piperidin-1-yl)benzamide (LLM437)

Tert-butyl 5-(3-(3-(piperidin-1-yl)benzamido)phenyl)-1H-pyrazole-1-carboxylate (10a). Compound 3a (0.43 mmol) was condensed with 3-(piperidin-1-yl)benzoic acid (0.43 mmol) under similar conditions as described in the preparation of compound 4 to afford 10a as a yellow solid (yield 35%). $^1$H NMR (CDCl$_3$) δ 8.09 (1H, d, J=2.8 Hz), 8.05 (1H, t, J=2.2 Hz), 7.90-7.94 (2H, m), 7.65 (1H, d, J=7.6 Hz), 7.46 (1H, t, J=2.0 Hz), 7.43 (1H, t, J=7.6 Hz), 7.35 (1H, t, J=7.6 Hz), 7.22 (1H, d, J=7.6 Hz), 7.10 (1H, q, J1=7.6 Hz, J2=2.2 Hz), 6.75 (1H, d, J=2.8 Hz), 3.25 (4H, t, J=4.2 Hz), 1.72 (4H, m), 1.66 (9H, s), 1.62 (2H, m).

Tert-butyl 5-(3-(3-(piperidin-1-ylmethyl)benzamido)phenyl)-1H-pyrazole-1-carboxylate (10b). Compound 3a (0.43 mmol) was condensed with 3-(piperidin-1-ylmethyl)benzoic acid (0.43 mmol) under similar conditions as described in the preparation of compound 4 to afford 10b as a light yellow solid (yield 37%). $^1$H NMR (CDCl$_3$) δ 8.15 (1H, t, J=2.4 Hz), 8.08 (1H, d, J=2.7 Hz), 8.00 (1H, s), 7.83-7.87 (1H, m), 7.67-7.70 (1H, m), 7.38-7.47 (3H, m), 7.04 (1H, s), 6.87 (1H, s), 6.74 (1H, d, J=2.7 Hz), 3.65 (2H, s), 2.52 (4H, s), 1.62-1.66 (13H, m), 1.47 (2H, m).

N-(3-(1H-pyrazol-5-yl)phenyl)-3-(piperidin-1-yl)benzamide (LLM437). Compound 10b (0.15 mmol) was dissolved in 2 ml 1.25 M hydrogen chloride methanol solution and heated to 50° C. and maintained at that temperature for 30 min. 30 ml water was added to reaction mixture and the pH of solution was adjusted to 7 by adding 2 M sodium bicarbonate drop-wise. The aqueous solution was extracted with dichloromethane (30 ml×3), and then the organic layer was dried with Na$_2$SO$_4$ and evaporated to dryness under reduced pressure to give crude product, which was future purified by preparative layer chromatography (MeOH:DCM=1:12) to give a light yellow solid (yield 75%). MS (ESI) m/z 347 (M+H$^+$). $^1$H NMR (CD$_3$OD) δ 8.42 (1H, s), 8.38 (1H, t, J=3.0 Hz), 8.30 (1H, d, J=2.7 Hz), 8.19 (1H, d, J=7.8 Hz), 7.98 (1H, m), 7.90 (1H, d, J=7.8 Hz), 7.79 (1H, t, J=8.1 Hz), 7.57-7.67 (2H, m), 7.13 (1H, d, J=2.7 Hz), 3.77 (4H, t, J=5.4 Hz), 2.12 (4H, m), 1.85 (2H, m). $^{13}$C NMR (CD$_3$OD) δ 166.63, 149.06, 143.73, 140.75, 138.45, 136.27, 131.96, 131.20, 130.53, 128.50, 125.72, 124.30, 123.92, 122.19, 120.29, 101.23, 58.48, 24.75, 22.06.

Example 13: N-(3-(1H-pyrazol-5-yl)phenyl)-3-(piperidin-1-ylmethyl)benzamide (LLM438)

The Boc group on LLM438 was removed as similar conditions as described in the preparation of LLM437 to afford LLM438 as light yellow paste (yield 62%). MS (ESI) m/z 361 (MH+). $^1$H NMR (DMSO-d$_6$) δ 10.79 (1H, s), 10.51 (1H, S), 8.34 (1H, s), 8.32 (1H, s), 8.03 (1H, d, J=8.0 Hz), 7.82-7.84 (3H, m), 7.57-7.60 (2H, m), 7.41 (1H, t, J=7.8 Hz), 6.71 (1H, d, J=2.0 Hz), 4.36 (2H, s), 3.29 (2H, m), 2.90 (2H, m), 1.68-1.87 (6H, m). $^{13}$C NMR (DMSO-d$_6$) δ 165.64, 148.41, 139.99, 135.57, 134.89, 132.86, 131.52, 131.51, 130.50, 129.53, 129.38, 129.03, 121.43, 120.28, 117.94, 102.74, 59.28, 52.25, 22.54, 21.89.

Example 14: N-(2-(1H-pyrazol-5-yl)phenyl)-4-(3-(piperidin-1-yl)propoxy)benzamide (LLM417)

Tert-butyl 5-(2-(4-acetoxybenzamido)phenyl)-1H-pyrazole-1-carboxylate (11). Compound 3b (11.62 mmol) was condensed with 4-acetoxybenzoic acid (11.62 mmol) under similar conditions as described in the preparation of compound 4 to afford compound 11 as white solid (yield 37%). $^1$H NMR (CDCl$_3$) δ 8.95 (1H, q, J1=8.4 Hz, J2=1.2 Hz), 8.43 (2H, m), 8.10 (1H, d, J=4.0 Hz), 7.70 (1H, q, J1=10.4 Hz, J2=2.0 Hz), 7.45 (1H, m), 7.27 (2H, m), 7.17 (1H, m), 6.83 (1H, d, J=4.0 Hz), 2.34 (3H, s), 1.68 (9H, s).

Tert-butyl 5-(2-(4-hydroxybenzamido)phenyl)-1H-pyrazole-1-carboxylate (12). Under similar conditions as described in the preparation of compound 5, compound 12 was obtained as a white solid (yield 78%). $^1$H NMR (Acetone-d$_6$) δ 8.93 (1H, q, J1=8.4 Hz, J2=1.2 Hz), 8.05 (2H, m), 7.95 (1H, d, J=4.0 Hz), 7.86 (1H, q, J1=10.4 Hz, J2=2.0 Hz), 7.33 (1H, m), 7.13 (1H, m), 6.96 (2H, m), 6.91 (1H, d, J=4.0 Hz), 1.66 (9H, s).

N-(2-(1H-pyrazol-5-yl)phenyl)-4-(3-(piperidin-1-yl)propoxy)benzamide (LLM417). Compound 12 was reacted under similar conditions as described in the preparation of LLM41 to give LLM417 as a light yellow paste (yield 21%). MS (ESI) m/z 405 (M+H$^+$). $^1$H NMR (CDCl$_3$) δ 12.11 (1H, s), 8.80 (1H, d, J=7.8 Hz), 8.00 (2H, m), 8.10 (1H, d, J=8.7 Hz), 7.65 (1H, m), 7.45 (1H, s), 7.33 (1H, t, J=7.2 Hz), 7.12 (1H, t, J=7.2 Hz), 6.95 (2H, d, J=8.7 Hz), 6.64 (1H, d, J=2.4 Hz), 4.24 (2H, t, J=6.3 Hz), 3.26 (6H, m), 2.09 (2H, m), 1.62 (4H, m), 1.43 (2H, m). $^{13}$C NMR (Acetone-d$_6$) δ 165.78, 161.60, 151.94, 138.08, 132.08, 130.30, 128.87, 128.37, 128.09, 123.57, 121.10, 116.30, 115.29, 104.48, 56.02, 54.91, 50.87, 27.87, 26.20, 24.80.

Example 15: N-(2-(1H-pyrazol-5-yl)phenyl)-4-(2-(piperidin-1-yl)ethoxy)benzamide (LLM418)

Compound 12 was reacted under similar conditions as described in the preparation of LLM41, but using 1-(2-chloroethyl)piperidine hydrochloride instead of 1-(3-chloropropyl)piperidine hydrochloride to give compound LLM418 as a light yellow paste (yield 18%). MS (ESI) m/z 391 (M+H$^+$). $^1$H NMR (DMSO-d$_6$) δ 13.40 (1H, s), 12.47 (1H, s), 8.71 (1H, d, J=8.1 Hz), 7.86-8.02 (4H, m), 7.31 (1H, t, J=7.2 Hz), 7.10-7.24 (3H, m), 6.90 (2H, s), 4.17 (2H, t, J=6.0 Hz), 2.70 (2H, t, J=6.0 Hz), 2.45 (4H, m), 1.50 (4H, m), 1.39 (2H, m). $^{13}$C NMR (DMSO-d$_6$) δ 164.79, 161.74, 150.72, 150.53, 136.80, 130.56, 129.64, 128.32, 127.59, 123.59, 120.86, 120.45, 115.04, 103.85, 66.40, 57.63, 54.84, 26.02, 24.36.

The following compounds can be prepared in a similar fashion as described in the preparation of LLM41:

N-(2-(4-oxoazetidin-2-yl)phenyl)-4-(2-(piperidin-1-yl)ethoxy)benzamide;
4-(2-(piperidin-1-yl)ethoxy)-N-(2-(4-thioxoazetidin-2-yl)phenyl)benzamide;
N-(2-(5-oxopyrrolidin-2-yl)phenyl)-4-(2-(piperidin-1-yl)ethoxy)benzamide;
4-(2-(piperidin-1-yl)ethoxy)-N-(2-(5-thioxopyrrolidin-2-yl)phenyl)benzamide;
N-(2-(6-oxopiperidin-2-yl)phenyl)-4-(2-(piperidin-1-yl)ethoxy)benzamide;
4-(2-(piperidin-1-yl)ethoxy)-N-(2-(6-thioxopiperidin-2-yl)phenyl)benzamide;
N-(2-(2-oxohexahydropyrimidin-4-yl)phenyl)-4-(2-(piperidin-1-yl)ethoxy)benzamide;
4-(2-(piperidin-1-yl)ethoxy)-N-(2-(2-thioxohexahydropyrimidin-4-yl)phenyl)benzamide;
N-(2-(2-oxoimidazolidin-4-yl)phenyl)-4-(2-(piperidin-1-yl)ethoxy)benzamide;
4-(2-(piperidin-1-yl)ethoxy)-N-(2-(2-thioxoimidazolidin-4-yl)phenyl)benzamide;
N-(2-(4-oxo-1,3-diazetidin-2-yl)phenyl)-4-(2-(piperidin-1-yl)ethoxy)benzamide;
4-(2-(piperidin-1-yl)ethoxy)-N-(2-(4-thioxo-1,3-diazetidin-2-yl)phenyl)benzamide;
N-(2-(1,2-oxazetidin-3-yl)phenyl)-4-(2-(piperidin-1-yl)ethoxy)benzamide;

N-(2-(1,2-thiazetidin-3-yl)phenyl)-4-(2-(piperidin-1-yl)ethoxy)benzamide;
N-(2-(isoxazolidin-3-yl)phenyl)-4-(2-(piperidin-1-yl)ethoxy)benzamide;
N-(2-(isothiazolidin-3-yl)phenyl)-4-(2-(piperidin-1-yl)ethoxy)benzamide;
N-(2-(1,2-oxazinan-3-yl)phenyl)-4-(2-(piperidin-1-yl)ethoxy)benzamide;
N-(2-(1,2-thiazinan-3-yl)phenyl)-4-(2-(piperidin-1-yl)ethoxy)benzamide;
N-(2-(5-methyl-2,6-dioxo-1,2,3,6-tetrahydropyrimidin-4-yl)phenyl)-4-(2-(piperidin-1-yl)ethoxy)benzamide;
N-(2-(2,6-dioxo-1,2,3,6-tetrahydropyrimidin-4-yl)phenyl)-4-(2-(piperidin-1-yl)ethoxy)benzamide;
N-(2-(5-oxopyrrolidin-3-yl)phenyl)-4-(2-(piperidin-1-yl)ethoxy)benzamide;
4-(2-(piperidin-1-yl)ethoxy)-N-(2-(5-thioxopyrrolidin-3-yl)phenyl)benzamide;
N-(2-(6-oxopiperidin-3-yl)phenyl)-4-(2-(piperidin-1-yl)ethoxy)benzamide;
4-(2-(piperidin-1-yl)ethoxy)-N-(2-(6-thioxopiperidin-3-yl)phenyl)benzamide;
N-(2-(5-oxo-2,5-dihydroisoxazol-3-yl)phenyl)-4-(2-(piperidin-1-yl)ethoxy)benzamide;
N-(3-(2,4-dioxo-1,2,3,4-tetrahydro-7H-pyrrolo[2,3-d]pyrimidin-7-yl)phenyl)-4-(2-(piperidin-1-yl)ethoxy)benzamide;
N-(2-(7-oxo-4,5,6,7-tetrahydro-1H-indol-2-yl)phenyl)-4-(2-(piperidin-1-yl)ethoxy)benzamide;
N-(2-(1H-pyrrolo[2,3-b]pyridin-2-yl)phenyl)-4-(2-(piperidin-1-yl)ethoxy)benzamide;
N-(3-(2,4-dioxo-1,2,3,4-tetrahydroquinazolin-8-yl)phenyl)-4-(2-(piperidin-1-yl)ethoxy)benzamide;
N-(3-(2,4-dioxo-1,2,3,4-tetrahydrofuro[3,2-d]pyrimidin-7-yl)phenyl)-4-(2-(piperidin-1-yl)ethoxy)benzamide;
N-(3-(2-oxo-2,3-dihydro-1H-benzo[d]imidazol-4-yl)phenyl)-4-(2-(piperidin-1-yl)ethoxy)benzamide;
N-(2-(4,7-dioxo-4,7-dihydro-1H-indol-3-yl)phenyl)-4-(2-(piperidin-1-yl)ethoxy)benzamide;
N-(2-(5,6-dimethyl-4,7-dioxo-4,7-dihydro-1H-indol-3-yl)phenyl)-4-(2-(piperidin-1-yl)ethoxy)benzamide;
N-(2-(7-oxo-4,5,6,7-tetrahydro-1H-indol-3-yl)phenyl)-4-(2-(piperidin-1-yl)ethoxy)benzamide;
N-(2-(4,7-dioxo-4,5,6,7-tetrahydro-1H-indol-3-yl)phenyl)-4-(2-(piperidin-1-yl)ethoxy)benzamide;
N-(2-(7-oxo-1,4,5,7-tetrahydropyrano[3,4-b]pyrrol-3-yl)phenyl)-4-(2-(piperidin-1-yl)ethoxy)benzamide;
N-(2-(7-oxo-4,5,6,7-tetrahydro-1H-pyrrolo[2,3-c]pyridin-3-yl)phenyl)-4-(2-(piperidin-1-yl)ethoxy)benzamide;
N-(2-(7-oxo-6,7-dihydro-1H-pyrrolo[2,3-c]pyridin-3-yl)phenyl)-4-(2-(piperidin-1-yl)ethoxy)benzamide;
N-(2-(7-oxo-1,7-dihydropyrano[3,4-b]pyrrol-3-yl)phenyl)-4-(2-(piperidin-1-yl)ethoxy)benzamide;
N-(2-(2-oxo-2,3-dihydro-1H-imidazol-4-yl)phenyl)-4-(2-(piperidin-1-yl)ethoxy)benzamide;
1-(2-(1H-pyrazol-5-yl)phenyl)-3-(3-(2-(piperidin-1-yl)ethoxy)phenyl)urea;
1-(2-(5-methyl-2,6-dioxo-1,2,3,6-tetrahydropyrimidin-4-yl)phenyl)-3-(3-(2-(piperidin-1-yl)ethoxy)phenyl)urea;
1-(2-(2,6-dioxo-1,2,3,6-tetrahydropyrimidin-4-yl)phenyl)-3-(3-(2-(piperidin-1-yl)ethoxy)phenyl)urea;
1-(2-(1H-pyrazol-5-yl)phenyl)-3-(4-(2-(piperidin-1-yl)ethoxy)phenyl)urea;
N-(2-(4-fluoro-1H-pyrazol-5-yl)phenyl)-4-(2-(piperidin-1-yl)ethoxy)benzamide;
N-(2-(3,4-difluoro-1H-pyrazol-5-yl)phenyl)-4-(2-(piperidin-1-yl)ethoxy)benzamide;
N-(2-(3-fluoro-1H-pyrazol-5-yl)phenyl)-4-(2-(piperidin-1-yl)ethoxy)benzamide;
N-(2-(4-chloro-1H-pyrazol-5-yl)phenyl)-4-(2-(piperidin-1-yl)ethoxy)benzamide;
N-(2-(3,4-dichloro-1H-pyrazol-5-yl)phenyl)-4-(2-(piperidin-1-yl)ethoxy)benzamide;
N-(2-(3-chloro-1H-pyrazol-5-yl)phenyl)-4-(2-(piperidin-1-yl)ethoxy)benzamide;
N-(2-(3-methoxy-1H-pyrazol-5-yl)phenyl)-4-(2-(piperidin-1-yl)ethoxy)benzamide;
5-(2-(4-(2-(piperidin-1-yl)ethoxy)benzamido)phenyl)-1H-pyrazol-3-yl acetate;
N-(2-(4-methoxy-1H-pyrazol-5-yl)phenyl)-4-(2-(piperidin-1-yl)ethoxy)benzamide;
5-(2-(4-(2-(piperidin-1-yl)ethoxy)benzamido)phenyl)-1H-pyrazol-4-yl acetate;
N-(2-(4-acetamido-1H-pyrazol-5-yl)phenyl)-4-(2-(piperidin-1-yl)ethoxy)benzamide;
N-(2-(4-(dimethylamino)-1H-pyrazol-5-yl)phenyl)-4-(2-(piperidin-1-yl)ethoxy)benzamide;
N-(2-(3-(dimethylamino)-1H-pyrazol-5-yl)phenyl)-4-(2-(piperidin-1-yl)ethoxy)benzamide;
N-(4-methyl-2-(1H-pyrazol-5-yl)phenyl)-4-(2-(piperidin-1-yl)ethoxy)benzamide;
N-(4,5-dimethoxy-2-(1H-pyrazol-5-yl)phenyl)-4-(2-(piperidin-1-yl)ethoxy)benzamide;
N-(4,5-dihydroxy-2-(1H-pyrazol-5-yl)phenyl)-4-(2-(piperidin-1-yl)ethoxy)benzamide;
N-(5-bromo-2-(1H-pyrazol-5-yl)phenyl)-4-(2-(piperidin-1-yl)ethoxy)benzamide;
4-(2-(piperidin-1-yl)ethoxy)-N-(2-(4-(trifluoromethyl)-1H-pyrazol-5-yl)phenyl)benzamide;
4-(2-(piperidin-1-yl)ethoxy)-N-(2-(3-(trifluoromethyl)-1H-pyrazol-5-yl)phenyl)benzamide;
N-(3,5-dibromo-2-(1H-pyrazol-5-yl)phenyl)-4-(2-(piperidin-1-yl)ethoxy)benzamide;
N-(3-bromo-2-(1H-pyrazol-5-yl)phenyl)-4-(2-(piperidin-1-yl)ethoxy)benzamide;
N-(2-(3-acetamido-1H-pyrazol-5-yl)phenyl)-4-(2-(piperidin-1-yl)ethoxy)benzamide;
N-(2-(3-amino-1H-pyrazol-5-yl)phenyl)-4-(2-(piperidin-1-yl)ethoxy)benzamide.

Cell Lines

Human breast cancer cell lines MCF7, MDA-MB-231 and SUM159 were maintained in Dulbecco's modified Eagle medium (DMEM). Human pancreatic cancer cell line BxPC-3 was maintained in RPMI 1640 medium. Human pancreatic cancer cell line Capan-1 was maintained in Iscove's Modified Dulbecco's Medium (IMEM). All media were supplemented with 10% FBS and 1% penicillin/streptomycin, and cells were incubated in a humidified 37° C. incubator with 5% $CO_2$. PE/CA-PJ49 cell line was purchased from external sources and maintained according to manufacturer's protocol.

Cell Viability Assay

Cell viability was evaluated by using the MTT assay in triple replicates in one experiment and repeated for three times. Cancer cells were seeded in 96-well plates at a density of 3,000 cells per well. The cells were incubated at 37° C. for a period of 24 hours. Escalating concentrations of IL-6/gp130 inhibitors were added in triplicate to the plates in the presence of 10% FBS. After incubation for 48 or 72 hours, a stock solution of MTT (0.5 mg/ml) was then added to each well containing the treated cells, followed by incubation at 37° C. for 3 h. After removal of medium, the MTT dye was dissolved with spectrophotometric grade DMSO and the absorbance was read at 570 nm. The $IC_{50}$ value is determined by interpolation based on the absorbance value halfway between positive and negative controls. In the experiment of LLM4 showing higher efficacy in cancer cells with higher levels of IL-6, instead of using medium with 10% FBS, DMEM with 0% FBS was used in order to eliminate the influence of trace amounts of growth factors and cytokines in FBS.

General Procedure for Western Blot Assays

Cells were harvested and lysed in cold radioimmunoprecipitation assay (RIPA) lysis buffer containing proteasome inhibitor cocktail and phosphatase inhibitor cocktail. The protein concentrations were determined using the BCA Protein Assay kit. After adding the loading buffer and boiling at 95° C. for 10 minutes, equivalent amounts of proteins were loaded on and separated by SDS-PAGE, and then were transferred to PVDF membranes. Membranes were probed with primary antibodies (1:1000) against phospho-STAT3 (Tyr705), STAT3, phospho-STAT1 (Tyr701), STAT1, phospho-STAT6 (Tyr 641), STAT6, and GAPDH, respectively, and horseradish peroxidase (HRP)-conjugated secondary antibody (1:10000) (Cell Signaling Technology, Beverly, Mass.). Membranes were analyzed using Enhanced Chemiluminescence Plus reagents and either scanned with the Storm Scanner (Amersham Pharmacia Biotech, Inc., Piscataway, N.J.) or imaged with ChemiDoc MP imaging system (Bio-Rad, Hercules, Calif.). For cytokine induction of STAT3 phosphorylation, MCF-7 breast cancer cells were seeded in 10 cm plates (1 million cells per plate) and allowed to adhere overnight followed by serum-starvation. The cells were then left untreated or treated with LLM-418 (5-20 μM or 15 μM as indicated). After designated hours, LLM-418 treated and untreated cells were stimulated by IL-6, LIF, and OSM (50 ng/mL). The cells were harvested after 30 minutes and analyzed by Western blot.

Western Blot Assay in BxPC-3 and SUM159 Cell Lines

BxPC-3 and SUM159 cells were seeded in 10 cm plates (1 million cells per plate) and allowed to adhere overnight. The cells were then left untreated or treated with LLM4 and MDL16 (5-20 μM) for 16 hours. Then cells were harvested and analyzed by western blotting.

Western Blot Assay in SUM159 Cell Line

SUM159 cells were seeded in 10 cm plates (1 million cells per plate) and allowed to adhere overnight. The cells were then left untreated or treated with LLM414 and LLM418 (1-4 μM) for 16 hours. Then cells were harvested and analyzed by western blotting.

Western Blot Assay in Cytokine Induction of STAT Phosphorylation

MCF7 breast cancer cells were seeded in 10 cm plates (1 million cells per plate) and allowed to adhere overnight. The following day, the cells were serum-starved. The cells were then left untreated or treated with LLM4 (5-20 μM). After designated hours, the LLM4 treated and untreated cells were stimulated by IL-6, LIF, OSM, CNTF, CT-1, IL-11, IL-4 or INF-γ (50 ng/ml). The cells were harvested after 30 minutes and analyzed by western blotting.

Drug Affinity Responsive Target Stability (DARTS) Assay

Human SUM159 breast cancer cells were lysed in cold radioimmunoprecipitation assay (RIPA) lysis buffer containing proteasome inhibitor cocktail and phosphatase inhibitor cocktail. Then lysates were incubated with escalating concentrations (10-1000 μM) of LLM418 or DMSO control at room temperature for 1 h. Proteolysis was followed by adding protease pronase solution at a ratio of 1 mg of pronase to 1000 mg (or 2000 mg) of lysate protein for 30 min, 20 min or 15 min at room temperature. To stop proteolysis, 4×SDS sample loading buffer was added at 1:3 ratio to each sample and boiled at 95° C. for 10 min. The resulted protein samples were separated by 8% SDS-PAGE gel and analyzed by western blotting.

Expression and Purification of gp130-D1-D3 Domains

DNA encoding the first three domains D1-D3 (residues 1-301, the numbering system is based on PDB 3L5H, which is the mature form of gp130) of the six ectodomains of human gp130 was cloned into a pFB-GTFH vector to produce the pFB-G-[gp130D1-D3]-TFH expression plasmid [Xu, Y.; Kershaw, N. J.; Luo, C. S.; Soo, P.; Pocock, M. J.; Czabotar, P. E.; Hilton, D. J.; Nicola, N. A.; Garrett, T. P.; Zhang, J. G., Crystal structure of the entire ectodomain of gp130: insights into the molecular assembly of the tall cytokine receptor complexes. *The Journal of biological chemistry* 2010, 285 (28), 21214-21218]. The gp130-D1-D3 protein was inserted between an N-terminal gp64 signal sequence, which encodes a baculovirus secretion signal peptide, and a C-terminal tandem TFH purification tag. Protein expression was carried out in the Bac-to-Bac® Baculovirus Expression System (Invitrogen™). The recombinant donor plasmid pFB-G-[gp130D1-D3]-TFH was transformed into DH10Bac™ *E. coli* and then used to produce the recombinant bacmid DNA according to the supplier's manual. The bacmid was used to transfect sf9 insect cells to generate the seed virus. The virus was amplified in sf9 cells to obtain high-titer viral stocks, which were used to infect Hi5 insect cells. The cells were infected at a cell density of 2×106 cells/ml and incubated at 27° C. for 60 hours. For purification, the medium supernatant was harvested and passed onto anti-FLAG M2 agarose (Sigma). The bound protein was eluted with 0.5 mg/ml of FLAG peptide, concentrated with a 10-kDa MWCO centrifugal concentrator (Millipore) and applied to a Superdex 200 column (GE Healthcare) in buffer composed of 20 mM Hepes and 100 mM NaCl at pH 7.4. The purity was verified by SDS-PAGE giving a single band. The function was verified by IL-6/IL-6R binding using SPR (vide infra).

SPR Binding Affinity Measurements—Immobilization Through Primary Amines on CM5 Chips The SPR experiments were performed on a Biacore X100 instrument (GE Healthcare) at 25° C. with buffer HBS-EP+ (10 mM HEPES, pH 7.4, 150 mM NaCl, 3 mM EDTA, and 0.05% P20). A CM5 chip was preconditioned with 100 mM H3PO4, 10 mM HCl, 0.1% SDS, 50 mM NaOH. Each solution was injected twice for 30 s at 30 μl/min. pH-Scouting for the gp130-D1-D3 (M.W. 37.5 kDa) protein was performed in 10 mM NaAc at pH 4.0, 4.5, 5.0, and 5.5. The gp130-D1-D3 protein was immobilized to 9775 RU in 10 mM NaAc at pH 5.0 with standard amine coupling. Five μl of protein at 5.0 mg/ml was used. The immobilization was performed at a flow rate of 5 μl/min and a contact time of 840 s. To prevent baseline shifting, the protein-immobilized CM5 chip was left in stand-by mode overnight before performing binding experiments.

SPR Binding Affinity Measurements—Immobilization Through Capture-Couple on NTA Chips This method, proposed by Rich et al [Rich, R. L.; Errey, J.; Marshall, F.; Myszka, D. G., Biacore analysis with stabilized G-protein-coupled receptors. *Analytical Biochemistry* 2011, 409 (2), 267-272], was used. The NTA chip was preconditioned with three one-minute pulses of 350 mM EDTA and then charged with 0.5 mM Ni$^{2+}$ for 3 minutes at 10 μl/min followed by an extra wash with HBS-EP+. After the chip was equilibrated in a running buffer of HBS-P+ (HBS-EP+ without EDTA), the surface was activated with 1:1 EDC:NHS solution for 5 minutes at a flow rate of 10 μl/min. After stabilization for two minutes, 0.3 mg/ml gp130-D1-D6-Fc-His (10974-H03H-20, Sino Biological Inc) was injected at a flow rate of 3 µl/min for 5 minutes for direct NTA capture followed by an extra wash with HBS-EP+. Ethanolamine was injected at a flow rate of 10 µl/min for 5 minutes to deactivate the surface. The immobilized signal was 5850 RU. The reference cell was preconditioned, activated, and then deactivated with amine coupling reagents following the same protocol applied in the protein-immobilized cell except that the surface was not charged with $Ni^{2+}$. The binding experiments on NTA chips were all carried out in HBS-P+ running buffer.

IL-6/IL-6R Binding Experiments

Protein binding experiments were performed in HBS-EP+ buffer. IL-6 and IL-6R (10395-HNAE and 10398-H08H respectively, Sino Biological Inc.) were mixed in a 1:1 ratio. The mixture was injected onto a gp130-D1-D3 immobilized surface at concentrations of 2.5, 7.4, 22.2, 66.7, 200 nM at a flow rate of 5 µl/min for 960 s and allowed to dissociate for 600 s. Three startup cycles were included. The surface was regenerated by using 10 mM glycine-HCl at pH 2.9 at a flow rate of 10 µl/min for 30 s.

Small Molecule Binding Experiments

Small molecule binding experiments were performed in HBS-EP+ buffer with 5% DMSO. Small molecules were diluted from 20 mM stock solutions in DMSO. The highest concentrations used for each molecule were: 100 µM for MDL-A (Santa Cruz Biotechnology), 50 µM for MDL-16, 25 µM for LS-1 and LH-44, and 5 µM for Bazedoxifene (Cayman), LLM-41, LLM-414, and LLM-418. The highest concentrations were then diluted by factors of 2 or 1.5 to give 6 or 7 concentrations for each molecule. Molecules were applied to the gp130-D1-D3 immobilized surface with a flow rate of 30 µl/min for 30 s and were allowed to dissociate for another 30 s. The surface was regenerated by using HBS-EP+ with 30% DMSO with a flow rate of 30 µl/min for 30 s. Three buffer blanks were included in each run for double referencing. Solvent correction series (HBS-EP+ with 5.4%, 5.2%, 5.0%, 4.8%, 4.6%, 4.4% DMSO) were included.

Data Processing

The X100 BIAevaluation software was used to subtract blank references and determine the equilibrium dissociation constant KD from the steady-state analysis. The theoretical binding Rmax was calculated according to equation (1) assuming the binding ratio between inhibitor and protein is 1:1. The KD was determined by linear regression with a fixed Rmax according to equation (2): KD is the slope of the linear equation after reciprocal transformation of equation (2). RI refers to the bulk refractive index, which is reflected as an offset on the y axis.

$$R_{max} = R_{immob} \frac{M.W._{small\ molecule}}{M.W._{protein}} \quad (1)$$

$$R_{eq} = \frac{[Ligand]R_{max}}{K_D + [Ligand]} + RI \quad (2)$$

Biological Results

Cell Viability Assay Results for LLM3-LLM7

Firstly, the inhibitory effects of these novel compounds were tested on the human breast cancer cell line SUM159 which expresses elevated levels of IL-6 [Li H, Xiao H, Lin L, et al. Drug design targeting protein-protein interactions (PPIs) using multiple ligand simultaneous docking (MLSD) and drug repositioning: discovery of raloxifene and bazedoxifene as novel inhibitors of IL-6/gp130 interface. *J Med Chem*, 2014, 57, 632-641; Liu A, Liu Y, Jin Z, et al. XZH-5 inhibits STAT3 phosphorylation and enhances the cytotoxicity of chemotherapeutic drugs in human breast and pancreatic cancer cells. *PLoS ONE* 2012, 10, e46624]. The $IC_{50}$ values of these compounds are shown in Table 2. Compounds bearing the piperidine ring were superior in inhibiting SUM159 cancer cell growth compared to those with phenyl rings. LLM4 was the most potent compound, which was also predicted from its greater binding energy from the docking results. The most potent compound LLM4 was further tested in IL-6 elevated pancreatic cancer cell line BxPC-3 and Capan-1. This compound displayed $IC_{50}$ values of 3.9 µM and 35.1 µM, respectively, against these cell lines.

TABLE 1

Compounds selected for synthesis and $IC_{50}$ values.

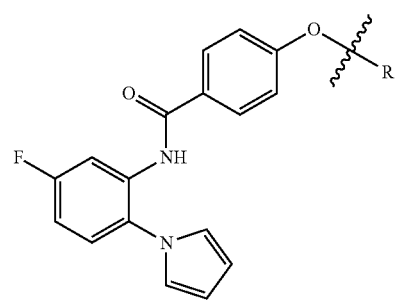

| compounds | R group | $IC_{50}^b$ |
|---|---|---|
| LLM3 | 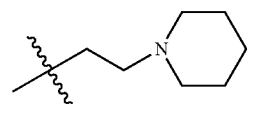 [SMILES: *CCN1CCCCC1] | 31.4 ± 4.7 |
| LLM4 | 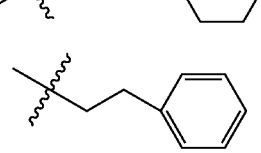 | 17.0 ± 5.5 |
| LLM5 | 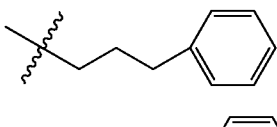 | 64.4 ± 6.9 |
| LLM6 | 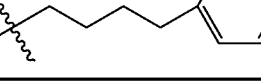 | 52.5 ± 7.6 |
| LLM7 | | 58.7 ± 6.3 |

Since the compounds were designed specifically to interfere with the IL-6 signaling pathway, it was expected that compounds should have higher potency in cancer cells expressing higher levels of IL-6. The breast cancer cell lines MCF7, MDA-MB-231 and SUM159, which express low, medium and high levels of IL-6, were chosen for this test. Prior to adding drug, the cells were serum-starved overnight to eliminate the influence of trace amounts of growth factors in FBS. MDL16, an inhibitor designed previously in our lab, and SC144 were compared. The $IC_{50}$ values of each compound in different breast cancer cells are shown in Table 3.

All three compounds show greater potency in cancer cells with higher levels of IL-6. However, LLM4 shows the most dramatic changes in IC$_{50}$ values in these three breast cancer cell lines, indicating it may be a more selective IL-6 inhibitor.

TABLE 3

IC$_{50}$ values of MDL16, LLM4 and SC144 in breast cancer cell lines MCF7, MDA-MB-231 and SUM159, which express low, medium and high levels of IL-6.

| drugs | $^a$IC$_{50}$ (μM) | | |
|---|---|---|---|
| | MCF7 | MDA-MB-231 | SUM159 |
| MDL16 | 7.3 | 6.07 | 2.67 |
| LLM4 | 4.51 | 0.97 | 0.04 |
| SC144 | 4.7 | 1.22 | 1.08 |

$^a$IC$_{50}$ values were tested at a drug incubation time of 48 h with 0% FBS medium.

Figure 2:
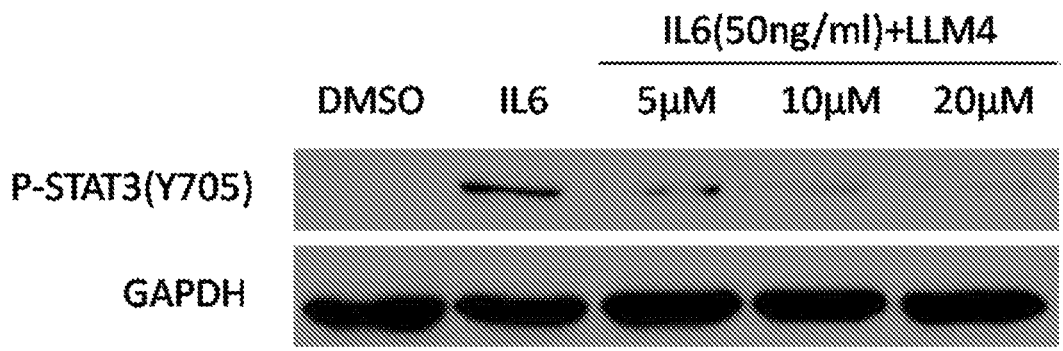
FIG. 2. depicts the inhibition of IL-6 induced STAT3 phosphorylation by LLM4 in the breast cancer cell line MCF7. The MCF7 cells were serum-starved overnight, then left untreated or treated with LLM4 (5-20 µM) for 5 h, followed by stimulation by IL-6 (50 ng/ml). The cells were harvested at 30 minutes and analyzed by western blot assay.

To examine whether LLM4 exerts its cancer inhibition through the IL-6/gp130 pathway, western blot assays were performed to detect the amount of phosphorylated STAT3 (P-STAT3), a main downstream protein of IL-6/gp130 signaling, after MCF7 cells were treated with LLM4 (5-20 μM) and induced with IL-6. As shown in FIG. 2, the amount of P-STAT3 stimulated by IL-6 in MCF7 cells decreased with increasing concentrations of compound LLM4. Significant reduction of phosphorylation of STAT3 induced by IL-6 was observed upon treatment with 10 LLM4. While treated at a concentration of 20 μM LLM4, almost complete inhibition of STAT3 phosphorylation was observed.

Figure 3:
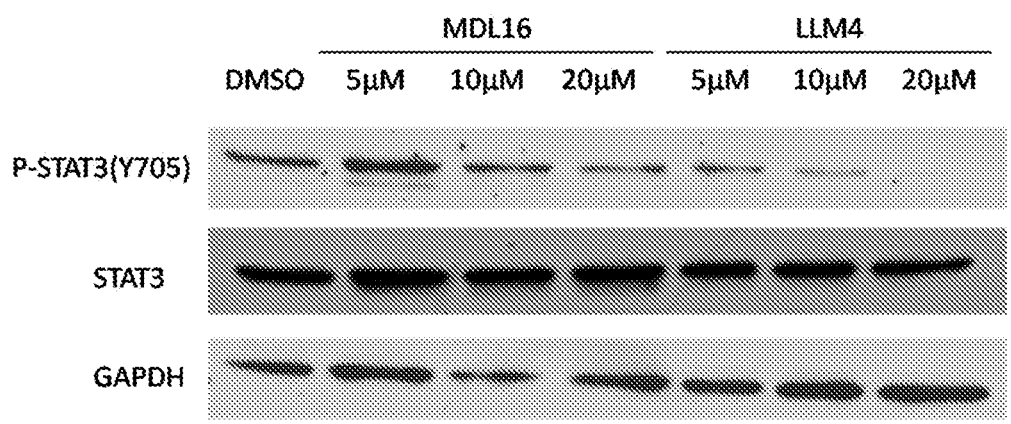
FIG. 3. depicts the inhibition of STAT3 phosphorylation by LLM4 in cancer cells with IL-6 autocrine effect in pancreatic cancer cell line BxPC-3. Cells were treated with MDL16 or LLM4 (5-20 µM) for 16 h, then cells were harvested and analyzed by western blot assay.
Figure 4:
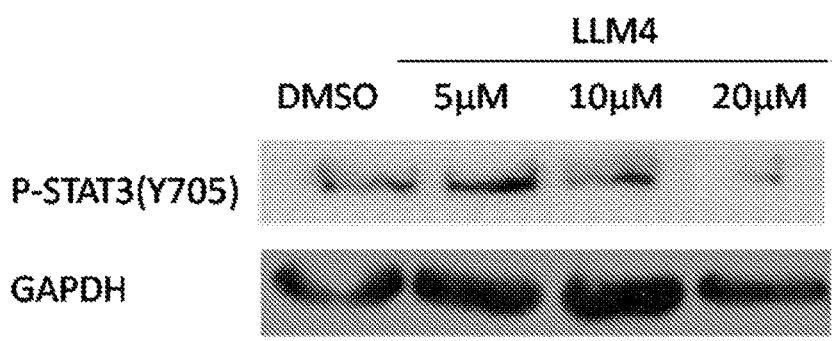
FIG. 4. depicts the inhibition of STAT3 phosphorylation by LLM4 in cancer cells with IL-6 autocrine effect in breast cancer cell line SUM159. Cells were treated with MDL16 or LLM4 (5-20 µM) for 16 h, then cells were harvested and analyzed by western blot assay.

After LLM4 was demonstrated to able to inhibit the IL-6 induced STAT3 phosphorylation in MCF7 cells, which express very low levels of IL-6, similar western blot assays were performed on cancer cells with an IL-6 autocrine effect. Here, IL-6 is consistently expressed at a high level, thus STAT3 is also consistently phosphorylated by endogenous IL-6. The pancreatic cancer cell line BxPC-3 and breast cancer cell line SUM159 were chosen for this test. As is shown in FIG. 3, both MDL16 and LLM4 inhibited STAT3 phosphorylation in BxPC-3 cells in a dose dependent manner. LLM4 showed better inhibition than that of MDL16, with almost complete inhibition at concentration of 20 μM. Inhibition of STAT3 phosphorylation by LLM4 in SUM159 cells was also tested and is shown in FIG. 4.

Other than IL-6, there are seven other members in the IL-6 family of cytokines, which are IL-11, leukemia inhibitory factor (LIF), oncostatin M (OSM), cardiotrophin-1 (CT-1), ciliary neurotrophic factor (CNTF), cardiotrophin-like cytokine (CLC) and IL-27 [White U A, Stephens J M. The gp130 receptor cytokine family: regulators of adipocyte development and function. Curr Pharm Des. 2011, 4, 340-346]. They are placed in one group because all of these cytokines require the signal receptor subunit gp130 in their signal transduction process, so they are also referred to as gp130 related cytokines. The crystal structure of IL-6 and LIF signaling complex were solved [Boulanger M J, Chow D C, Brevnova E E, et al. Hexameric structure and assembly of the interleukin-6/IL-6 alpha-receptor/gp130 complex. Science 2003, 300, 2101-2104; Boulanger M, Bankovich A, Kortemme T, et al. Convergent mechanisms for recognition of divergent cytokines by the shared signaling receptor gp130. Mol Cell 2003, 12, 577-589], and it is clear that IL-6 signaling requires the D1 domain of gp130 while LIF signaling doesn't. IL-11 is the only other IL-6 family cytokine requiring two gp130 proteins. Although the crystal structure of the IL-11 signaling complex is not solved yet, a 30 Å resolution cryoelectron microscopy (cryo-EM) structure of the IL-11/IL-11R/gp130 extracellular complex shows the similarity with IL-6/IL-6Rα/gp130 signaling complex [Rishi M, Hon W, John K, et al. The dynamics of signal triggering in a gp130-receptor complex. Structure 2007, 15, 441-448]. As a result, IL-6/gp130 interaction inhibitor LLM4 should influence the IL-6 (or may be IL-11) induced STAT3 phosphorylation, but not the others.

Figure 5:
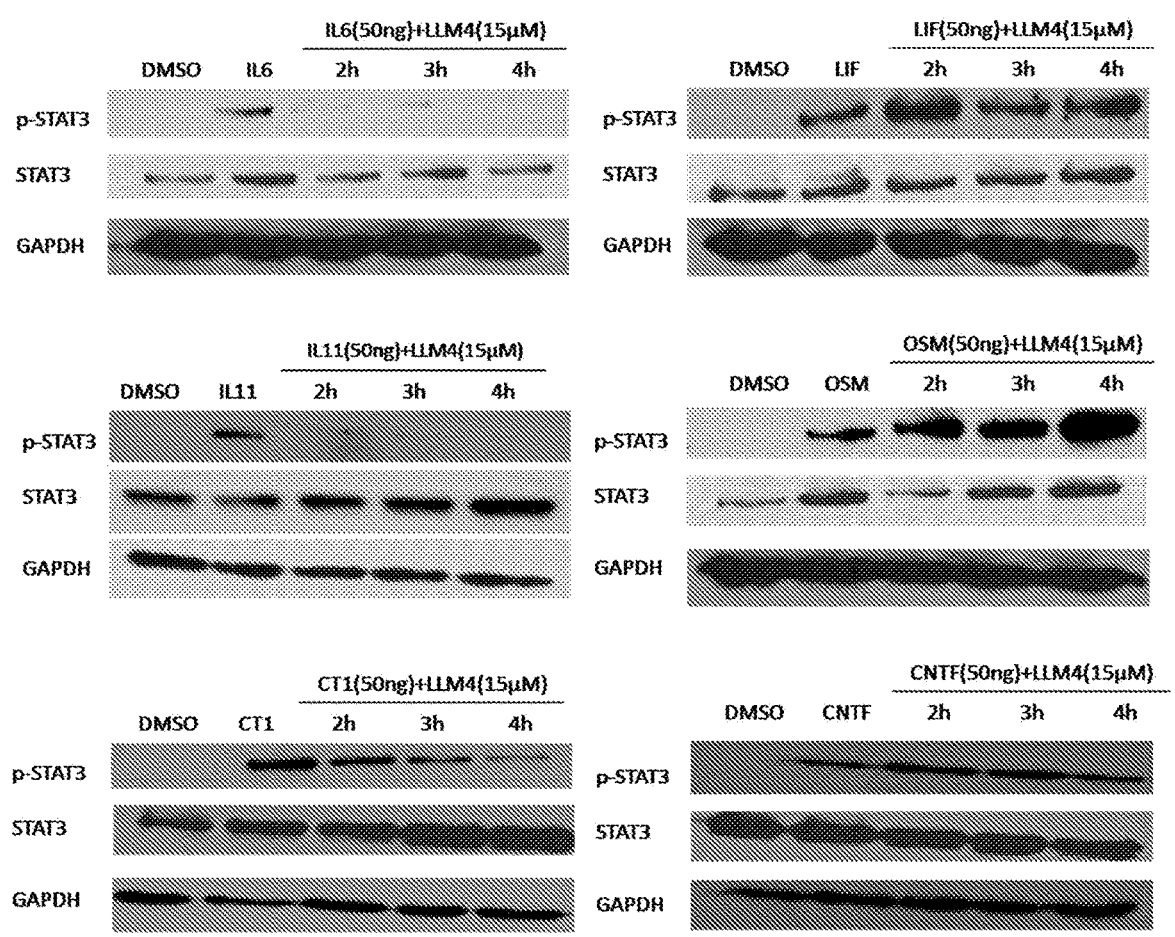
FIG. 5. depicts MCF7 cells with LLM4 (15 µM) for 2, 3 and 4 hours, followed by stimulation by IL-6 family cytokines (50 ng/ml). The cells were harvested at 30 minutes and analyzed by western blot assay.

The inhibitory effect of LLM4 in IL-6, LIF, OSM, CNTF, CT-1, IL-11 induced STAT3 phosphorylation in MCF7 cells was evaluated. MCF7 cells were treated with 15 μM LLM4 for 2, 3 and 4 hours, then these cytokines were used to induce STAT3 phosphorylation. The results are shown in FIG. 5. LLM4 was able to inhibit IL-6 induced STAT3 phosphorylation quite effectively at 15 μM. It not surprisingly to find LLM4 also inhibited IL-11 induced STAT3 phosphorylation since IL-11 signaling requires two gp130, in which the D1 domain of gp130 is involved. In LIF, OSM and CNTF induced STAT3 phosphorylation; they remain intact after LLM4 treatment for 2, 3 and 4 hours. This is consistent with the above hypothesis, since like LIF, OSM and CNTF signaling only require one gp130. The D1 domain is likely not involved in the signaling complex. Interestingly, LLM4 was also found to have a minor influence on the CT-1 induced STAT3 phosphorylation in a time dependent manner. This indicates the CT-1 signaling complex may also involve the D1 domain of gp130. It was reported that other than LIFR and gp130, CT-1 also recruits another a receptor with a molecular mass of 80 kDa, but this receptor is not yet identified [Robledo O, Fourcin M, Chevalier S, et al. Signaling of the cardiotrophin-1 receptor: evidence for a third receptor component. J Biol Chem 1997, 8, 4855-4863; Robledo O, Guillet C, Chevalier S. Hepatocyte-derived cell lines express a functional receptor for cardiotrophin-1. Eur Cytokine Netw. 1997, 8, 245-52]. According to these findings, the other a receptor may form an interaction with the gp130 D1 domain or force CT-1 to form some interaction with the gp130 D1 domain. Upon the binding of LLM4 to the gp130 D1 domain, this interaction would be disrupted.

Figure 6:
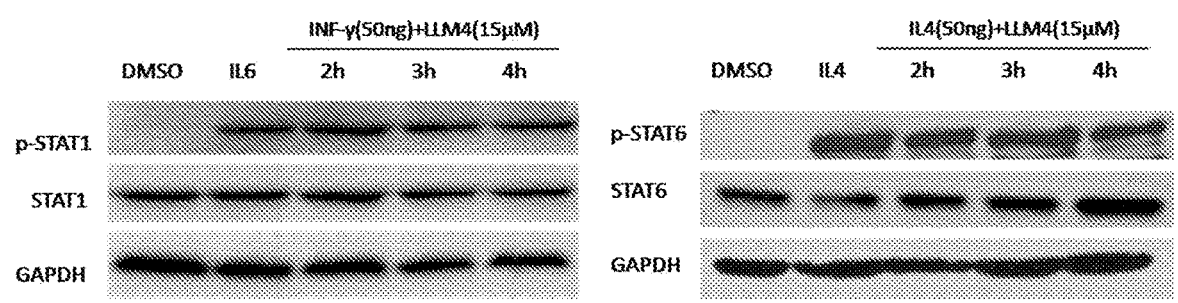
FIG. 6. depicts the treatment of serum-starved (overnight) MCF7 cells with LLM4 (15 µM) for 2, 3 and 4 hours.

There are seven members in STAT family, which are STAT1, STAT2, STAT3, STAT4, STAT5a, STAT5b and STAT6, mediating numerous cellular functions. As a relatively specific IL-6/gp130/STAT3 signaling pathway inhibitor, LLM4 should also have little effect on phosphorylation of other STATs. This is especially true of STAT1, since previous findings have shown its positive role in mediating the anti-tumor process. Here the inhibitory effect of LLM4 was tested in INF-γ induced STAT1 phosphorylation and IL-4 induced STAT6 phosphorylation [Hu X and Ivashkiv L. Cross-regulation of signaling and immune responses by IFN-γ and STAT1. Immunity 2009, 4, 539-550; Kaplan M H, Schindler U, Smiley S T, et al. Stat6 is required for mediating responses to IL-4 and for the development of Th2 cells. Immunity 1996, 4, 313-319]. The result is shown in FIG. 6. In MCF7 cells, the STAT1 and STAT6 phosphorylation levels were elevated by INF-γ and IL-4, respectively, whereas pre-treatment with LLM4 for 2, 3 and 4 hours showed no effect on the extent of STAT1 and STAT6 phosphorylation, indicating the good selectivity of LLM4.

Cell Viability Assay Results for LLM4/LH44 Hydrid Analogs

Figure 7:
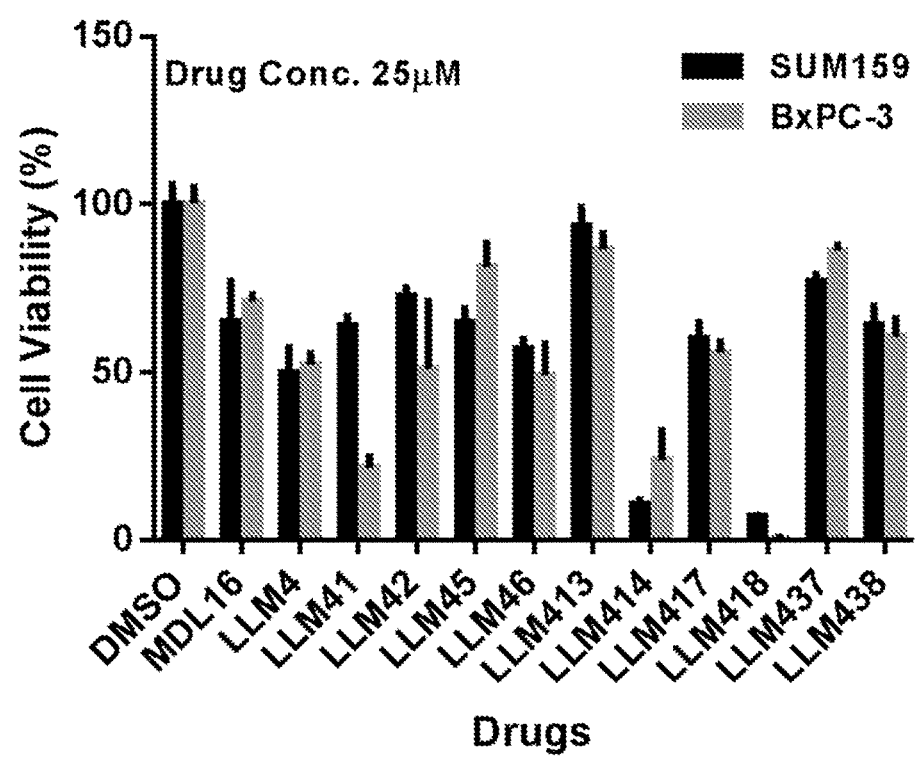
FIG. 7. depicts the inhibitory effects of various LLM compounds in SUM159 and BxPC-3 cell lines at concentration of 25 MDL16 and LLM4 were used as controls.

First the novel IL-6/gp130 inhibitors were tested in the SUM159 breast cancer cell line and in the BxPC-3 pancreatic cancer cell line at a concentration of 25 μM for an incubation time of 48 hours. The results are shown in FIG. 7. MDL16 and LLM4 were used as control compounds.

Compared to parent compound LLM4, compounds LLM41, LLM46 and LLM417 showed to be comparable or slightly better at inhibition, while compounds LLM414 and LLM418 showed greater inhibitory effect in both SUM159 and BxPC-3 cell lines. The $IC_{50}$ values of LLM414 and LLM418 were determined, and the result is shown in Table 4. LLM414 has $IC_{50}$ values of 2.8 µM and 8.3 µM against SUM159 and BxPC-3 cell lines, while LLM418 was even more potent, with $IC_{50}$ values of 1.7 µM and 1.2 µM respectively.

TABLE 4

$IC_{50}$ values of LLM414 and LLM418 in SUM159 and BxPC-3 cell lines.

| drugs | $IC_{50}$ (µM, 48 h) | |
| --- | --- | --- |
|  | SUM159 | BxPC-3 |
| MDL16 | 21.9 ± 3.9 | 15.6 ± 8.2 |
| LLM4 | 14.5 ± 3.5 | 10.9 ± 5.7 |
| LLM414 | 2.8 ± 1.9 | 8.3 ± 2.2 |
| LLM418 | 1.7 ± 0.7 | 1.2 ± 0.2 |

Figure 8:
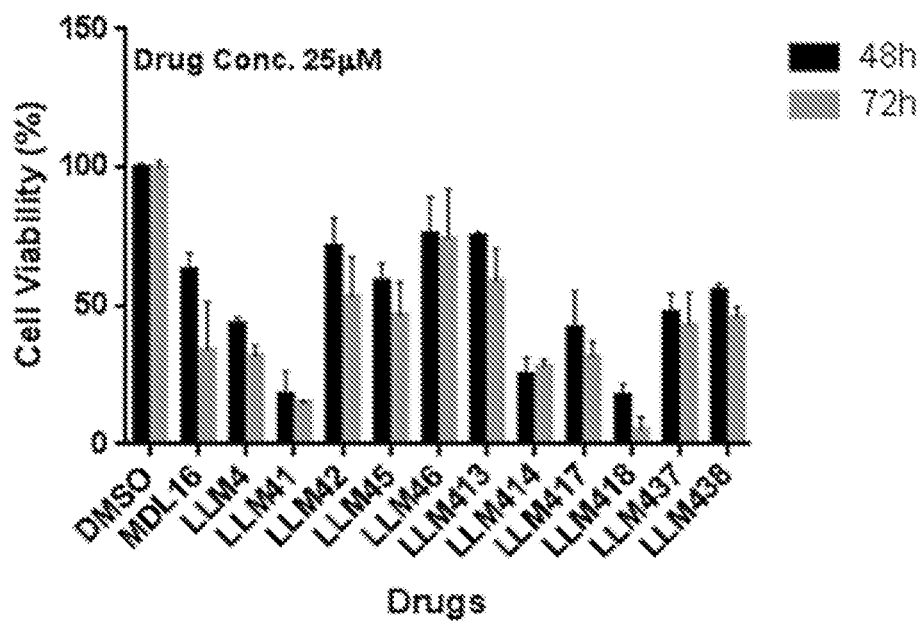
FIG. 8. depicts the inhibitory effects of various LLM compounds in a U266 cell line at concentration of 25 MDL16 and LLM4 were used as controls.

It was reported in multiple myeloma cell line U266 that IL-6 is also elevated and of great importance for cancer progression [Jernberg W, Pettersson M, Carlsson M, et al. Increase in interleukin 6 (IL-6) and IL-6 receptor expression in a human multiple myeloma cell line, U-266, during long-term in vitro culture and the development of a possible autocrine IL-6 loop 1. *Leukemia*. 1992, 4, 310-318]. These novel IL-6/gp130 inhibitors were tested in U266 cells at a concentration of 25 µM for an incubation time of 48 and 72 hours. The result is shown in FIG. 8. MDL16 and LLM4 were used as control compounds. Compared to the parent compound LLM4, compounds LLM41, LLM414, LLM418 showed greater inhibitory effects in U266 cells. The $IC_{50}$ values of LLM41, LLM414 and LLM418 were determined, and the result is shown in Table 5. LLM41, LLM414 and LLM418 have $IC_{50}$ values of 5.4 µM, 1.9 µM and 1.2 µM respectively.

TABLE 5

$IC_{50}$ values of LLM41, LLM414 and LLM418 in U266 cell line.

| drugs | $IC_{50}$ (µM, 72 h) |
| --- | --- |
| MDL16 | 15.8 ± 1.7 |
| LLM4 | 10.9 ± 1.5 |
| LLM41 | 5.4 ± 0.1 |
| LLM414 | 1.9 ± 0.8 |
| LLM418 | 1.2 ± 0.4 |

Figure 9:
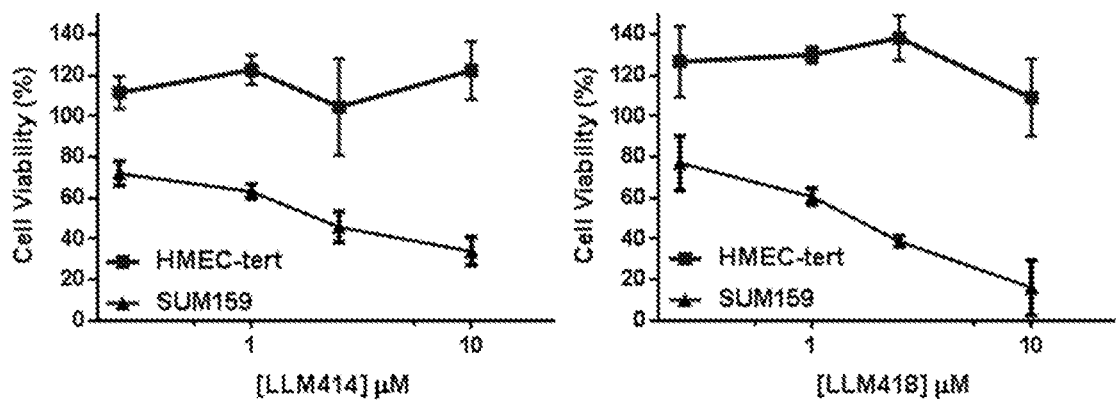
FIG. 9. depicts the cell viability of HMEC-tert and SUM159 after incubation with escalating concentrations (0.25-10 µM) of LLM414 and LLM418 for 48 hours.

To examine whether the novel compounds show cytotoxicity to normal cells, cell viability was also measured when the normal cell line tert-immortalized human mammaryepithelial cells (HMEC-tert) [Yang H, Pinello C E, Luo J, et al. Small-molecule inhibitors of acetyltransferase p300 identified by high-throughput screening are potent anticancer agents. *Mol Cancer Ther* 2013, 5, 610-620; Ferreira R B, Law M E, Jahn S C, et al. Novel agents that downregulate EGFR, HER2, and HER3 in parallel. *Oncotarget* 2015, 6, 10445-10457] were exposed to LLM414 and LLM418 and were compared to breast cancer cell line SUM159. The differential cytotoxic effects of LLM414 and LLM418 to HMEC-tert and SUM159 cells, as is shown in FIG. 9, suggest they selectively kill cancer cells.

Figure 10:
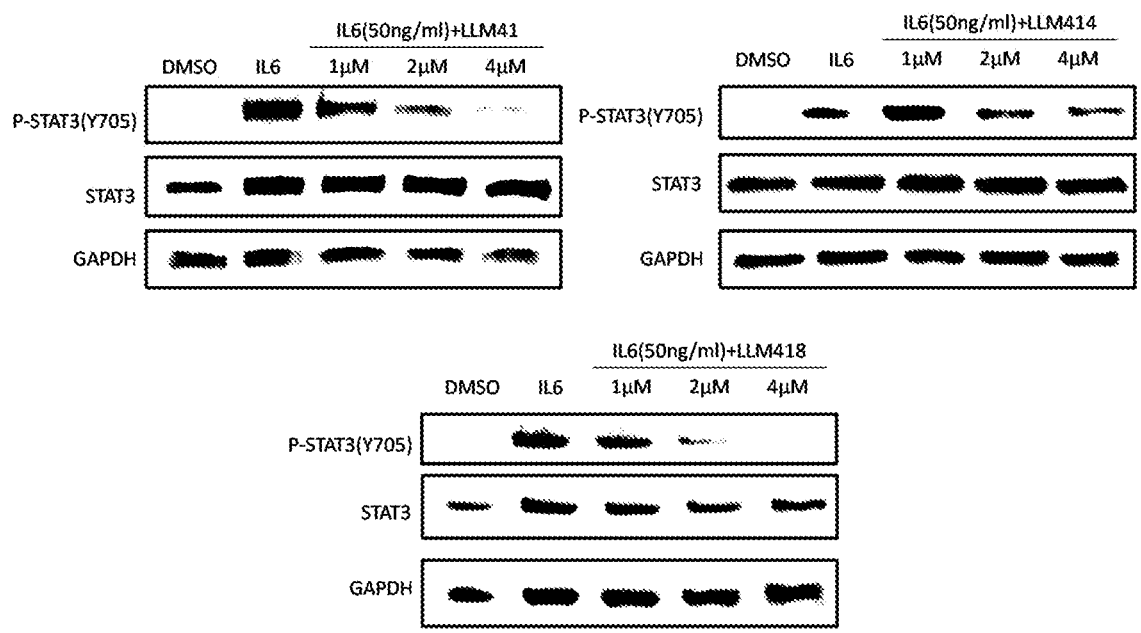
FIG. 10. depicts the inhibition of IL-6 induced STAT3 phosphorylation in breast cancer cell line MCF7 by LLM41 LLM414 and LLM418. The MCF7 cells were serum-starved overnight, then left untreated or treated with different concentrations of drugs (1-4 µM) for 5 h, followed by stimulation by IL-6 (50 ng/ml). The cells were harvested at 30 minutes and analyzed by western blot assays.

To examine whether LLM41, LLM414 and LLM418 exert the inhibition of cancer cells through the IL-6/gp130 pathway, western blot assays were performed to detect the amount of phosphorylated STAT3 (P-STAT3), a main downstream protein of IL-6/gp130 signaling, after MCF7 cells were treated with different concentrations of drugs (1-4 µM) and induced with IL-6. As is shown in FIG. 10, LLM41, LLM414 and LLM418 inhibited STAT3 phosphorylation stimulated by IL-6 in MCF7 cells in a dose dependent manner.

Figure 11:
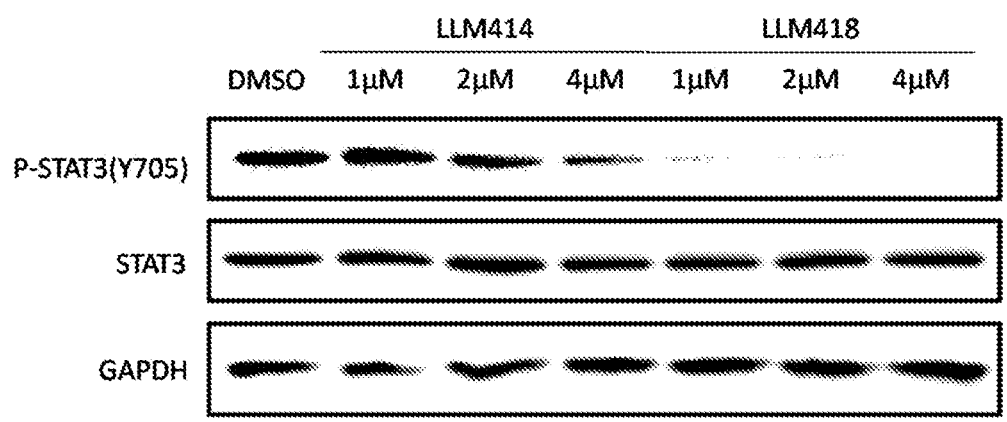
FIG. 11. depicts the inhibition of STAT3 phosphorylation in SUM159, a cancer cell line with IL-6 autocrine effect by LLM41 LLM414 and LLM418. Cells were treated with LLM414 or LLM418 (1-4 µM) for 16 h, then cells were harvested and analyzed by western blot assays.

LLM414 and LLM418 showed good inhibitory effects against SUM159 cells. Unlike MCF7, SUM159 has an IL-6 autocrine effect, which means IL-6 is consistently expressed at a high level, thus STAT3 is also consistently phosphorylated by endogenous IL-6 in SUM159. In this case, no exogenous IL-6 was needed to stimulate STAT3 phosphorylation. A similar western blot assay on SUM159 with LLM414 and LLM418 was performed and the result is shown in FIG. 11. Both LLM414 and LLM418 inhibited STAT3 phosphorylation in SUM159 cells and LLM418 showed stronger inhibition than LLM414.

Figure 12:
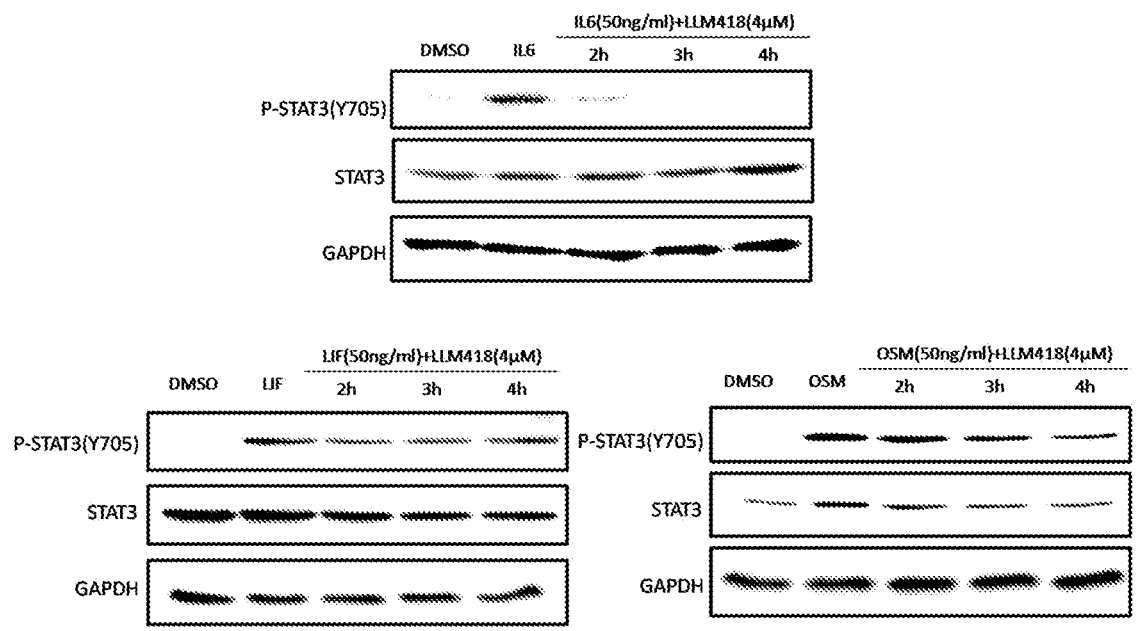
FIG. 12. depicts the specific inhibition of IL-6 induced STAT3 phosphorylation but not LIF and OSM induced STAT3 phosphorylation with by LLM418. The MCF7 cells were serum-starved overnight, then treated with LLM418 (4 µM) for 2, 3 and 4 hours, followed by stimulation by IL-6 family cytokines (50 ng/ml). The cells were harvested at 30 minutes and analyzed by western blot assays.

As is discussed above, IL-6 is a member of the IL-6 family of cytokines. There are seven other members in this family, which are IL-11, leukemia inhibitory factor (LIF), oncostatin M (OSM), cardiotrophin-1 (CT-1), ciliary neurotrophic factor (CNTF), cardiotrophin-like cytokine (CLC) and IL-27. They are placed in one group because all of these cytokines require gp130 in their signal transduction process, so they are also referred as gp130 related cytokines. The novel IL-6/gp130 inhibitors were designed to target the D1 domain of gp130, which is a quite unique binding site in IL-6 and IL-11 signaling. As a result, LLM418 should have little effect on the other IL-6 family of cytokine induced STAT3 phosphorylation. The inhibitory effect of LLM418 in LIF and OSM induced STAT3 phosphorylation were tested in MCF7 cells and the results are shown in FIG. 12. LLM418 was able to inhibit IL-6 induced STAT3 phosphorylation quite effectively at 4 µM, while in LIF and OSM induced STAT3 phosphorylation, LLM418 showed very little inhibitory effect, indicating the good selectivity of LLM418 towards IL-6/gp130 signaling.

Figure 13:
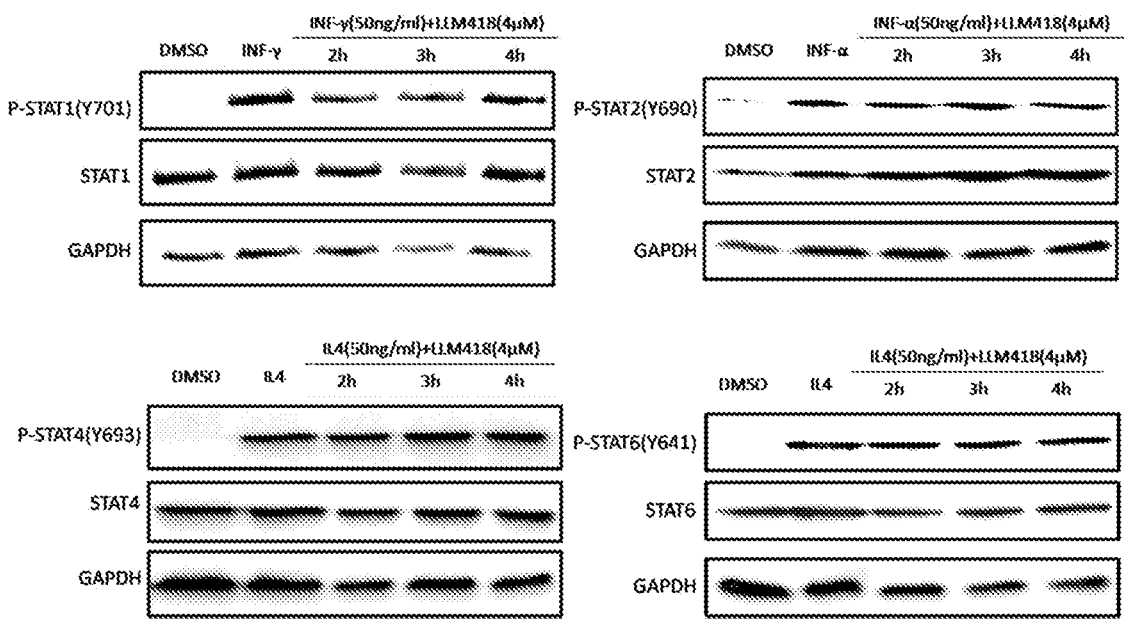
FIG. 13. depicts the reduced effect on STAT1, STAT2, STAT4 and STAT6 phosphorylation by LLM418. The MCF7 cells were serum-starved overnight, then treated with LLM4 (15 µM) for 2, 3 and 4 hours. STAT1, STAT2, STAT4 and STAT6 phosphorylation were induced by INF-γ, INF-α and IL-4, respectively. The cells were harvested at 30 minutes and analyzed by western blot assays.

There are seven members in the STAT family, which are STAT1, STAT2, STAT3, STAT4, STAT5a, STAT5b and STAT6, mediating numerous cellular functions. As a relatively specific IL-6/gp130/STAT3 signaling pathway inhibitor, LLM418 should have little effect on phosphorylation of other STATs. This is especially true of STAT1, since previous findings have shown its positive role in mediating the anti-tumor process. LLM418 inhibitory effect was tested in STAT1, STAT2, STAT4 and STAT6 phosphorylation. As is shown in FIG. 13, INF-γ, INF-α and IL4 induce the phosphorylation on STAT1, STAT2, STAT4 & STAT6, respectively. The pre-treatment of LLM418 showed little effect on the phosphorylation of these STATs, indicating the high specificity of LLM418 towards IL-6/STAT3 signaling pathway.

Figure 14:
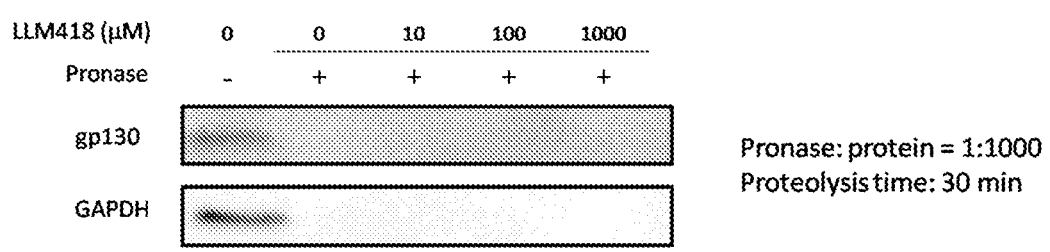
FIG. 14. depicts the confirmatory binding of LLM418 to gp130 in SUM159 breast cancer cell lysates using a 1:1000 ratio of pronase:protein with a proteolysis time of 30 minutes. These results suggest the direct binding of LLM418 to gp130 stabilizes its structure and therefore protects it from proteolytic digestion.
Figure 15:
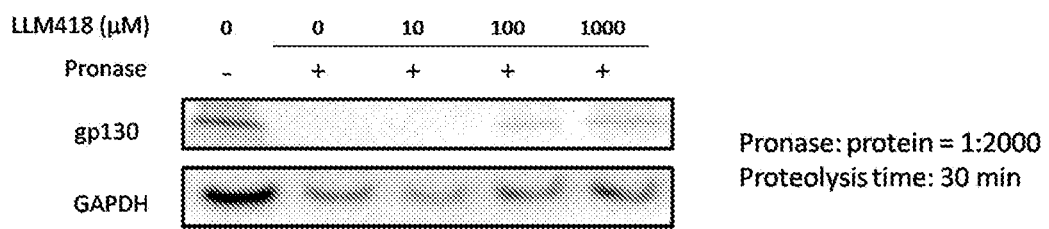
FIG. 15. depicts the confirmatory binding of LLM418 to gp130 in SUM159 breast cancer cell lysates using a 1:2000 ratio of pronase:protein with a proteolysis time of 30 minutes. These results suggest the direct binding of LLM418 to gp130 stabilizes its structure and therefore protects it from proteolytic digestion.
Figure 16:
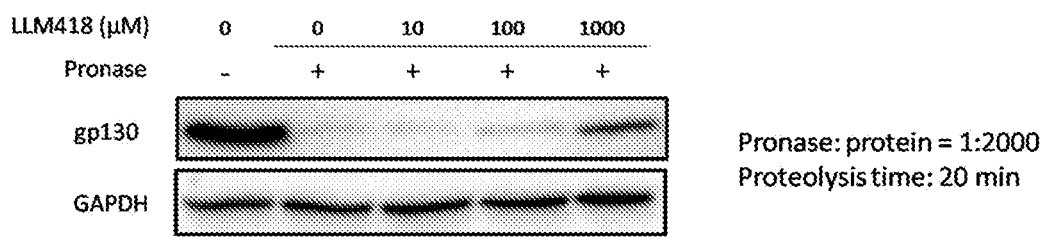
FIG. 16. depicts the confirmatory binding of LLM418 to gp130 in SUM159 breast cancer cell lysates using a 1:2000 ratio of pronase:protein with a proteolysis time of 20 minutes. These results suggest the direct binding of LLM418 to gp130 stabilizes its structure and therefore protects it from proteolytic digestion.
Figure 17:
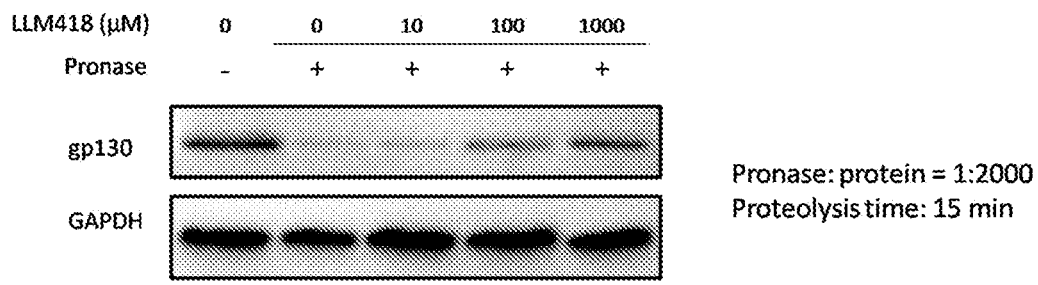
FIG. 17. depicts the confirmatory binding of LLM418 to gp130 in SUM159 breast cancer cell lysates using a 1:2000 ratio of pronase:protein with a proteolysis time of 15 minutes. These results suggest the direct binding of LLM418 to gp130 stabilizes its structure and therefore protects it from proteolytic digestion.

The DARTS assay is a method for studying the specific protein-ligand binding interactions. It is based on the principle that the target protein structure might be stabilized and become less susceptible to proteolysis by proteases upon drug binding [Lomenick B, Jung G, Wohlschlegel J, et al. Target identification using drug affinity responsive target stability (DARTS). *Curr Protoc Chem Biol* 2011, 3, 163-180; Lomenick B, Olsen R, Huang J. Identification of direct protein targets of small molecules. *ACS Chem Biol.* 2011, 6, 34-46]. It can be used to find the targeting protein of a small molecule by running SDS-gel without purifying any specific protein. It can also be used to verify whether a small molecule is targeting a designated protein by western blotting. Recently, this method was successfully used to assess the direct binding of potential inhibitor SC144 to gp130 in human ovarian cells and raloxifene to gp130 in human RH30 sarcoma cells [Li H, Xiao H, Lin L, et al. Drug design targeting protein-protein interactions (PPIs) using multiple ligand simultaneous docking (MLSD) and drug repositioning: discovery of raloxifene and bazedoxifene as novel inhibitors of IL-6/GP130 interface. *J Med Chem* 2014, 57, 632-641; Xu S, Grandel F, Garofalo A, et al. Discovery of a novel orally active small-molecule gp130 inhibitor for the treatment of ovarian cancer. *Mol Cancer Ther* 2013, 12, 937-949]. To investigate the binding of LLM418 to gp130, DARTS assays were performed using breast cancer cell SUM159 lysates, following the protocol as previously described. At first, an attempt was made to digest the lysates at a ratio of pronase:protein=1:1000 for 30 min. After running western blot assay, almost all the proteins employed (gp130 and GAPDH) were totally hydrolyzed so no bands were shown (FIG. 14). Then the amount of pronase was decreased to pronase:protein=1:2000 and hydrolysis was allowed to occur for 30, 20 and 15 min. (FIGS. 15-17) Finally, with the condition allowing a proteolysis time of 15 min, the drug restored targeted protein in a clearer dose-dependent manner than in the other two conditions. As is shown in FIG. 30, the abundance of the gp130 band was increased with an increasing dose of LLM418, which demonstrated that gp130 was protected from proteolysis via LLM418 binding. Particularly, at 100 and 1000 µM, the abundance of gp130 increased significantly compared with the no drug control. This result confirmed that LLM418 is able to directly bind to gp130 and thus induce its conformational change, making it more stable to pronase proteolysis.

SPR Experiments Strategies on GP130 Protein

The SPR binding assays were performed on multiple gp130 protein sources including commercially available products (gp130 full ectodomains with/without His & Fc Tag at C-terminus, 10974-HCCH-200 and 10974-H03H-20, respectively, Sino Biolobical Inc.) and in-house purified gp130-D1-D3 protein. Different immobilization strategies were tested including a conventional primary amine coupling method on a CM5 chip and a capture-coupling method on a NTA chip. The standard amine coupling method activates the carboxylic acids on the CM5 chip with EDC (1-ethyl-3-(3-dimethylaminopropyl)-carbodiimide) and NHS (N-hydroxysuccinimide). The protein is attracted to the surface under a low ionic strength environment and then coupled through primary amines. In the alternative capture-coupling method on the NTA chip (CM5 chip with additional nitrilotriacetic acid installed), proteins with histidine tags are captured by NTA attraction followed by coupling primary amines in close proximity to the activated surface. The second method is advantageous as it avoids damage to proteins in low ionic strength solutions and facilitates a directional immobilization with more functional binding sites available to the inhibitors.

To obtain optimal results in small molecule binding experiments using SPR, a high level of immobilized protein on the surface is usually required to give observable signals due to the large molecular weight ratio between the small molecules and the immobilized proteins. However, in the case of gp130 proteins, the maximal immobilization level that could be achieved was around 9000 RU. There was no evidence suggesting higher immobilization levels or higher binding signals in the capture-coupling method as compared to the standard amine coupling method. The gp130 ectodomains contain more than ten N-glycosylation sites [Moritz, R. L.; Hall, N. E.; Connolly, L. M.; Simpson, R. J., Determination of the disulfide structure and N-glycosylation sites of the extracellular domain of the human signal transducer gp130. *The Journal of Biological Chemistry* 2001, 276 (11), 8244-53], which could be the reason for not achieving a higher level of immobilization. This posttranslational modification entails long carbohydrate tails that surround the globular protein thereby blocking the access of primary amines. The coupling with the dextran surface on chips might be hampered due to steric hindrance. For this reason, detailed studies only with the amine coupling method on the conventional CM5 chip were carried out. In order to minimize off-target effects, gp130-D1-D3 proteins were used to obtain final results as our inhibitors are designed to bind to the gp130-D1 domain. Additional domains were not necessary and the Fc tag, albeit beneficial for purification, would introduce off-target binding in SPR.

Binding Affinities of IL-6 Inhibitors

At inhibitor concentrations higher than 100 µM, the expected saturation of binding signals (including MDL-A) was not observed, which suggests that there is non-specific binding between inhibitors and gp130-D1-D3 when all binding sites are occupied. The cLogP values of these inhibitors range from 3 to 6. However, all of them showed non-specific binding at high concentrations. This is believed to be due to a relatively plain topology, these molecules are attached to other flat surfaces on gp130-D1-D3 proteins under SPR conditions either due to complimentary shape or hydrophobic effects. The non-specific binding was observed on both CM5 and NTA chips. Increase of DMSO concentrations from 5% to 10% did not solve the problem.

Figure 18:
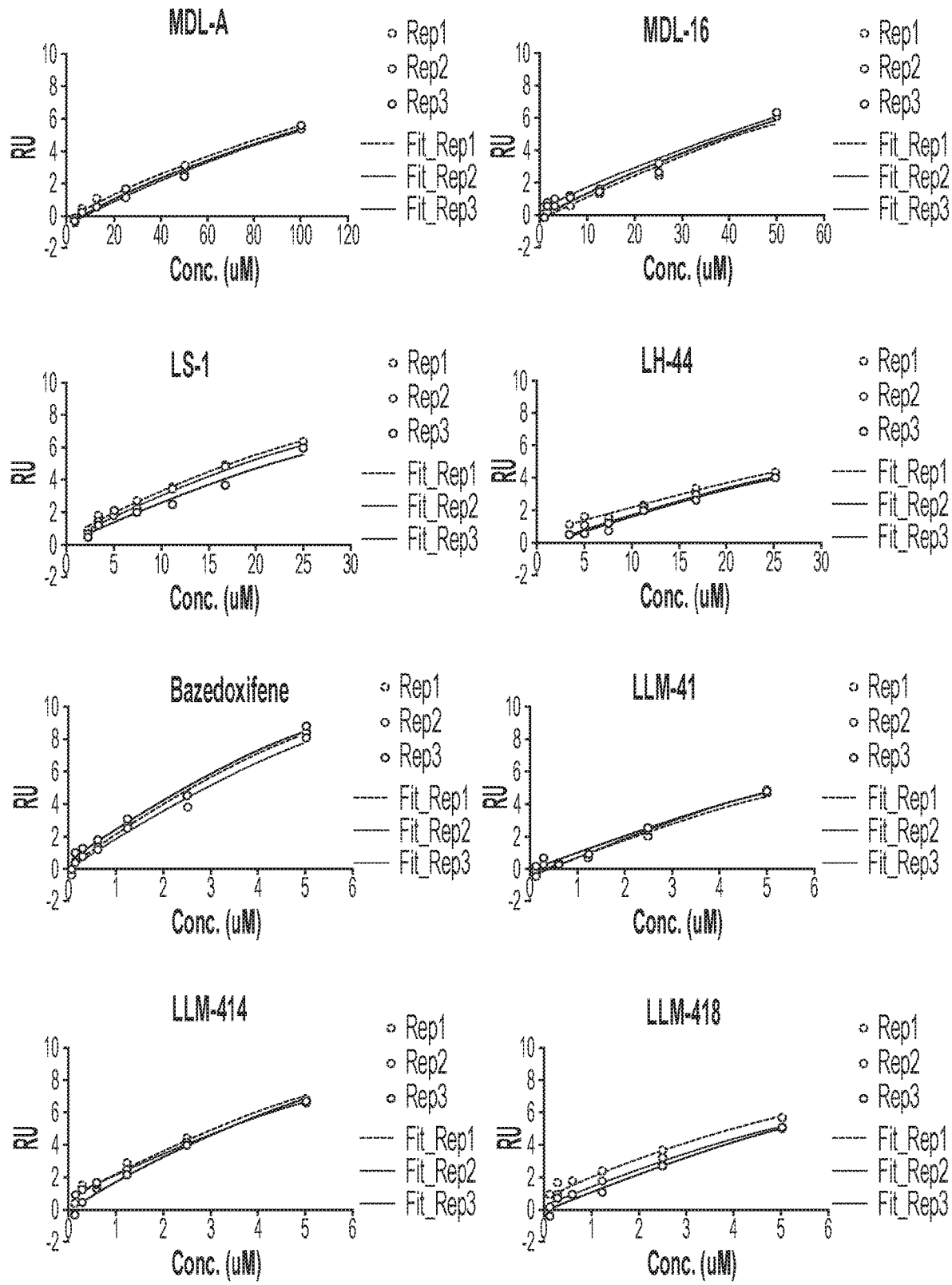
FIG. 18. depicts the binding affinity fitting curves of various IL-6 inhibitors.

In order to produce reliable results, it was decided to utilize the binding signals reported at low inhibitor concentrations. At low saturation levels, binding signals increase proportionally to inhibitor concentrations. The linear relationship discontinues when approaching full occupancy. To determine the concentration cut-off of the linear binding range, two aspects have to be considered: 1. due to potential protein degradation and dysfunction during immobilization, the protein binding sites are not always fully functional. Therefore, it was assumed that 25% occupancy is the maximal inhibitors binding in practice; 2. since the $K_D$ is usually determined at half maximum inhibitor concentration, the linear concentration range was set at quarter maximum. Therefore, the concentration cut-off of the linear range was determined as the inhibitor concentration corresponding to a binding response of 6 to 8 RUs, which is 12.5% (25%*25%) of the theoretical Rmax. The concentration cut-offs are 100 µM for MDL-A, 50 µM for MDL-16, 25 µM for LS-1 and LH-44, and 5 µM for Bazedoxifene, LLM-41, LLM-414, and LLM-418. Either 2-fold or 1.5-fold concentration series were generated from the cutoff concentration to yield 6 to 7 concentrations in total for each molecule. The results are summarized in Table 6 and the linear fitting curves are shown in FIG. 18. All IL-6/gp130 inhibitors display fast-on fast-off binding patterns.

By utilizing the binding signals at low inhibitor concentrations within the linear range and assigning 25% occupancy of the protein binding sites as the practical maximum that inhibitors can achieve, it was possible to reproduce the MDL-A binding affinity at 329.5 µM, which is close to a reported binding affinity of 288 µM [Saleh, A. Z. M.; Greenman, K. L.; Billings, S.; Van Vranken, D. L.; Krolewski, J. J., Binding of Madindoline A to the Extracellular Domain of gp130. *Biochemistry* 2005, 44 (32), 10822-

10827]. This result suggested that the developed linear regression strategy is able to determine the binding affinities reliably. Standard error percentages (SE %) for all molecules were within 10% suggesting that the linear regressions were statistically significant (Biacore Handbook).

TABLE 6

Direct Binding Affinities of IL-6 Inhibitors

| | M.W. (g/mol) | 25% Rmax | $K_D$ (µM) | Std. | SE % | ΔGexp (kcal/mol) |
|---|---|---|---|---|---|---|
| MDL-A | 369.46 | 24.08 | 329.5 | 2.89 | 6.99 | −4.75 |
| MDL-16 | 473.57 | 30.86 | 212.4 | 6.59 | 8.66 | −5.01 |
| LS-1 | 377.44 | 24.60 | 82.4 | 5.62 | 8.88 | −5.57 |
| LH-44 | 334.41 | 21.79 | 108.6 | 6.76 | 9.33 | −5.40 |
| Bazedoxifene | 471.61 | 30.73 | 13.7 | 0.57 | 6.6 | −6.63 |
| LLM-41 | 405.52 | 26.43 | 21.6 | 1.4 | 8.48 | −6.36 |
| LLM-414 | 406.51 | 26.49 | 15.6 | 1.83 | 7.34 | −6.55 |
| LLM-418 | 391.49 | 25.51 | 20.5 | 1.35 | 8.59 | −6.39 |

The direct binding affinities of inhibitors show an overall consistency with $IC_{50}$ values in assays with cancer cells in vitro (Table 7). Increasing binding affinities were observed across the generations of inhibitors. The $K_D$ value of MDL-16 is moderately improved as compared to that of MDL-A, whereas those of LS-1 and LH-44 are markedly lower. As expected from the in vitro $IC_{50}$ values, the LLM-4x molecules and Bazedoxifene display the highest binding affinities with $K_D$ values around or below 20 µM. Overall, the binding affinities were improved by a factor of 15. More importantly, the gradual improvements in binding affinities provide a relatively wide range of experimental binding energies ranging from −4.57 kcal/mol to −6.63 kcal/mol.

TABLE 7

Cancer Cellular $IC_{50}$ Values and Binding Affinities of IL-6/GP130 Inhibitors

| | $IC_{50}$ (µM) | | $K_D$ (µM) |
|---|---|---|---|
| | SUM159 | BxPC-3 | |
| MDL-A | NA | NA | 329.5 |
| MDL-16 | 22 | 16 | 212.4 |
| LS-1 | 23 | >50 | 82.4 |
| LH-44 | 25 | 13 | 108.6 |
| Bazedoxifene | 4.6 | 1.8 | 13.7 |
| LLM-41 | 14 | 13 | 21.6 |
| LLM-414 | 2.8 | 8.3 | 15.6 |
| LLM-418 | 1.7 | 1.2 | 20.5 |

Assessment of IL-6 Inhibitors in PE/CA-PJ49 Cell Line

Protein tyrosine phosphate receptor type D (PTPRD) is reported to serve as a tumor suppressor in various human cancers [Peyser et. al, PLoS One (2015) 10(8)]. PTPRD mutation is also known to be associated with increased STAT3 expression [Peyser et. al, PLoS One (2015) 10(8)]. Table 8 captures the inhibitory activities of various compounds in the PTPRD mutant cell line, PE/CA-PJ49.

TABLE 8

Inhibitory Activities of Various Compounds Against PE/CA-PJ49

| Compounds | $IC_{50}$ (48 h) |
|---|---|
| LLL12 | 18.97 ± 2.83 nM |
| LLL12B | 15.87 ± 3.71 nM |
| LY17 | 0.329 ± 0.079 µM |
| SC144 | 0.691 ± 0.064 µM |

TABLE 8-continued

Inhibitory Activities of Various Compounds Against PE/CA-PJ49

| Compounds | $IC_{50}$ (48 h) |
|---|---|
| LLM414 | 3.41 ± 0.99 µM |
| LLM418 | 1.79 ± 0.48 µM |

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed is:

1. A compound of Formula (XV), or a pharmaceutically acceptable salt thereof:

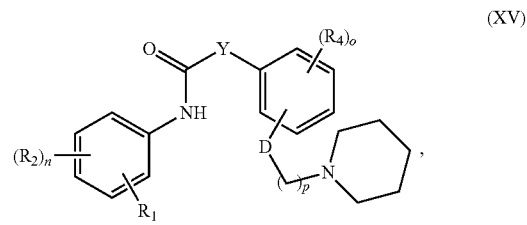

wherein:
$R_1$ is selected from the group consisting of pyrrolyl, pyrazolyl, imidazolyl, isoxazolyl, oxazolyl, isothiazolyl, thiazolyl, oxadiazolyl, thiadiazolyl, triazolyl, tetrazolyl, oxatriazolyl, pyrazinyl, pyridyl, pyridazinyl, pyrimidinyl, azetidinonyl, azetidinethionyl, pyrrolidinonyl, pyrrolidinethionyl, piperidinonyl, piperidinethionyl, tetrahydropyrimidinonyl, tetrahydropyrimidinethionyl, imidazolidinonyl, imidazolidinethionyl, 1,3-diazetidinonyl, 1,3-diazetidinethionyl, 1,2-oxazetidinyle, 1,2-thiazetidinyl, isoxazolidinyl, isothiazolidinyl, 1,2-oxazinanyl, 1,2-thiazinanyl, pyrimidinedionyl, 5-methylpyrimidine-2,4(1H,3H)-dionyl, isoxazol-5 (2H)-onyl, 1,7-dihydro-2H-pyrrolo[2,3-d]pyrimidine-2,4(3H)-dionyl, 1,4,5,6-tetrahydro-7H-indol-7-onyl, 1H-pyrrolo[2,3-b]pyridyl, quinazoline-2,4(1H,3H)-dionyl, furo[2,3-d]pyrimidine-2,4(1H,3H)-dionyl, 1,3-dihydro-2H-benzo[d]imidazol-2-onyl, 1H-indole-4,7-dionyl, 5,6-dimethyl-1H-indole-4,7-dionyl, 5,6-dihydro-1H-indole-4,7-dionyl, 4,5-dihydropyrano[3,4-b]pyrrol-7(1H)-onyl, 1,4,5,6-tetrahydro-7H-pyrrolo[2,3-c]pyridin-7-onyl, 1,6-dihydro-7H-pyrrolo[2,3-c]pyridin-7-onyl, pyrano[3,4-b]pyrrol-7(1H)-onyl, 1,3-dihydro-2H-imidazol-2-onyl, 4-fluoro-1H-pyrazolyl, 3,4-difluoro-1H-pyrazolyl, 3-fluoro-1H-pyrazolyl, 4-chloro-1H-pyrazolyl, 3,4-dichloro-1H-pyrazolyl, 3-chloro-1H-pyrazolyl, 3-methoxy-1H-pyrazolyl, 1H-pyrazol-3-yl acetate, 4-methoxy-1H-pyrazolyl, 1H-pyrazol-4-yl acetate, N-(1H-pyrazol-4-yl)acetamidyl, N,N-dimethyl-1H-pyrazol-4-amino, N,N-dimethyl-1H-pyrazol-3-amino, 4-(trifluoromethyl)-1H-pyrazolyl, 3-(trifluoromethyl)-1H-pyrazolyl, N-(1H-pyrazol-3-yl)acetamide, and 1H-pyrazol-3-amino;

each $R_2$ is independently halo, cyano, —$OR_5$, $NO_2$, alkyl, or —$NR_6R_7$;

each $R_4$ is independently halo, cyano, —$OR_5$, $NO_2$, alkyl, haloalkyl, hydroxyalkyl, alkoxyalkyl, or —$NR_6R_7$;

each $R_5$ is independently hydrogen or alkyl;

each $R_6$ is independently hydrogen or alkyl;

each $R_7$ is independently hydrogen or alkyl;

D is —O—;

Y is a bond, —O—N($R_6$)—;

n is 0, 1, or 2;

o is 0; and p is 2, 3, or 4.

2. The compound of claim 1, or pharmaceutically acceptable salt thereof, wherein Y is a bond or —$NR_6$—.

3. The compound of claim 1, or pharmaceutically acceptable salt thereof, wherein $R_1$ is pyrrolyl, pyrazolyl, imidazolyl, isoxazolyl, oxazolyl, isothiazolyl, thiazolyl, oxadiazolyl, thiadiazolyl, triazolyl, tetrazolyl, oxatriazolyl, pyrazinyl, pyridyl, pyridazinyl, or pyrimidinyl.

4. The compound of claim 1, or pharmaceutically acceptable salt thereof, wherein $R_1$ is

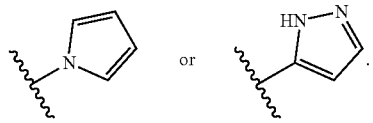 [SMILES: *n1cccc1 ; *c1ccn[nH]1]

5. The compound of claim 1, wherein the compound is selected from:

N-(5-fluoro-2-(1H-pyrrol-1-yl)phenyl)-4-(2-(piperidin-1-yl)ethoxy)benzamide (LLM3);

N-(5-fluoro-2-(1H-pyrrol-1-yl)phenyl)-4-(3-(piperidin-1-yl)propoxy)benzamide (LLM4);

N-(5-fluoro-2-(1H-pyrrol-1-yl)phenyl)-4-phenethoxybenzamide (LLM5);

N-(5-fluoro-2-(1H-pyrrol-1-yl)phenyl)-4-(3-phenylpropoxy)benzamide (LLM6);

N-(5-fluoro-2-(1H-pyrrol-1-yl)phenyl)-4-(4-phenylbutoxy)benzamide (LLM7);

N-(3-(1H-pyrazol-5-yl)phenyl)-4-(3-(piperidin-1-yl)propoxy)benzamide (LLM41);

N-(3-(1H-pyrazol-5-yl)phenyl)-4-(2-(piperidin-1-yl)ethoxy)benzamide (LLM42);

N-(3-(1H-pyrazol-5-yl)phenyl)-3-(3-(piperidin-1-yl)propoxy)benzamide (LLM45);

N-(3-(1H-pyrazol-5-yl)phenyl)-3-(2-(piperidin-1-yl)ethoxy)benzamide (LLM46);

1-(3-(1H-pyrazol-5-yl)phenyl)-3-(3-(3-(piperidin-1-yl)propoxy)phenyl)urea (LLM413);

1-(3-(1H-pyrazol-5-yl)phenyl)-3-(3-(2-(piperidin-1-yl)ethoxy)phenyl)urea (LLM414);

N-(2-(1H-pyrazol-5-yl)phenyl)-4-(3-(piperidin-1-yl)propoxy)benzamide (LLM417);

N-(2-(1H-pyrazol-5-yl)phenyl)-4-(2-(piperidin-1-yl)ethoxy)benzamide (LLM418);

and pharmaceutically acceptable salts thereof.

6. A pharmaceutical composition comprising a compound of claim 1, or a pharmaceutical salt thereof, and a pharmaceutically acceptable carrier.

7. The compound of claim 1, or pharmaceutically acceptable salt thereof, wherein $R_1$ is selected from pyrrolyl, pyrazolyl, azetidinonyl, azetidinethionyl, pyrrolidinonyl, pyrrolidinethionyl, piperidinonyl, piperidinethionyl, tetrahydropyrimidinonyl, tetrahydropyrimidinethionyl, imidazolidinonyl, imidazolidinethionyl, 1,3-diazetidinonyl, 1,3-diazetidinethionyl, 1,2-oxazetidinyle, 1,2-thiazetidinyl, isoxazolidinyl, isothiazolidinyl, 1,2-oxazinanyl, 1,2-thiazinanyl, pyrimidinedionyl, 5-methylpyrimidine-2,4(1H,3H)-dionyl, isoxazol-5(2H)-onyl, 1,7-dihydro-2H-pyrrolo[2,3-d]pyrimidine-2,4(3H)-dionyl, 1,4,5,6-tetrahydro-7H-indol-7-onyl, 1H-pyrrolo[2,3-b]pyridyl, quinazoline-2,4(1H,3H)-dionyl, furo[2,3-d]pyrimidine-2,4(1H,3H)-dionyl, 1,3-dihydro-2H-benzo[d]imidazol-2-onyl, 1H-indole-4,7-dionyl, 5,6-dimethyl-1H-indole-4,7-dionyl, 5,6-dihydro-1H-indole-4,7-dionyl, 4,5-dihydropyrano[3,4-b]pyrrol-7(1H)-onyl, 1,4,5,6-tetrahydro-7H-pyrrolo[2,3-c]pyridin-7-onyl, 1,6-dihydro-7H-pyrrolo[2,3-c]pyridin-7-onyl, pyrano[3,4-b]pyrrol-7(1H)-onyl, 1,3-dihydro-2H-imidazol-2-onyl, 4-fluoro-1H-pyrazolyl, 3,4-difluoro-1H-pyrazolyl, 3-fluoro-1H-pyrazolyl, 4-chloro-1H-pyrazolyl, 3,4-dichloro-1H-pyrazolyl, 3-chloro-1H-pyrazolyl, 3-methoxy-1H-pyrazolyl, 1H-pyrazol-3-yl acetate, 4-methoxy-1H-pyrazolyl, 1H-pyrazol-4-yl acetate, N-(1H-pyrazol-4-yl)acetamidyl, N,N-dimethyl-1H-pyrazol-4-amino, N,N-dimethyl-1H-pyrazol-3-amino, 4-(trifluoromethyl)-1H-pyrazolyl, 3-(trifluoromethyl)-1H-pyrazolyl, N-(1H-pyrazol-3-yl)acetamide, and 1H-pyrazol-3-amino.

8. The compound of claim 1, or pharmaceutically acceptable salt thereof, wherein Y is —NH—.

9. The compound of claim 1, or pharmaceutically acceptable salt thereof, wherein Y is a bond.

10. The compound of claim 1, or pharmaceutically acceptable salt thereof, wherein p is 2.

11. The compound of claim 1, or pharmaceutically acceptable salt thereof, wherein p is 3.

12. The compound of claim 1, or pharmaceutically acceptable salt thereof, wherein n is 0.

13. The compound of claim 1, or pharmaceutically acceptable salt thereof, wherein n is 1.

14. The compound of claim 1, or pharmaceutically acceptable salt thereof, wherein n is 2.

15. The compound of claim 1, or pharmaceutically acceptable salt thereof, wherein $R_2$ is halo, alkyl, or —$OR_5$.

16. The compound of claim 1, or pharmaceutically acceptable salt thereof, wherein $R_2$ is fluoro, bromo, methyl, methoxy, or hydroxy.

17. The compound of claim 1, or pharmaceutically acceptable salt thereof, wherein $R_1$ is pyrazolyl.

18. The compound of claim 1, or pharmaceutically acceptable salt thereof, wherein $R_1$ is pyrrolyl.

19. A compound of formula:

N-(3-(1H-pyrazol-5-yl)phenyl)-3-(piperidin-1-yl)benzamide (LLM437); or

N-(3-(1H-pyrazol-5-yl)phenyl)-3-(piperidin-1-ylmethyl)benzamide (LLM438);

or pharmaceutically acceptable salt thereof.

20. The pharmaceutical composition of claim 6, further comprising an additional therapeutic agent.

* * * * *